US008951512B2

(12) United States Patent
Blaser et al.

(10) Patent No.: US 8,951,512 B2
(45) Date of Patent: Feb. 10, 2015

(54) METHODS FOR TREATING BONE DISORDERS BY CHARACTERIZING AND RESTORING MAMMALIAN BACTERIAL MICROBIOTA

(75) Inventors: Martin J. Blaser, New York, NY (US); Ilseung Cho, New York, NY (US); Laura Cox, Brooklyn, NY (US)

(73) Assignee: New York University, New York, NY (US)

( * ) Notice: Subject to any disclaimer, the term of this patent is extended or adjusted under 35 U.S.C. 154(b) by 413 days.

(21) Appl. No.: 13/100,977

(22) Filed: May 4, 2011

(65) Prior Publication Data

US 2011/0280840 A1 Nov. 17, 2011

Related U.S. Application Data

(60) Provisional application No. 61/331,306, filed on May 4, 2010.

(51) Int. Cl.
*A61K 35/74* (2006.01)
(52) U.S. Cl.
USPC .......................................................... 424/93.4
(58) Field of Classification Search
USPC .......................................................... 424/93.4
See application file for complete search history.

(56) References Cited

U.S. PATENT DOCUMENTS

| | | | |
|---|---|---|---|
| 2001/0001711 A1 | 5/2001 | Olshenitsky et al. | |
| 2002/0048567 A1 | 4/2002 | Olshenitsky et al. | |
| 2002/0048568 A1 | 4/2002 | Olshenitsky et al. | |
| 2002/0048569 A1 | 4/2002 | Olshenitsky et al. | |
| 2002/0048570 A1 | 4/2002 | Olshenitsky et al. | |
| 2002/0051772 A1 | 5/2002 | Olshenitsky et al. | |
| 2002/0051773 A1 | 5/2002 | Olshenitsky et al. | |
| 2002/0051774 A1 | 5/2002 | Olshenistsky et al. | |
| 2002/0051775 A1 | 5/2002 | Olshenitsky et al. | |
| 2002/0051776 A1 | 5/2002 | Olshenitsky et al. | |
| 2002/0054866 A1 | 5/2002 | Olshenitsky et al. | |
| 2002/0054867 A1 | 5/2002 | Olshenitsky et al. | |
| 2002/0054868 A1 | 5/2002 | Olshenitsky et al. | |

(Continued)

FOREIGN PATENT DOCUMENTS

| | | |
|---|---|---|
| EP | 1886680 | 2/2008 |
| WO | 00/75284 A1 | 12/2000 |

(Continued)

OTHER PUBLICATIONS

Holzapfel et al., "Overview of gut flora and probiotics," Int J Food Microbiol 41:85-101, 1998.*

(Continued)

*Primary Examiner* — Rosanne Kosson
(74) *Attorney, Agent, or Firm* — Troutman Sanders LLP

(57) ABSTRACT

The present invention relates to characterizing changes in mammalian gastrointestinal microbiota associated with antibiotic treatment and various disease conditions (such as obesity, metabolic syndrome, insulin-deficiency or insulin-resistance related disorders, glucose intolerance, diabetes, non-alcoholic fatty liver, abnormal lipid metabolism, short stature, osteoporosis, and other disorders of bone formation and mineralization, etc.) and related diagnostic and therapeutic methods. Therapeutic methods of the invention involve the use of probiotics, prebiotics, or narrow spectrum antibiotics/antibacterial agents that are capable of restoring healthy mammalian bacterial gastrointestinal microbiota.

54 Claims, 28 Drawing Sheets

(56) References Cited

U.S. PATENT DOCUMENTS

| | | | |
|---|---|---|---|
| 2002/0071835 | A1 | 6/2002 | Olshenitsky et al. |
| 2004/0028689 | A1 | 2/2004 | Borody |
| 2004/0052909 | A1* | 3/2004 | Contento et al. ............... 426/99 |
| 2004/0265291 | A1 | 12/2004 | Drake et al. |
| 2005/0037089 | A1* | 2/2005 | Jobbins ........................ 424/602 |
| 2005/0176001 | A1 | 8/2005 | Nakano et al. |
| 2006/0088514 | A1 | 4/2006 | O'Mahony et al. |
| 2007/0009577 | A1 | 1/2007 | Mankovitz |
| 2009/0035329 | A1 | 2/2009 | Blaser et al. |
| 2010/0074872 | A1 | 3/2010 | Blaser et al. |
| 2010/0172874 | A1 | 7/2010 | Turnbaugh et al. |
| 2012/0058094 | A1 | 3/2012 | Blaser et al. |
| 2012/0171193 | A1 | 7/2012 | Blaser et al. |

FOREIGN PATENT DOCUMENTS

| | | | |
|---|---|---|---|
| WO | WO 0115715 A2 * | 3/2001 | |
| WO | 2009/018447 A2 | 2/2009 | |
| WO | WO 2012/024638 | 2/2012 | |

OTHER PUBLICATIONS

Tuohy et al., "Using probiotics and prebiotics to improve gut health," Therapeutic Focus 8(15):692-700, 2003.*
Andersson et al., Comparative analysis of human gut microbiota by barcoded pyrosequencing, PLoS ONE, vol. 3 Issue 7, e2836, pp. 1-8, 2008.
Armougom et al., Monitoring Bacterial Community of Human Gut Microbiota Reveals an Increase in *Lactobacillus* in Obese Patients and Methanogens in Anorexic Patients, PLoS ONE, vol. 4, p. e7125, 2009.
Armougom et al., Use of pyrosequencing and DNA barcodes to monitor variations in Firmicutes and Bacteroidetes communities in the gut microbiota of obese humans, BMC Genomics, vol. 9, p. 576, 2008.
Bartosch, et al., Characterization of bacterial communities in feces from healthy elderly volunteers and hospitalized elderly patients by using real-time PCR and effects of antibiotic treatment on the fecal microbiota, Applied and Environmental Microbiology, vol. 70, No. 6, pp. 3575-3581, 2004.
Blaser et al., Does *Helicobacter pylori* protect against asthma and allergy? Gut, vol. 57, pp. 561-567, 2008.
Chen et al., *Helicobacter pylori* Colonization is Inversely Associated with Childhood Asthma, Journal of Infectious Diseases, vol. 198, pp. 553-560, 2008.
Cho et al., Antibiotics in early life alter the murine colonic microbiome and adiposity, Nature, vol. 488, pp. 621-626, 2012.
Duncan et al., Cultivable bacterial diversity from the human colon, Letters in Applied Microbiology, vol. 44, pp. 343-350, 2007.
Eckburg et al., Diversity of the Human Intestinal Microbial Flora, Science, vol. 308, pp. 1635-1638, 2005.
Flint, Antibiotics and adiposity, Nature, vol. 488, pp. 601-602, 2012.
Flint, The significance of prokaryote diversity in the human gastrointestinal tract, In SGM symposium 66: Prokaryotic Diversity: mechanisms and significance, Logan et al., eds., Cambridge University Press, pp. 65-90, 2012.
Fuller, Probiotics in man and animals, J. Applied Bacteriol., vol. 66, pp. 365-378, 1989.
Gao et al., Molecular analysis of human forearm superficial skin bacterial biota, Proc. Natl. Acad. Sci. USA, vol. 104, pp. 2927-2932, 2007.
Gao et al., Substantial Alterations of the Cutaneous Bacterial Biota in Psoriatic Lesions, PLoS One, vol. 3, pp. e2719-e2728, 2008.
Hopkins, et al., Age and disease related changes in intestinal bacterial populations assessed by cell culture, 16S rRNA abundance, and community cellular fatty acid profiles, Gut, vol. 48, pp. 198-205, 2001.
International Preliminary Report on Patentability issued in International Appl. No. PCT/US2009/058351, dated Mar. 29, 2011.
International Search Report issued in International Appl. No. PCT/US2009/058351, dated May 10, 2010.
International Search Report issued in International Appl. No. PCT/US2011/048501, dated Mar. 13, 2012.
Ley et al., Microbial ecology: Human gut microbes associated with obesity, Nature, vol. 444, pp. 1022-1023, 2006.
Ley et al., Obesity alters gut microbial ecology, Proc. Natl. Acad. Sci. USA, vol. 102, pp. 11070-11075, 2005.
Li et al., Symbiotic gut microbes modulate human metabolic phenotypes, Proc. Natl. Acad. Sci. USA, vol. 105, pp. 2117-2122, 2008.
Paulino et al., Molecular Analysis of Fungal Microbiota in Samples from Healthy Human Skin and Psoriatic Lesions, J Clin Microbiol, vol. 44, pp. 2933-2941, 2006.
Ray, Adding weight to the microbiota's role in obesity-exposure to antibiotics early in life can lead to increased adiposity, Nature Reviews/Gastroenterology & Hepatology, vol. 9, 2012.
Sonnerburg et al. Genomic and metabolic studies of the impact of probiotics on a model gut symbiont and host, PLoS Biol, vol. 4(12): e413, pp. 2213-2226, 2006.
Trasande et al, Infant antibiotic exposures and early-life body mass, International Journal of Obesity, advance online publication, pp. 1-8, (doi:10.1038/ijo.2012.132), 2012.
Turnbaugh et al., An obesity-associated gut microbiome with increased capacity for energy harvest, Nature, vol. 444, pp. 1027-1031, 2006.
Wade, Unculturable bacteria—the uncharacterized organisms that cause orl infections, Journal of The Royal Society of Medicine, vol. 95, pp. 81-83, 2002.
Wilson et al., Applications of molecular ecology in the characterization of uncultured microorganisms associated with human disease, Reviews in Medical Microbiology, vol. 8, pp. 91-101, 1997.
Written Opinion of International Searching Authority issued in International Appl. No. PCT/US2009/058351, dated May 10, 2010.
Written Opinion of International Searching Authority issued in International Appl. No. PCT/US2011/048501, dated Mar. 13, 2012.
Zoetendal, et al., High-throughput diversity and functionality analysis of the gastrointestinal tract microbiota, Gut, vol. 57, pp. 1605-1615, 2008.
Hong Hye Jin et al, "Differential suppression of allergen-induced airway inflammation in murine model of asthma by lactic acid bacteria", FASEB Journal, vol. 22, 2008, abstract.
Stockert K, "Physiological intestinal flora in children of 6 to 12 years of age with bronchial asthma", Deutsche Zeitschrift Fur Akupunktur 2001 DE, vol. 44, No. 4, 2001, pp. 268-271 (English abstract provided).
Morris et al, "*Helicobacter pylori* infection link to lower rates of asthma", Lancet Infectious Diseases, Elsevier Ltd., US, vol. 7, No. 6, 2007, p. 379.
Extended European Search Report, dated Feb. 28, 2013, which issued during the prosecution of European Patent Application No. 09816896.6.
Wen et al. "Innate immunity and intestinal microbiota in the development of Type I diabetes", Nature, vol. 455, pp. 1-6, 2008.

* cited by examiner

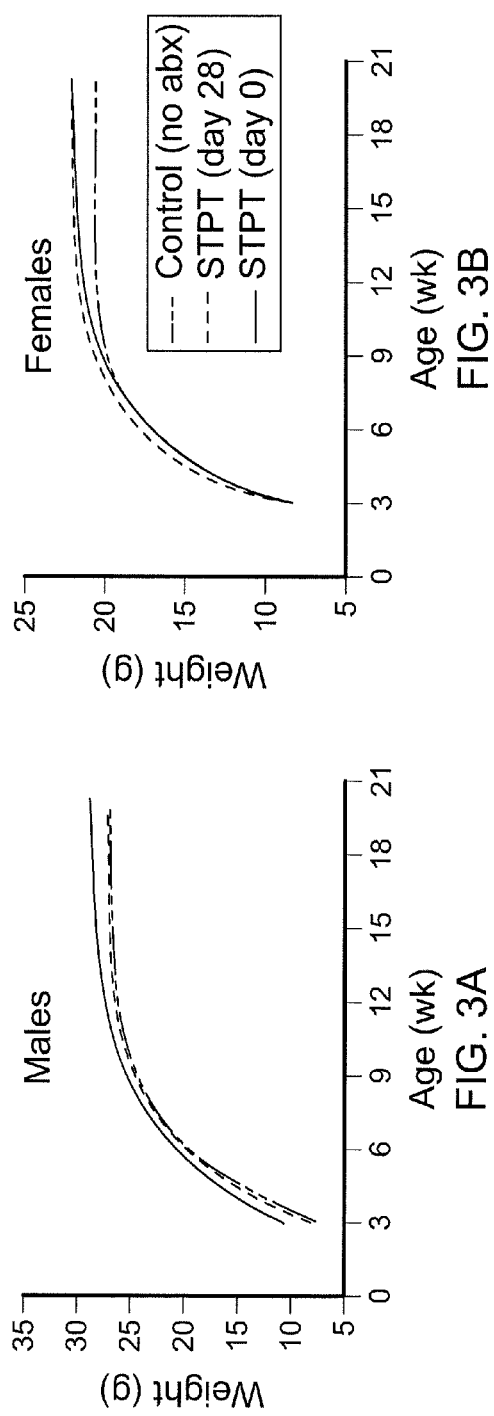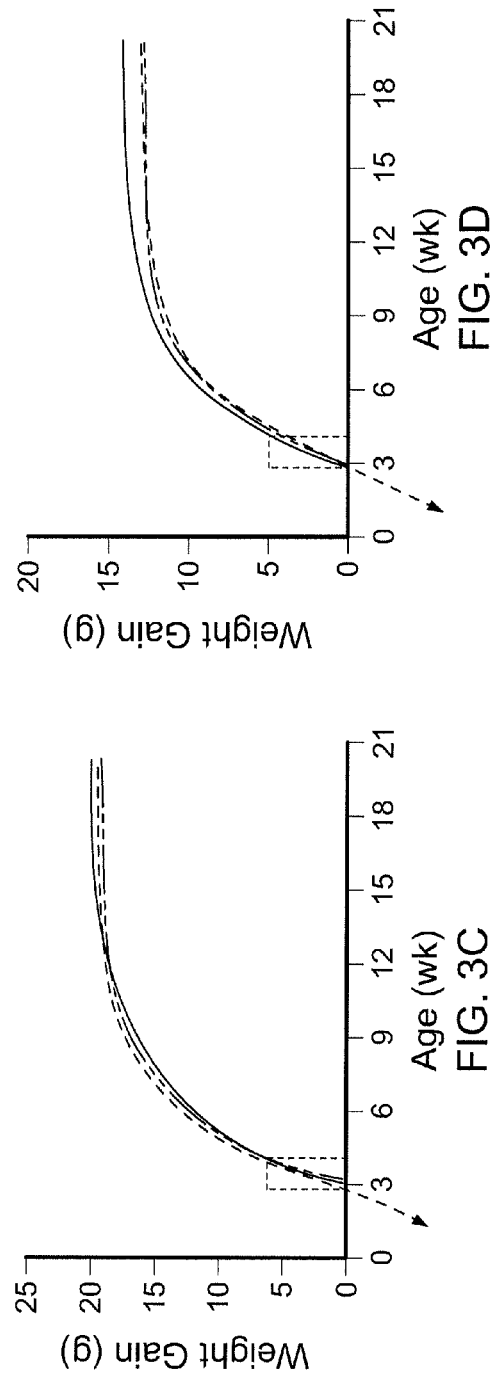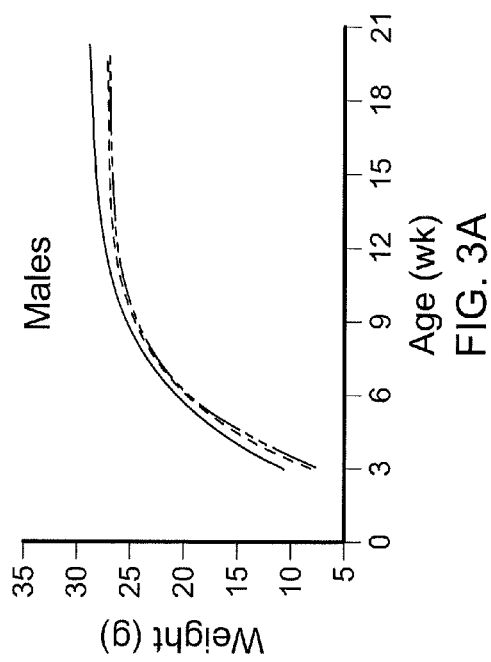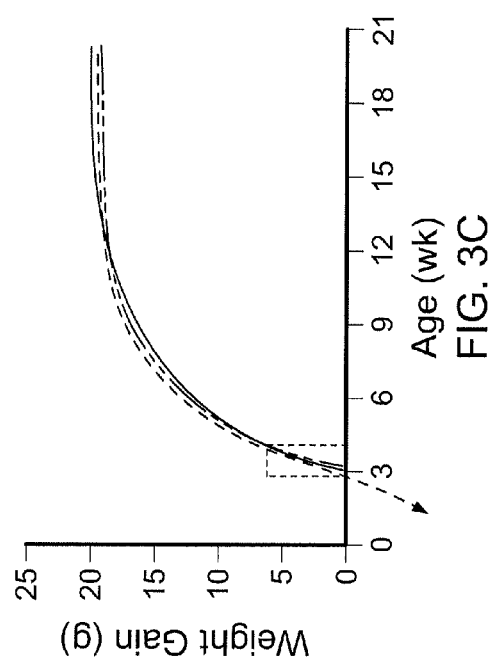

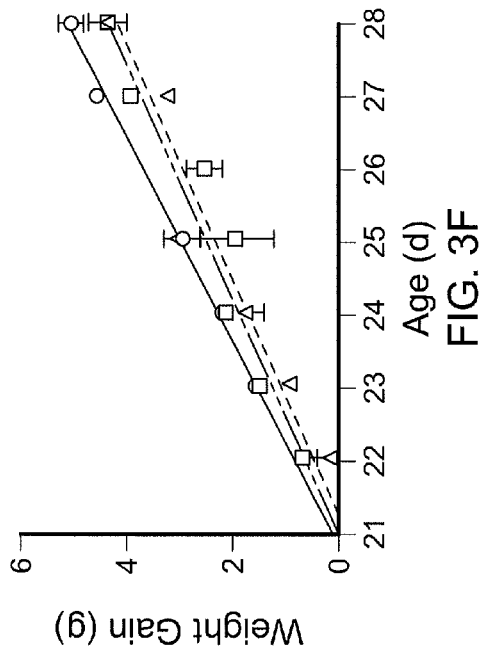
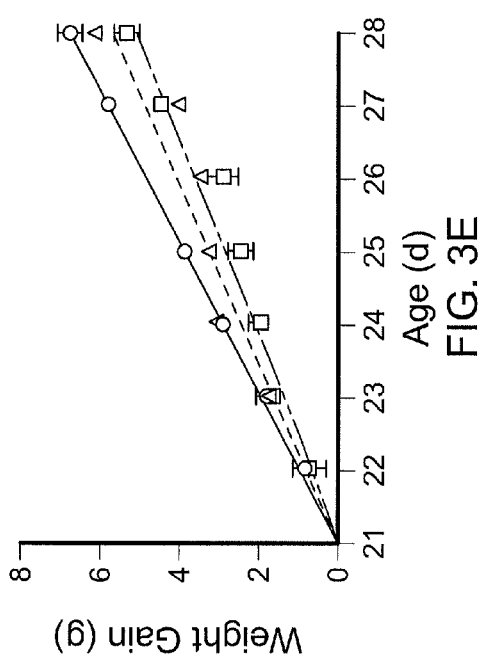
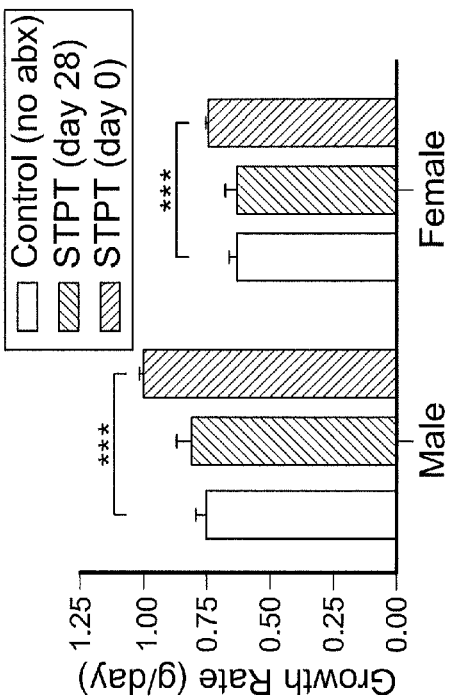
FIG. 3E
FIG. 3F
FIG. 3G
FIG. 3H

Control

STPT 28

STPT 0

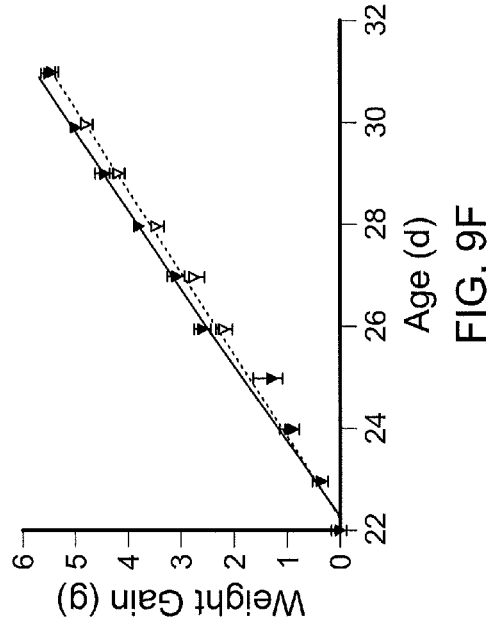
FIG. 9E
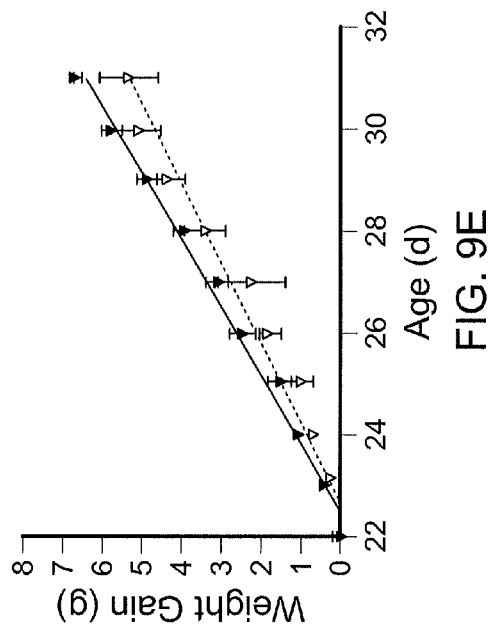
FIG. 9F
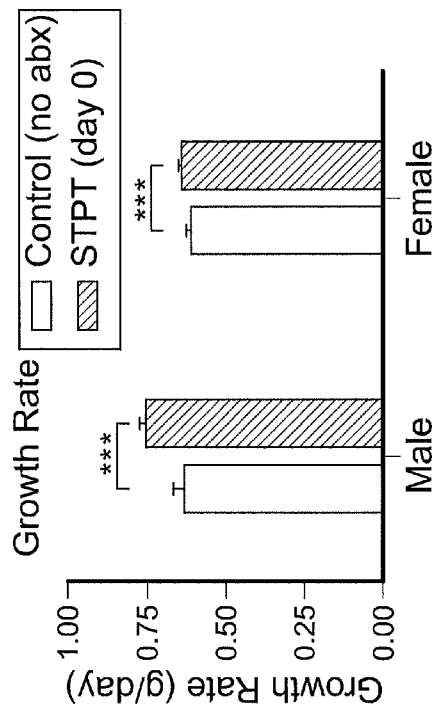
FIG. 9G
FIG. 9H

\* P < 0.05. \*\*\* P < 0.0005

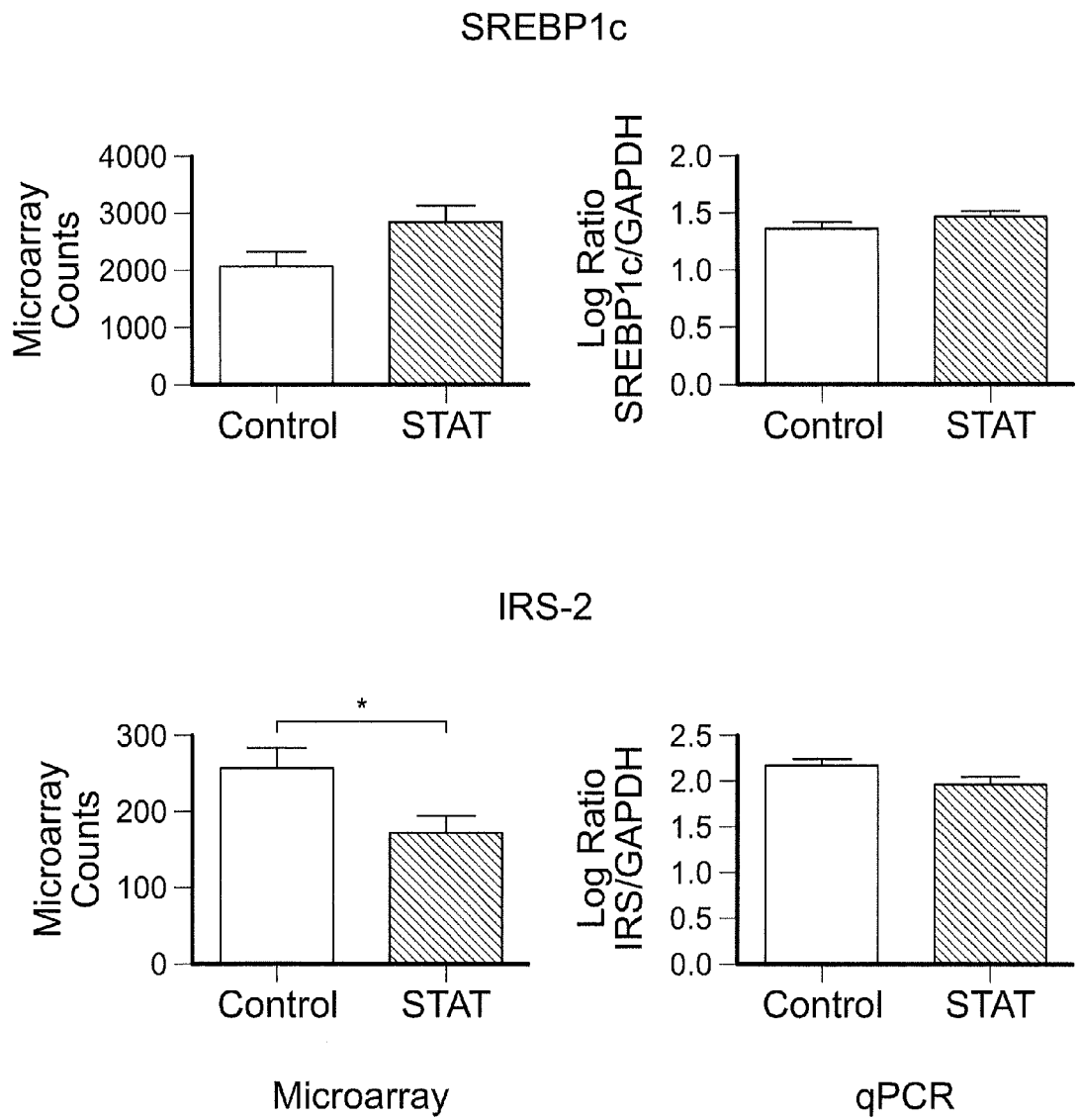
FIG. 15C (Cont...)

```
                        SEQUENCE LISTING

<160> NUMBER OF SEQ ID NOS: 24

<210> SEQ ID NO 1
<211> LENGTH: 17
<212> TYPE: DNA
<213> ORGANISM: Artificial Sequence
<220> FEATURE:
<223> OTHER INFORMATION: synthetically generated oligonucleotide

<400> SEQUENCE: 1
cctacgggag gcagcag                                                  17

<210> SEQ ID NO 2
<211> LENGTH: 17
<212> TYPE: DNA
<213> ORGANISM: Artificial Sequence
<220> FEATURE:
<223> OTHER INFORMATION: synthetically generated oligonucleotide

<400> SEQUENCE: 2
attaccgcgg ctgctgg                                                  17

<210> SEQ ID NO 3
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 3
ggarcatgtg gtttaattcg atgat                                         25

<210> SEQ ID NO 4
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 4
agctgacgac aaccatgcag                                               20

<210> SEQ ID NO 5
<211> LENGTH: 25
<212> TYPE: DNA
<213> ORGANISM: Artificial Sequence
<220> FEATURE:
<223> OTHER INFORMATION: synthetically generated oligonucleotide

<400> SEQUENCE: 5
ggagyatgtg gtttaattcg aagca                                         25

<210> SEQ ID NO 6
<211> LENGTH: 20
<212> TYPE: DNA
```

<213> ORGANISM: Artificial Sequence
<220> FEATURE:
<223> OTHER INFORMATION: synthetically generated oligonucleotide

<400> SEQUENCE: 6
agctgacgac aaccatgcac                                           20

<210> SEQ ID NO 7
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 7
actcctacgg gaggcagcag                                           20

<210> SEQ ID NO 8
<211> LENGTH: 17
<212> TYPE: DNA
<213> ORGANISM: Artificial Sequence
<220> FEATURE:
<223> OTHER INFORMATION: synthetically generated oligonucleotide

<400> SEQUENCE: 8
attaccgcgg ctgctgg                                              17

<210> SEQ ID NO 9
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 9
ctyggtcatt tagaggaagt aa                                        22

<210> SEQ ID NO 10
<211> LENGTH: 19
<212> TYPE: DNA
<213> ORGANISM: Artificial Sequence
<220> FEATURE:
<223> OTHER INFORMATION: synthetically generated oligonucleotide

<400> SEQUENCE: 10
rctgcgttct tcatcgwtg                                            19

<210> SEQ ID NO 11
<211> LENGTH: 32
<212> TYPE: DNA
<213> ORGANISM: Artificial Sequence
<220> FEATURE:
<223> OTHER INFORMATION: synthetically generated oligonucleotide
<220> FEATURE:
<221> NAME/KEY: misc_feature
<222> LOCATION: 3, 6, 23
<223> OTHER INFORMATION: n = inosine

<400> SEQUENCE: 11
gcngancatt tcactggaay wsntggcaya tg                             32

<210> SEQ ID NO 12
<211> LENGTH: 26
<212> TYPE: DNA
<213> ORGANISM: Artificial Sequence
<220> FEATURE:
<223> OTHER INFORMATION: synthetically generated oligonucleotide

```
<220> FEATURE:
<221> NAME/KEY: misc_feature
<222> LOCATION: 18
<223> OTHER INFORMATION: n = inosine
<220> FEATURE:
<221> NAME/KEY: misc_feature
<222> LOCATION: 24
<223> OTHER INFORMATION: n = A,T,C or G

<400> SEQUENCE: 12
cctgcctttg caatrtcnac raangc                                          26

<210> SEQ ID NO 13
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 13
gtwtgggcwa arggyggmga agg                                             23

<210> SEQ ID NO 14
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 14
gtattgdgty ttrgccatac a                                               21

<210> SEQ ID NO 15
<211> LENGTH: 18
<212> TYPE: DNA
<213> ORGANISM: Artificial Sequence
<220> FEATURE:
<223> OTHER INFORMATION: synthetically generated oligonucleotide

<400> SEQUENCE: 15
gccattgagt gccgagtc                                                   18

<210> SEQ ID NO 16
<211> LENGTH: 23
<212> TYPE: DNA
<213> ORGANISM: Artificial Sequence
<220> FEATURE:
<223> OTHER INFORMATION: synthetically generated oligonucleotide

<400> SEQUENCE: 16
catgtcgtag atgacaaatg gtg                                             23

<210> SEQ ID NO 17
<211> LENGTH: 22
<212> TYPE: DNA
<213> ORGANISM: Artificial Sequence
<220> FEATURE:
<223> OTHER INFORMATION: synthetically generated oligonucleotide

<400> SEQUENCE: 17
ggatctgaaa tcgaccttaa ag                                              22

<210> SEQ ID NO 18
<211> LENGTH: 22
<212> TYPE: DNA
<213> ORGANISM: Artificial Sequence
<220> FEATURE:
```

```
<223> OTHER INFORMATION: synthetically generated oligonucleotide

<400> SEQUENCE: 18
tagctggctt gaccaatatg tt                                              22

<210> SEQ ID NO 19
<211> LENGTH: 29
<212> TYPE: DNA
<213> ORGANISM: Artificial Sequence
<220> FEATURE:
<223> OTHER INFORMATION: synthetically generated oligonucleotide

<400> SEQUENCE: 19
ctggagtatt atgagtcgag aagaagtgg                                       29

<210> SEQ ID NO 20
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 20
tgtagagggc gatcaggtac ttgt                                            24

<210> SEQ ID NO 21
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 21
aacgtcactt ccagctagac                                                 20

<210> SEQ ID NO 22
<211> LENGTH: 21
<212> TYPE: DNA
<213> ORGANISM: Artificial Sequence
<220> FEATURE:
<223> OTHER INFORMATION: synthetically generated oligonucleotide

<400> SEQUENCE: 22
ccactaaggt gcctacagag c                                               21

<210> SEQ ID NO 23
<211> LENGTH: 20
<212> TYPE: DNA
<213> ORGANISM: Artificial Sequence
<220> FEATURE:
<223> OTHER INFORMATION: synthetically generated oligonucleotide

<400> SEQUENCE: 23
tggtgaaggt cggtgtgaac                                                 20

<210> SEQ ID NO 24
<211> LENGTH: 24
<212> TYPE: DNA
<213> ORGANISM: Artificial Sequence
<220> FEATURE:
<223> OTHER INFORMATION: synthetically generated oligonucleotide

<400> SEQUENCE: 24
ccatgtagtt gaggtcaatg aagg                                            24
```

METHODS FOR TREATING BONE DISORDERS BY CHARACTERIZING AND RESTORING MAMMALIAN BACTERIAL MICROBIOTA

CROSS REFERENCE TO RELATED APPLICATIONS

This application claims priority to U.S. Provisional Application Ser. No. 61/331,306 filed May 4, 2010, which is incorporated by reference herein in its entirety.

STATEMENT REGARDING FEDERALLY SPONSORED RESEARCH

Research and development leading to certain aspects of the present invention were supported, in part, by grants 1UL1RR029893, R01DK090989, K23CA107123, R01GM63270 from the National Center for Research Resources, National Institutes of Health. Accordingly, the U.S. government may have certain rights in the invention.

FIELD OF THE INVENTION

The present invention relates to characterizing changes in mammalian gastrointestinal microbiota associated with antibiotic treatment and various disease conditions (such as obesity, metabolic syndrome, insulin-deficiency or insulin-resistance related disorders, glucose intolerance, diabetes, non-alcoholic fatty liver, abnormal lipid metabolism, short stature, osteoporosis and other disorders of bone formation and mineralization, etc.) and related diagnostic and therapeutic methods. Therapeutic methods of the invention involve the use of probiotics, prebiotics, or narrow spectrum antibiotics/antibacterial agents that are capable of restoring healthy mammalian bacterial gastrointestinal microbiota.

BACKGROUND OF THE INVENTION

Obesity has become widespread with increases in prevalence across all developed nations (Bouchard, C (2000) N Engl J. Med. 343, 1888-9). According to the Center for Disease Control (CDC), over 60% of the United States population is overweight, and greater than 30% are obese. For affected persons, the problem often begins in childhood, and continues for life. Major contributors are believed to be increased consumption of high calorie foods and a more sedentary life style. However, neither of these alone or together are sufficient to explain the rise in obesity and subsequent or concomitant obesity-related disorders, such as, e.g., type II diabetes mellitus, metabolic syndrome, hypertension, cardiac pathology, and non-alcoholic fatty liver disease. According to the National Institute of Diabetes, Digestive and Kidney Diseases (NIDDK) approximately 280,000 deaths annually are directly related to obesity. The NIDDK further estimated that the direct cost of healthcare in the U.S. associated with obesity is $51 billion. In addition, Americans spend $33 billion per year on weight loss products. The prevalence of obesity continues to rise at alarming rates.

It is estimated that between 20-25% of American adults (about 47 million) have metabolic syndrome, a complex condition associated with an increased risk of vascular disease. Metabolic syndrome is also known as Syndrome X, metabolic syndrome X, insulin resistance syndrome, or Reaven's syndrome. Metabolic syndrome is generally believed to be a combination of disorders that affect a large number of people in a clustered fashion. The symptoms and features of the syndrome include at least three of the following conditions: diabetes mellitus type II; impaired glucose tolerance or insulin resistance; high blood pressure; central obesity and difficulty losing weight; high cholesterol; combined hyperlipidemia; including elevated LDL; decreased HDL; elevated triglycerides; and fatty liver (especially in concurrent obesity). Insulin resistance is typical of metabolic syndrome and leads to several of its features, including glucose intolerance, dyslipidemia, and hypertension. Obesity is commonly associated with the syndrome as is increased abdominal girth, highlighting the fact that abnormal lipid metabolism likely contributes to the underlying pathophysiology of metabolic syndrome.

Metabolic syndrome was codified in the United States with the publication of the National Cholesterol Education Program Adult Treatment Panel III (ATP III) guidelines in 2001. On a physiologic basis, insulin resistance appears to be responsible for the syndrome. However, insulin resistance can be defined in a myriad of different ways, including impaired glucose metabolism (reduced clearance of glucose and/or the failure to suppress glucose production), the inability to suppress lipolysis in tissues, defective protein synthesis, altered cell differentiation, aberrant nitric oxide synthesis affecting regional blood flow, as well as abnormal cell cycle control and proliferation, all of which have been implicated in the cardiovascular disease associated with metabolic syndrome. At least at present, there is no obvious molecular mechanism causing the syndrome, probably because the condition represents a failure of one or more of the many compensatory mechanisms that are activated in response to energy excess and the accumulation of fat.

Individuals at risk for metabolic syndrome include those who exhibit central obesity with increased abdominal girth (due to excess visceral adiposity) of about more than 35 inches in women and more than 40 inches in men. Individuals at risk for metabolic syndrome also include those that have a BMI greater than or equal to 30 kg/M2 and may also have abnormal levels of nonfasting glucose, lipids, and blood pressure.

Although certain bacterial associations have been examined for these and related conditions, the role of bacterial microbiota in these conditions has not been clearly understood or appreciated. Thus, there remains a need for methods for diagnosing, treating and preventing conditions such as obesity, metabolic syndrome, insulin-deficiency or insulin-resistance related disorders, glucose intolerance, diabetes, non-alcoholic fatty liver, abnormal lipid metabolism, short stature, osteoporosis and other disorders of bone formation and mineralization, and related disorders.

The average human body, consisting of about $10^{13}$ cells, has about ten times that number of microorganisms. The $\sim 10^{14}$ microbes that live in and on each of our bodies belong to all three domains of life on earth—bacteria, archaea and eukarya. The major sites for our indigenous microbiota are the gastrointestinal tract, skin and mucosal surfaces such as nasal mucosa and vagina as well as the oropharynx. By far, the largest bacterial populations are in the colon. Bacteria make up most of the flora in the colon and 60% of the dry mass of feces. Probably more than 1000 different species live in the gut. However, it is probable that >90% of the bacteria come from less than 50 species. Fungi and protozoa also make up a part of the gut flora, but little is known about their activities. The skin also has a diverse microbiome, also with likely >1000 species, yet with major populations within a small number of species (Gao et al., Proc. Natl. Acad. Sci. USA 2007, 104(8):2927-2932). While the microbiota is highly extensive, it is barely characterized. Consequently, the Roadmap of the National Institutes of Health (NIH) includes the "Human Microbiome Project" to better characterize our microbial communities and the genes that they harbor (our microbiome) and better understand its relation to both human health and disease. Reviewed in Dethlefsen et al., Nature, 2007, 449:811-818; Turnbaugh et al., Nature, 2007, 449:804-810; Ley et al., Cell, 2006, 124:837-848.

Studies show that the relationship between gut flora and humans is not merely commensal (a non-harmful coexistence), but rather often is a mutualistic, symbiotic relationship. Although animals can survive with no gut flora, the microorganisms perform a host of useful functions, such as training the immune system, preventing growth of harmful species, regulating the development of the gut, fermenting unused energy substrates, metabolism of glycans and amino acids, synthesis of vitamins (such as biotin and vitamin K) and isoprenoids, biotransformation of xenobiotics, and producing hormones to direct the host to store fats. See, e.g., Gill et al., Science. 2006, 312:1355-1359; Zaneveld et al., Curr. Opin. Chem. Biol., 2008, 12(1):109-114; Guarner, Digestion, 2006, 73:5-12; Li et al., Proc. Natl. Acad. Sci. USA, 2008, 105: 2117-2122; Hooper, Trends Microbiol., 2004, 12:129-134; Mazmanian et al., Cell, 2005, 122:107-118; Rakoff-Nahoum et al., Cell, 2004, 118:229-241. It is therefore believed that changes in the composition of the gut microbiota could have important health effects (Dethlefsen et al., PLoS Biology, 2008, 6(11):2383-2400). Indeed, a correlation between obesity and changes in gut microbiota has been observed (Ley et al., Proc Natl Acad Sci USA, 2005; 102:11070-11075; Backhed et al., Proc Natl Acad Sci USA, 2004; 101:15718-15723). Furthermore, in certain conditions, some microbial species are thought to be capable of directly causing disease by causing infection or increasing cancer risk for the host (O'Keefe et al., J. Nutr. 2007; 137:175 S-182S; McGarr et al., J Clin Gastroenterol., 2005; 39:98-109).

Substantial number of species in vertebrate microbiota is very hard to culture and analyze via traditional cultivation-based studies (Turnbaugh et al., Nature, 2007, 449:804-810; Eckburg et al., Science, 2005, 308:1635-1638). In contrast, broad-range PCR primers targeted to highly conserved regions makes possible the amplification of small subunit rRNA gene (16S rDNA) sequences from all bacterial species (Zoetendal et al., (2006) *Mol Microbiol* 59, 1639-1650), and the extensive and rapidly growing 16S rDNA database facilitates identification of sequences to the species or genus level (Schloss and Handelsman, (2004) *Microbiol Mol Biol Rev* 68, 686-691). Such techniques can also be used for identifying bacterial species in complex environmental niches (Smit et al., (2001)*Appl Environ Microbiol* 67, 2284-2291), including the human mouth, esophagus, stomach, intestine, feces, skin, and vagina, and for clinical diagnosis (Harris and Hartley, (2003) *J Med Microbiol* 52, 685-691; Saglani et al., (2005) *Arch Dis Child* 90, 70-73).

Much of the microbiota is conserved from human to human, at least at the level of phylum and genus (for a general description of human microbiota see, e.g., Turnbaugh et al., Nature 2007; 449:804-810; Ley et al., Nature 2006; 444: 1022-1023; Gao et al., Proc Natl Acad Sci USA 2007; 104: 2927-32; Pei et al., Proc Natl Acad Sci USA 2004; 101:4250-4255; Eckburg et al., Science 2005; 308:1635-1638; Bik et al., Proc Natl Acad Sci USA 2006; 103:732-737). A major source of the human microbiota is from one's mother (for a summary of typical maternal colonization patterns see, e.g., Palmer et al., Plos Biology 2007; 5:e177; Raymond et al., Emerg Infect Dis 2004; 10:1816-21), and to a lesser extent from one's father and siblings (for examples of typical colonization patterns see, e.g., Raymond et al., Emerg Infect Dis 2004; 10:1816-21; Raymond et al., Plos One 2008; 3:e2259; Goodman et al., Am J Epidemiol 1996; 144:290-299; Goodman et al., Lancet 2000; 355:358-362). However, many of the natural mechanisms for the transmission of these indigenous organisms across generations and between family members have diminished with socioeconomic development. The impediments include: childbirth by caesarian section, reduced breast-feeding, smaller family size (fewer siblings), reduced household crowding with shared beds, utensils, indoor plumbing.

Effective antibiotics were discovered in the early-mid 20th century and came into wide use after World War II. Antibiotic use has increased dramatically with rates approximating one course of antibiotics per year in the average child in the USA (for a summary of US antibiotic courses in a year, see, e.g., McCaig et al., JAMA 2002; 287:3096-3102).

Antibiotic use places selective pressure on the microbiota, in particular selecting for the long-term persistence of resistant organisms (such persistence is described in Levy, Sci Am 1998; 278:46-53). Antibiotic resistance may be intrinsic or secondary to acquired genetic elements, but marker organisms (and genes) may be used to observe the phenomenon (examples of such markers may be found in, e.g., Sjölund et al., Annals of Internal Medicine 2003; 139: 483-487; Sjölund et al., Emerging Infectious Diseases 2005:11:1389-1393).

The acute effects of antibiotic treatment on the native gut microbiota range from self-limiting "functional" diarrhea to life-threatening pseudomembranous colitis (Beaugerie and Petit, Best Pract Res Clin Gastroenterol. 2004; 18:337-352; Wilcox, Best Pract Res Clin Gastroenterol. 2003; 17:475-493). The long-term consequences of such perturbations for the human-microbial symbiosis are more difficult to discern, but chronic conditions such as asthma and atopic disease have been associated with childhood antibiotic use and an altered intestinal microbiota (see, e.g., Marra et al.; Chest. 2006; 129:610-618; Noverr and Huffnagle, Clin Exp Allergy. 2005; 35:1511-1520; Prioult and Nagler-Anderson; Immunol Rev. 2005; 206:204-218; Kozyrskyj et al., Chest. 2007; 131:1753-9).

It has been known for more than 50 years that the administration of low doses of antibiotics promotes the growth of farm animals. As a result, the largest use of antibiotics and other antimicrobial substances is on the farm, where they are fed in low doses to large numbers of animals used for food production. Additionally, the following observations regarding antibiotic use are appreciated:

1. feeding low (subtherapeutic) doses of antimicrobials promotes weight gain (often 5-10% of total weight) of animals used for food production (See, e.g., Jukes, Bioscience 1972; 22: 526-534; Jukes (1955) Antibiotics in Nutrition. New York, N.Y., USA: Medical Encyclopedia; Feighner and Dashkevicz, Appl. Environ. Microbiol., 1987, 53: 331-336; McEwen and Fedorka-Cray, Clin. Infect. Dis., 2002, 34 (Suppl 3): S93-S106);
2. the effects are broad across vertebrate species, involving at least mammals (cattle, swine, sheep), and birds (chickens and turkeys);
3. the effects can be realized by oral administrations of the agents, suggesting that the microbiota of the gastrointestinal tract is a major target;
4. the effects are due to many different classes of antimicrobial agents (including macrolides, tetracyclines, penicillins);
5. anti-fungal agents do not produce the effect;
6. the effects can be observed at many different stages in the growth and development of young animals.

The mechanism for this widespread phenomenon has not been established but because of the activity of anti-bacterial but not anti-fungal agents, it can be ascertained to be anti-bacterial.

The vertebrate gastrointestinal tract has a rich component of cells involved in immune responses. The nature of the microbiota colonizing experimental animals or humans affects the immune responses of the populations of reactive host cells (see, e.g., Ando et al., Infection and Immunity 1998; 66:4742-4747; Goll et al., Helicobacter. 2007; 12:185-92; Lundgren et al., Infect Immun 2005; 73:523-531).

The vertebrate gastrointestinal tract also is a locus in which hormones are produced. In mammals, many of these hormones related to energy homeostasis (including insulin, glucagon, leptin, and ghrelin) are produced by organs of the gastrointestinal tract (see, e.g., Mix et al., Gut 2000; 47:481-6; Kojima et al., Nature 1999; 402:656-60; Shak et al., Obesity Surgery 2008; 18(9):1089-96; Roper et al., Journal of Clinical Endocrinology & Metabolism 2008; 93:2350-7; Francois et al., Gut 2008; 57:16-24; Cummings and Overduin, Clin Invest 2007; 117:13-23; Bado et al., Nature 1998; 394:790-793).

Changing of the microbiota of the gastrointestinal tract appears to affect the levels of some of these hormones (see, e.g., Breidert et al., Scand J Gastroenterol 1999; 34:954-61; Liew et al., Obes. Surg. 2006; 16:612-9; Nwokolo et al., Gut. 2003; 52, 637-640; Kinkhabwala et al., Gastroenterology 132:A208). The hormones affect immune responses (see, e.g., Matarese et al., J Immunol 2005; 174:3137-3142; Matsuda et al., J. Allergy Clin. Immunol. 2007; 119, S174) and adiposity (see, e.g., Tschop et al., Nature 2000; 407:908-13).

SUMMARY OF THE INVENTION

As specified in the Background section above, there is a great need in the art (i) to understand the impact that mammalian bacterial microbiota has on the host health and (ii) to employ such knowledge in development of new therapeutics. There is further a great need in the art to treat such diseases as obesity, metabolic syndrome, insulin-deficiency or insulin-resistance related disorders, glucose intolerance, diabetes, non-alcoholic fatty liver, abnormal lipid metabolism, short stature, osteoporosis and other disorders of bone formation and mineralization, and related disorders.

The present invention addresses these and other needs by characterizing specific changes in mammalian bacterial microbiota associated with antibiotic treatment and specific diseases and related diagnostic and therapeutic methods.

In one aspect, the invention provides a method of treating a disease in a mammal (e.g., human) comprising administering to the mammal a therapeutically effective amount of a probiotic composition comprising one or more bacterial strains, wherein the composition (i) stimulates growth or activity of one or more bacterial taxa (e.g., species) which are under-represented in microbiota (e.g., gastrointestinal microbiota) of the mammal as compared to a healthy control or (ii) inhibits growth or activity of one or more bacterial taxa (e.g., species) which are over-represented in microbiota (e.g., gastrointestinal microbiota) of the mammal as compared to a healthy control.

In another aspect, the invention provides a method for treating a disease associated with antibiotic treatment in a mammal (e.g., human) comprising (i) stimulating growth or activity of one or more bacterial taxa (e.g., species) which have been depleted in microbiota (e.g., gastrointestinal microbiota) of the mammal as a result of antibiotic treatment of the mammal or (ii) inhibiting growth or activity of one or more bacterial taxa (e.g., species) which are over-represented in microbiota (e.g., gastrointestinal microbiota) of the mammal as a result of antibiotic treatment of the mammal. In one specific embodiment, such method comprises inhibiting growth or activity of one or more species of Lachnospiraceae. In one embodiment, the method comprises administering a therapeutically effective amount of a probiotic composition comprising one or more bacterial strains which have been depleted as a result of antibiotic treatment.

In a further aspect, the invention provides a method for restoring at least one bacterial taxa (e.g., species) depleted as a result of antibiotic treatment or disease in a mammal (e.g., human) comprising a) identifying under-represented bacterial taxa in an antibiotic-treated or diseased microbiota (e.g., gastrointestinal microbiota) sample from the mammal as compared to a healthy control; b) culturing the identified under-represented bacteria from step a); and c) administering the bacterial inoculant(s) from step b) to the mammal, wherein the inoculant(s) increases growth of the under-represented bacteria in the mammal.

In yet another aspect, the invention provides a method of treating a disease in a mammal (e.g., human), wherein said disease is associated with a change in microbiota (e.g., gastrointestinal microbiota) of the mammal as compared to a healthy control, comprising administering to the mammal a therapeutically effective amount of a narrow spectrum antibiotic or another anti-bacterial agent to inhibit growth or activity of one or more bacterial taxa (e.g., species) which are over-represented in the microbiota of the mammal as compared to the healthy control. In one embodiment, the method comprises identifying over-represented bacterial taxa in the diseased microbiota sample from the mammal as compared to the healthy control.

Non-limiting examples of methods useful for identifying over- and under-represented bacterial taxa (e.g., species) in any of the methods of the invention include, e.g., screening bacterial 16S rRNA genes using PCR, high-throughput sequencing or PCR methods which detect over- and under-represented genes in the total bacterial population, and transciptomic or proteomic studies that identify lost or gained microbial transcripts or proteins within total bacterial populations.

Non-limiting examples of bacterial strains contained in the probiotic compositions useful in the methods of the invention include live bacterial strains and conditionally lethal bacterial strains. In one embodiment, the bacterial strain contained in the probiotic composition is an *H. pylori* strain. Useful probiotic compositions can further comprise a buffering agent (such as e.g., sodium bicarbonate, milk, yogurt, or infant formula). In one embodiment, the probiotic compositions of the invention are administered orally.

In one embodiment, the healthy control useful in the methods of the invention is a healthy subject of the same age, gender and enterotype as the mammal being treated or an average of several such subjects. If the mammal is human, a useful healthy control can be a healthy human of the same age, gender and ethnicity as the human being treated or an average of several such healthy subjects.

Non-limiting examples of diseases treatable by the methods of the present invention include, e.g., obesity, metabolic syndrome, insulin-deficiency, insulin-resistance related disorders, glucose intolerance, diabetes, non-alcoholic fatty liver, abnormal lipid metabolism, short stature, osteoporosis, and other disorders of bone formation and mineralization.

In one embodiment, the invention provides a method for increasing adult height or muscle mass in a mammal (e.g., human) in need thereof comprising (i) stimulating growth or activity of one or more bacterial taxa (e.g., species) which is over-represented in microbiota (e.g., gastrointestinal microbiota) of the mammal as a result of treatment with a sub-therapeutic concentration of an antibiotic early in life or (ii) inhibiting growth or activity of one or more bacterial taxa (e.g., species) which is depleted in microbiota (e.g., gastrointestinal microbiota) of the mammal as a result of treatment with a sub-therapeutic concentration of an antibiotic early in life. In one specific embodiment, this method comprises identifying over-represented or depleted bacterial taxa (e.g., species) in the microbiota from the mammal as compared to a healthy control.

In a separate embodiment, the invention provides a method for increasing adult height or muscle mass in a mammal in need thereof comprising administering to the mammal a sub-therapeutic concentration of an antibiotic early in life.

BRIEF DESCRIPTION OF THE DRAWINGS

FIGS. 3A-H demonstrate growth dynamics of control and sub-therapeutic antibiotic-treated (STAT) C57BL6/J F1 generation mice. One group of sub-therapeutic penicillin-treated (STPT) mice received antibiotics at day 0 of life (at birth) (males n=5, females n=4) and a second group of STPT mice received antibiotics at day 28 of life upon weaning (males n=5, females n=6). Both groups received continuous antibiotic exposure through their drinking water until sacrifice at 20 weeks of age. Control mice (males n=6, females n=5) were not exposed to antibiotics. Panels: A) and B) growth curve; and C) and D) weight gain fit with Boltzmann curve, $R^2>0.9$ for all groups; E) and F) linear regression for weight gain in $4^{th}$ week of life for male and female mice; G) growth rate (g/day) and $R^2$ for week 3 of life; H) growth rate in $4^{th}$ week of life, ***$P<0.0005$, t-test.

FIGS. 9A-H show growth dynamics of control and STPT mice, exposed at birth, from F1 generation, litter 2. Sub-therapeutic penicillin-treated (STPT) C57BL6/J mice received antibiotics at day 0 of life (at birth) continuously through their drinking water (males n=10, females n=18). Control mice were not exposed to antibiotics (males n=5, females n=13). Growth curves (Panels A and B). Weight gain fit with Boltzmann curve, $R2>0.9$ for all groups (Panels C and D). Linear regression for weight gain during early development (Panels E and F). Growth rate (g/day) and R2 during early development (Panel G) Growth rate measured from day 22 to 31***$P<0.0005$, t-test (Panel H).

DETAILED DESCRIPTION OF THE INVENTION

Figure 1:
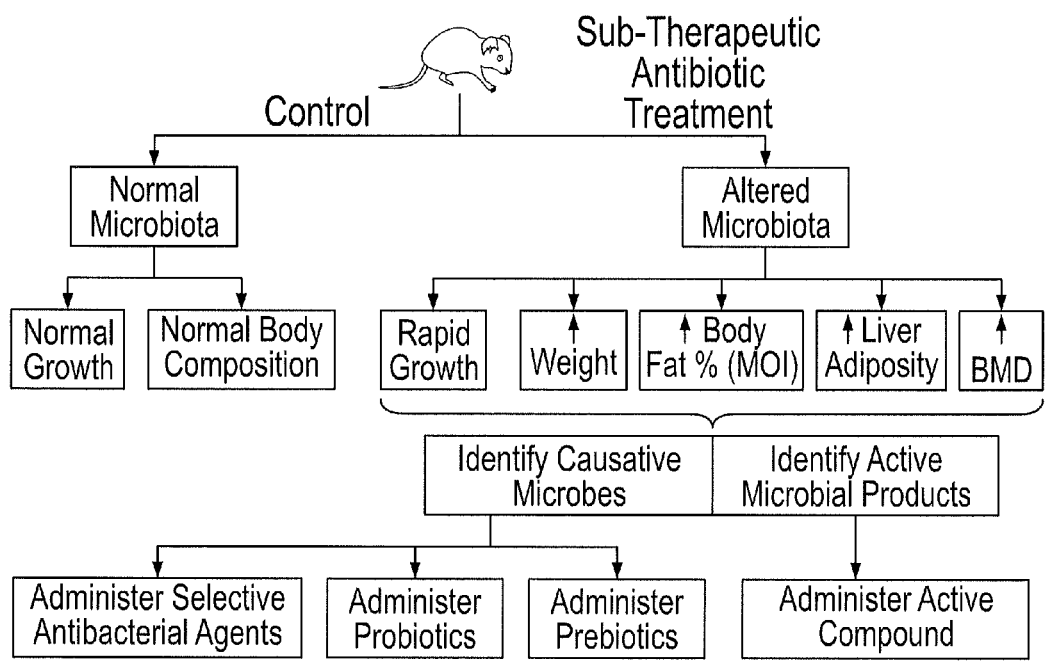
FIG. 1 is a schematic of the design of Microbial Induced Obesity (MIO) experiments, key findings, and applications.

The present invention is based on an unexpected experimental observation in a mouse model that (low-dose) sub-therapeutic antibiotic treatment (STAT) changes growth rate early in life, and alters body composition later in life. The invention further provides the use of microbe induced obesity (MIO) models to identify key microorganisms that alter host metabolism and development, and thus provides new approaches to prevent and treat obesity, metabolic syndrome, insulin-deficiency or insulin-resistance related disorders, glucose intolerance, diabetes, non-alcoholic fatty liver, abnormal lipid metabolism, short stature, osteoporosis and other disorders of bone formation and mineralization, and related disorders.

While not wishing to be bound by any particular theory, it is believed that changes in gastrointestinal bacteria cause the above diseases by affecting both immunological and hormonal functions of the host, which, in turn, affect the balance of energy consumption and storage and/or immunological homeostasis between tolerance and sensitization.

The present invention also provides therapeutic methods for treating obesity, metabolic syndrome, insulin-deficiency or insulin-resistance related disorders, glucose intolerance, diabetes (such as type II diabetes mellitus), non-alcoholic fatty liver, abnormal lipid metabolism, short stature, osteoporosis and other disorders of bone formation and mineralization, and related disorders by restoring mammalian bacterial gastrointestinal microbiota to the composition observed in healthy subjects. In a more general aspect, the present invention provides a method for treating various diseases associated with changes in gastrointestinal microbiota by restoring such microbiota to the composition observed in healthy subjects.

Definitions and Abbreviations

As used herein, the term "bacteria" encompasses both prokaryotic organisms and archaea present in mammalian microbiota.

The terms "intestinal microbiota", "gut flora", and "gastrointestinal microbiota" are used interchangeably to refer to bacteria in the digestive tract.

As used herein, the term "probiotic" refers to a substantially pure bacteria (i.e., a single isolate), or a mixture of desired bacteria, and may also include any additional components that can be administered to a mammal for restoring microbiota. Such compositions are also referred to herein as a "bacterial inoculant." Probiotics or bacterial inoculant compositions of the invention are preferably administered with a buffering agent to allow the bacteria to survive in the acidic environment of the stomach, i.e., to resist low pH and to grow in the intestinal environment. Such buffering agents include sodium bicarbonate, milk, yogurt, infant formula, and other dairy products.

As used herein, the term "prebiotic" refers to an agent that increases the number and/or activity of one or more desired bacteria. Non-limiting examples of prebiotics useful in the methods of the present invention include fructooligosaccharides (e.g., oligofructose, inulin, inulin-type fructans), galactooligosaccharides, amino acids, alcohols, and mixtures thereof. See, e.g., Ramirez-Farias et al., Br J Nutr (2008) 4:1-10; Pool-Zobel and Sauer, J Nutr (2007), 137:2580 S-2584S.

As used herein, the term "metagenome" refers to genomic material obtained directly from a subject, instead of from culture. Metagenome is thus composed of microbial and host components.

The terms "treat" or "treatment" of a state, disorder or condition include:
(1) preventing or delaying the appearance of at least one clinical or sub-clinical symptom of the state, disorder or condition developing in a subject that may be afflicted with or predisposed to the state, disorder or condition but does not yet experience or display clinical or subclinical symptoms of the state, disorder or condition; or
(2) inhibiting the state, disorder or condition, i.e., arresting, reducing or delaying the development of the disease or a relapse thereof (in case of maintenance treatment) or at least one clinical or sub-clinical symptom thereof; or
(3) relieving the disease, i.e., causing regression of the state, disorder or condition or at least one of its clinical or sub-clinical symptoms.

The benefit to a subject to be treated is either statistically significant or at least perceptible to the patient or to the physician.

As used herein, the term "early in life" refers to the period in life of a mammal before growth and development is complete. In case of humans, this term refers to pre-puberty, preferably within the first 6 years of life.

A "therapeutically effective amount" means the amount of a bacterial inoculant or a compound (e.g., a narrow spectrum antibiotic or anti-bacterial agent) that, when administered to a subject for treating a state, disorder or condition, is sufficient to effect such treatment. The "therapeutically effective amount" will vary depending on the compound, bacteria or analogue administered as well as the disease and its severity and the age, weight, physical condition and responsiveness of the mammal to be treated.

The term "sub-therapeutic antibiotic treatment" refers to administration of an amount of an antibiotic that will not produce therapeutically effective levels of such antibiotic in the bloodstream (for systemic administration) or at the site of administration (for local administration). Non-limiting examples of pediatric systemic therapeutic dosages for commonly used antibiotics include, e.g., 25-50 mg/kg/day for penicillin, 40-60 mg/kg/day for vancomycin, and 25-50 mg/kg/day for tetracycline. See, e.g., Nelson's Pocket Book of Pediatric Antimicrobial Therapy, 2002-2003, 15$^{th}$ Ed. J. Bradley & J. Nelson, eds., Lippincott Williams and Wilkins. Preferably, according to the methods of the present invention, the sub-therapeutic antibiotic treatment refers to antibiotic doses of 1-5 mg/kg/day.

The term "narrow spectrum antibiotic" is an antibiotic which can selectively inhibit growth and/or activity of one or few bacterial species or taxa. Non-limiting examples of such antibiotics are lysostaphin for *S. aureus* and cholestyramine for *Clostridium difficile*.

As used herein, the phrase "pharmaceutically acceptable" refers to molecular entities and compositions that are generally regarded as physiologically tolerable.

As used herein, the term "combination" of a bacterial inoculant, probiotic, analogue, or prebiotic compound and at least a second pharmaceutically active ingredient means at least two, but any desired combination of compounds can be delivered simultaneously or sequentially (i.e., within a 24 hour period).

"Patient" or "subject" as used herein refers to mammals and includes human and veterinary animals.

The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Alternatively, the carrier can be a solid dosage form carrier, including but not limited to one or more of a binder (for compressed pills), a glidant, an encapsulating agent, a flavorant, and a colorant. Suitable pharmaceutical carriers are described in "Remington's Pharmaceutical Sciences" by E. W. Martin.

Diagnostic Methods of the Invention

In one aspect, the present invention characterizes specific changes in mammalian bacterial gastrointestinal microbiota which occur upon treatment with sub-therapeutic doses of antibiotics, wherein such treatment is associated with at least one of (i) increased % body fat and adipose tissue deposition and (ii) increased bone mineral density (BMD) at early stages of life. Such specific antibiotic and/or obesity- and/or BMD-associated changes in mammalian bacterial gastrointestinal microbiota disclosed herein constitute diagnostics which can be used to determine whether a given mammal is likely to develop obesity and/or short stature.

Specific changes in microbiota can be detected using various methods, including without limitation quantitative PCR or high-throughput sequencing methods which detect over- and under-represented genes in the total bacterial population (e.g., 454-sequencing for community analysis), or transcriptomic or proteomic studies that identify lost or gained microbial transcripts or proteins within total bacterial populations. See, e.g., Eckburg et al., Science, 2005, 308:1635-8; Costello et al., Science, 2009, 326:1694-7; Grice et al., Science, 2009, 324:1190-2; Li et al., Nature, 2010, 464: 59-65; Bjursell et al., Journal of Biological Chemistry, 2006, 281:36269-36279; Mahowald et al., PNAS, 2009, 14:5859-5864; Wikoff et al., PNAS, 2009, 10:3698-3703. For example, as disclosed by the inventors and co-workers in US Patent Publication No. 2010/0074872, such changes can be also detected by screening for a ratio of the phyla Bacteroidetes to Firmicutes (B/F ratio) in mammalian bacterial gastrointestinal microbiota. B/F ratio can be determined, for example, by determining the ratio of bacterial genomic sequences corresponding to each phyla using such methods as (i) screening of microbial 16S ribosomal RNAs (16S rRNA) using PCR and/or (ii) high-throughput sequencing.

Therapeutic Methods of the Invention

In conjunction with the diagnostic methods, the present invention also provides therapeutic methods for treating obesity, metabolic syndrome, insulin-deficiency or insulin-resistance related disorders, glucose intolerance, diabetes (such as type II diabetes mellitus), non-alcoholic fatty liver, abnormal lipid metabolism, short stature, osteoporosis and other disorders of bone formation and mineralization, and related disorders by restoring mammalian bacterial gastrointestinal microbiota to the composition observed in healthy subjects.

In a more general aspect, the present invention provides a method for treating various diseases associated with changes in gastrointestinal microbiota by restoring such microbiota to the composition observed in healthy subjects.

In certain specific embodiments, restoring of microbiota is achieved by administering to a mammal in need thereof a therapeutically effective amount of a probiotic composition comprising an effective amount of at least one bacterial strain, or a combinations of several strains, wherein the composition (i) stimulates or inhibits specific metabolic pathways involved in host energy homeostasis and/or (ii) stimulates growth and/or activity of bacteria which are under-represented in a disease and/or (iii) inhibits growth and/or activity of bacteria which are over-represented in a disease.

Bacterial strains administered according to the methods of the present invention can comprise live bacteria. One or several different bacterial inoculants can be administered simultaneously or sequentially (including administering at different times). Such bacteria can be isolated from microbiota and grown in culture using known techniques. However, many bacterial species are very difficult to culture and administration of others (like *H. pylori*) may lead to various undesirable side-effects. The present invention therefore comprises administering "bacterial analogues", such as recombinant carrier strains expressing one or more heterologous genes derived from the bacteria affected in a disease. The use of such recombinant bacteria may allow the use of lower therapeutic amounts due to higher protein expression and may simultaneously allow to avoid any potential harmful side-effects associated with reintroduction of specific bacterial strains. Non-limiting examples of recombinant carrier strains useful in the methods of the present invention include *E. coli* and *Lactobacillus* (e.g., *E. coli* and *Lactobacillus* expressing cag island-encoded type IV secretion system of *H. pylori*). Methods describing the use of bacteria for heterologous protein delivery are described, e.g., in U.S. Pat. No. 6,803,231.

In certain embodiments, a conditional lethal bacterial strain can be utilized as the inoculant or to deliver a recombinant construct. Such a conditional lethal bacteria survives for a limited time typically when provided certain nutritional supplements. It is contemplated that such a supplement could be a liquid, formulated to contain the nutritional component necessary to keep the bacteria alive. It is further contemplated that a patient/subject would drink such a supplement in intervals to keep the bacteria alive. Once the supplement is depleted, the conditional lethal bacteria dies. Methods relating to conditional lethal strains of *H. pylori* are described in U.S. Pat. No. 6,570,004.

In certain embodiments, the bacterial inoculant used in the methods of the invention further comprises a buffering agent. Examples of useful buffering agents include sodium bicarbonate, milk, yogurt, infant formula, and other dairy products.

Administration of a bacterial inoculant can be accomplished by any method likely to introduce the organisms into the desired location. The bacteria can be mixed with a carrier and (for easier delivery to the digestive tract) applied to liquid or solid food, or feed or to drinking water. The carrier material should be non-toxic to the bacteria and the subject/patient. Preferably, the carrier contains an ingredient that promotes viability of the bacteria during storage. The formulation can include added ingredients to improve palatability, improve shelf-life, impart nutritional benefits, and the like. If a reproducible and measured dose is desired, the bacteria can be administered by a rumen cannula.

The dosage of the bacterial inoculant or compound of the invention will vary widely, depending upon the nature of the disease, the patient's medical history, the frequency of administration, the manner of administration, the clearance of the agent from the host, and the like. The initial dose may be larger, followed by smaller maintenance doses. The dose may be administered as infrequently as weekly or biweekly, or fractionated into smaller doses and administered daily, semi-weekly, etc., to maintain an effective dosage level. It is contemplated that a variety of doses will be effective to achieve colonization of the gastrointestinal tract with the desired bacterial inoculant, e.g. $10^6$, $10^7$, $10^8$, $10^9$, and $10^{10}$ CFU for example, can be administered in a single dose. Lower doses can also be effective, e.g., $10^4$, and $10^5$ CFU.

In certain embodiments, the present invention relates to a method for restoring mammalian bacterial gastrointestinal microbiota comprising administering to a mammal in need of such treatment, an effective amount of at least one gastric, esophageal, or colonic bacteria, or combinations thereof. In a preferred embodiment, the bacteria is administered orally. Alternatively, bacteria can be administered rectally or by enema.

One of the organisms contemplated for administration to restore the gastrointestinal microbiota is *Helicobacter pylori*. *H. pylori* is Gram-negative, microaerophilic, fastidious bacterium that colonizes specifically the surface of the mucosa of the stomach. Non-limiting examples of *H. pylori* strains useful in the methods of the invention include live or conditionally lethal cagA positive (cagA+) strains (i.e., strains possessing a full functioning cag island-encoded type IV secretion system that can inject the CagA protein and other *H. pylori* constituents into epithelial cell), live or conditionally lethal cagA negative (cagA−) strains, as well as live or conditionally lethal strains varying in VacA activity (of genotypes s1 or s2, m1 or m2, i1 or i2) and/or in expression of the type I or type II Lewis antigen pathways. In certain embodiments, the bacteria administered in the therapeutic methods of the invention comprise *H. pylori* and one or more additional bacterial strains (such as, e.g., *Oxalobacter* species, *Lactobacillus* species, etc.). In one embodiment, the invention provides a method for treating asthma, allergy, gastrointestinal reflux disease (GERD), eosinophilic esophagitis, and related disorders in a mammal comprising administering to the mammal a therapeutically effective amount of *H. pylori* live or conditionally lethal cagA positive (cagA+) strain.

In certain embodiments, the probiotic composition of the invention comprises a therapeutically effective amount of at least one bacterial strain, or combinations of several strains, wherein the composition inhibits the growth of antibiotic-resistant bacteria. In a specific embodiment, such composition comprises one or several antibiotic-sensitive bacterial strains which have been diminished or lost as a result of antibiotic treatment. In one embodiment, such antibiotic-sensitive bacteria are capable of competing with antibiotic-resistant bacteria that facilitate calorie uptake in the gut and in this way lower weight gain by the host and treat obesity, metabolic syndrome, diabetes, and related disorders. In another embodiment, such antibiotic-sensitive bacteria are capable of competing with antibiotic-resistant bacteria and facilitate T regulatory responses in gastric and/or intestinal tissue and in this way treat asthma, allergy, and related disorders (e.g., eczema, allergic rhinitis, etc.).

In certain other specific embodiments, the therapeutic methods of the invention rely on the administration of a therapeutically effective amount of a prebiotic agent or a combination of such agents that (i) increase the number and/or activity of one or more bacteria which are under-represented in a disease and/or (ii) decrease the number and/or activity of one or more bacteria which are over-represented in a disease. Non-limiting examples of prebiotic agents useful in the methods of the present invention include fructooligosaccharides (e.g., oligofructose, inulin, inulin-type fructans), galactooligosaccharides, amino acids, alcohols, and mixtures thereof. Additional prebiotic agents can be selected based on the knowledge of a particular microbiota-affected host metabolic pathway and/or immunological response implicated in a disease to be treated.

In certain other specific embodiments, the therapeutic methods of the invention rely on the administration of a therapeutically effective amount of a naturally or recombinantly produced bacterial protein or a combination of such proteins which (i) increase the number and/or activity of one or more bacteria which are under-represented in a disease and/or (ii) decrease the number and/or activity of one or more bacteria which are over-represented in a disease. The proteins according to this embodiment may be produced by the same strain of bacteria which is intended to be regulated or by a different strain.

Pharmaceutical Compositions

While it is possible to use a bacterial inoculant or compound of the present invention for therapy as is, it may be preferable to administer it in a pharmaceutical formulation, e.g., in admixture with a suitable pharmaceutical excipient, diluent or carrier selected with regard to the intended route of administration and standard pharmaceutical practice. The excipient, diluent and/or carrier must be "acceptable" in the sense of being compatible with the other ingredients of the formulation and not deleterious to the recipient thereof. Acceptable excipients, diluents, and carriers for therapeutic use are well known in the pharmaceutical art, and are described, for example, in Remington: The Science and Practice of Pharmacy. Lippincott Williams & Wilkins (A. R. Gennaro edit. 2005). The choice of pharmaceutical excipient, diluent, and carrier can be selected with regard to the intended route of administration and standard pharmaceutical practice.

Although there are no physical limitations to delivery of the formulations of the present invention, oral delivery is preferred for delivery to the digestive tract because of its ease and convenience, and because oral formulations readily accommodate additional mixtures, such as milk, yogurt, and infant formula. For delivery to colon, bacteria can be also administered rectally or by enema.

Combination Treatments

For an enhanced therapeutic effect, the bacterial inoculants or compounds as described herein can be administered in combination with other therapeutic agents or regimes as discussed. The choice of therapeutic agents that can be co-administered with the bacterial inoculants or compounds of the invention depends, in part, on the condition being treated.

Non-limiting examples of additional pharmaceutically active compounds useful for treatment of obesity, metabolic syndrome, insulin-deficiency or insulin-resistance related disorders, glucose intolerance, diabetes (such as type II diabetes mellitus), non-alcoholic fatty liver, abnormal lipid metabolism, short stature, osteoporosis and other disorders of bone formation and mineralization, and related disorders include anti-inflammatory agents, antioxidants, antiarrhythmics, cytokines, analgesics, vasodilators, antihypertensive agents including beta-blockers, angiotensin converting enzyme inhibitors (ACE inhibitors), and calcium channel blockers, inhibitors of cholesterol synthesis, antithrombotic agents, and diabetes drugs.

Examples of inhibitors of cholesterol synthesis or absorption which are useful in the combination therapies of the present invention include Hmg-CoA reductase inhibitors and their bio-active metabolites, such as, e.g., simvastatin, lovastatin, pravastatin, compactin, fluvastatin, dalvastatin, atorvastatin, HR-780, GR-95030, CI-981, BMY 22089, and BMY 22566. See, e.g., U.S. Pat. Nos. 4,346,227; 4,444,784; 4,857,522; 5,190,970; 5,316,765, and 5,461,039; PCT Publ. No. WO84/02131; GB Pat. No. 2,202,846. As used in the methods or compositions of the present invention, any one or several of the Hmg-CoA reductase inhibitor compounds may be mixed with L-arginine or a substrate precursor to endogenous nitric oxide, as described in U.S. Pat. Nos. 6,425,881 and 6,239,172, and 5,968,983, to provide a therapeutically effective mixture for use in conjunction with compounds of the present invention.

Non-limiting examples of diabetes drugs useful in the combination therapies of the present invention include insulin, proinsulin, insulin analogs, activin, glucagon, somatostatin, amylin, actos (pioglitazone), amaryl (glimepiride), glipizide, avandia (rosiglitazone), glucophage, glucotrol, glucovance (a combination of glyburide and metformin), and the like. See, e.g., U.S. Pat. No. 6,610,272. The term "insulin" encompasses natural extracted human insulin, recombinantly produced human insulin, insulin extracted from bovine and/or porcine sources, recombinantly produced porcine and bovine insulin and mixtures of any of these insulin products. In accordance with the present invention, administering a bacterial inoculant or compound of the present invention in combination with insulin is expected to lower the dose of insulin required to manage the diabetic patient, while also alleviating the symptoms of metabolic syndrome.

In accordance with the present invention there may be numerous tools and techniques within the skill of the art, such as those commonly used in molecular immunology, cellular immunology, pharmacology, and microbiology. Such tools and techniques are describe in detail in e.g., Sambrook et al. (2001) Molecular Cloning: A Laboratory Manual. 3rd ed. Cold Spring Harbor Laboratory Press: Cold Spring Harbor, N.Y.; Ausubel et al. eds. (2005) Current Protocols in Molecular Biology. John Wiley and Sons, Inc.: Hoboken, N.J.; Bonifacino et al. eds. (2005) Current Protocols in Cell Biology. John Wiley and Sons, Inc.: Hoboken, N.J.; Coligan et al. eds. (2005) Current Protocols in Immunology, John Wiley and Sons, Inc.: Hoboken, N.J.; Coico et al. eds. (2005) Current Protocols in Microbiology, John Wiley and Sons, Inc.: Hoboken, N.J.; Coligan et al. eds. (2005) Current Protocols in Protein Science, John Wiley and Sons, Inc.: Hoboken, N.J.; and Enna et al. eds. (2005) Current Protocols in Pharmacology, John Wiley and Sons, Inc.: Hoboken, N.J.

Examples

The present invention is also described and demonstrated by way of the following examples. However, the use of these and other examples anywhere in the specification is illustrative only and in no way limits the scope and meaning of the invention or of any exemplified term. Likewise, the invention is not limited to any particular preferred embodiments described here. Indeed, many modifications and variations of the invention may be apparent to those skilled in the art upon reading this specification, and such variations can be made without departing from the invention in spirit or in scope. The invention is therefore to be limited only by the terms of the appended claims along with the full scope of equivalents to which those claims are entitled.

Materials and Methods:
Sub-Therapeutic Antibiotic Treatment (STAT)

Low dose penicillin (6.67 mg/L) was administered in the drinking water of C57BL6/J mice either at birth (day 0, antibiotics initially received through maternal milk) or at weaning (day 28); control mice received no antibiotics. All mice were given ad libitum access to food and water, and mice were fed either standard chow (13.5% kcal from fat) or high fat diet (45% kcal from fat). Mice were weighed daily and body composition was analyzed by dual energy x-ray absorptiometry (DEXA) and magnetic resonance imaging (MRI.)

Breeding

C57B6 breeder mice (F0) were obtained at 6 weeks of age from Jackson Laboratory. One male was mated with 2 females to create the F1 generation. Males and females were separated after pregnancy was detected. On day 14 of pregnancy, STAT breeder females were exposed to penicillin so that their offspring would be exposed to antibiotics from birth; control breeders had no antibiotic exposure. From the F1 generation, penicillin-treated and control mice at or near the median weight of their group were selected at 12 weeks of age to become breeders, and to produce the F2 generation. Breeder mice and offspring were maintained on their current treatment (either control or penicillin). (For breeding scheme study design, see FIG. 2).

Litter Care

The litters were monitored closely and the following information was collected: mating pairs, date of birth, litter number, number born, number weaned, animal number, gender, and generation number. Each of the mothers and the pups were visually observed on a daily basis and weighed 3 times/week on a standardized scale. When the mice were weaned on day 28, the mothers were removed from the cages and the pups were cared for as described in the existing protocol. The mothers were placed in separate cages for further breeding.

Dual Energy X-Ray Absortiometry (DEXA)

Mice were anesthetized using isofluorane. Total body mass, lean mass, fat mass, body fat percentage, and bone mineral density were measured using the Lunar PIXImus densitometer. The head was excluded from calculations to account for differences in mouse position.

MRI

Mice were anaesthetized with isofluorane. Body temperature and breathing rate were continuously monitored throughout the scan, and body temperature was maintained by flowing warm air through the coil. Mice were scanned with a 7 tesla magnet and the fat and water images were separated based on chemical shift properties using the Dixon IDEAL method. Total body fat percentage was calculated by merging the two images to generate a fat fraction image. To measure total abdominal fat, visceral abdominal fat, and subcutaneous abdominal fat volume, the abdominal wall was traced in 3 consecutive transverse abdominal slices midway between the kidney and hindlegs, creating a 3-dimensional volume of interest (VOI). The fat volume was calculated by multiplying total volume of the VOI by the mean fat %. To determine liver adiposity, 5 consecutive slices of the liver were traced to generate a liver VOI, and the average percent fat was recorded. Image processing was done using MRIcron software.

Glucose Tolerance Test

C57BL6 mice were fasted for 12 hours. Blood was collected from the tail and baseline glucose was measured using a glucometer. Glucose at a dose of 2 mg per gram of body weight was injected into the peritoneal cavity, and blood glucose levels were measured at 30, 60, and 120 minutes.

Fasting Insulin Measurement

C57BL6 mice were fasted for 12 hours and 100-200 µL of blood was collected by submandibular puncture. Serum was separated by centrifugation and stored at −80° C. Insulin levels were measured by Luminex detection method in the MILLIPLEX Mouse Gut Hormone Panel (Millipore, Billerica, Mass.).

DNA Extraction

DNA extractions from cecal contents and fecal pellets were performed using the Qiagen QIAmp DNA stool extraction kit (Qiagen, Germantown Md.) per the manufacturer's protocol. Total extracted DNA was quantified using a Nanodrop 1000 (Thermo Scientific, Waltham Mass.). PCR to confirm bacterial DNA extractions was performed using the 8F/1510R bacterial primers for 16S rRNA (Christine et al., Appl Environ Microbiol 68, 219-226 (2002); Martinez-Murcia et al., FEMS Microbiol Ecol 17, 247-256 (1995)).

Quantitative PCR Amplification

After genomic DNA extraction and quantification, samples were prepared for amplification and sequencing at the JCVI Joint Technology Center (JTC). Genomic DNA sample concentrations were normalized to ~5-10 ng/µl. The V3 region of the 16S rRNA gene was amplified using forward primer 341F (5'-CCTACGGGAGGCAGCAG-3' SEQ ID NO: 1) and reverse primer 534R (5'-ATTACCGCGGCTGCTGG-3' SEQ ID NO: 2) to which a 'CG' on the 5' end of the primer followed by symmetrical 10 nt barcodes were included as part of the primer design (5'-CGN(10)+16S primer-3'). Barcoded primer designs were completed using a set of algorithms developed at the JCVI. This design allowed for the inclusion of a unique barcode to each sample at the time of PCR so that the tagged samples could be multiplexed for sequencing. A total of 96 barcodes were used. Every effort was made to prevent contamination of PCR reactions with exogenous DNA including a set of reactions in a laminar flow hood. PCR reactions were completed as follows (per reaction): 1 µL of gDNA, 1× final concentration of Accuprime PCR Buffer II (Invitrogen, Carlsbad, Calif.), 250 mM Betaine, 200 nM forward and reverse primers, 0.5 units of Accuprime Taq DNA Polymerase High Fidelity (Invitrogen, Carlsbad, Calif., USA), and nuclease-free water to bring the final volume to 10 µL. PCR cycling conditions were: initial denaturation of 2 minutes at 95° C. followed by 25 cycles of 10 seconds at 95° C., 20 seconds at 63° C., and 30 seconds at 72° C. A negative control (water blank) reaction also was included and examined after 30 cycles. PCR reactions were visualized on 1% agarose gels and quantified using a Tecan SpectraFluor Plus (Tecan Group Ltd., Mannedorf, Switzerland) prior to normalization and pooling of samples for sequencing.

Hepatic Gene Expression Profiling and Data Analysis

Total DNA and total RNA was extracted from the mouse liver by the Wizard® Genomic DNA purification Kit (Promega) and RNeasy Mini Kit (Qiagen), respectively, according to the manufacturers instructions. Total RNA was reverse transcribed to cDNA using the Verso™ cDNA Synthesis Kit (Thermo Scientific). To generate standards for each target gene expression analysis, the DNA or cDNA region of interest was PCR-amplified and the PCR product was cloned using the pGEM-Teasy vector system (Promega). qPCR was performed with a LightCycler 480 SYBR Green I Master (Roche) and run in a LightCycler 480 system (Roche). Target mRNA was normalized to GAPDH mRNA as an internal control in each sample.

Expression profiling of the STAT and control animal groups (n=6 each) was performed using the Affymetrix Genechip system (Affymetrix, Santa Clara, Calif.). Total RNA quality and quantity were determined using the Agilent 2100

Bioanalyzer and Nanodrop ND-1000. Total RNA (100 ng) was used to prepare cDNA following the Affymetrix 3'IVT Express Kit labeling protocol (Affymetrix). Standardized array processing procedures recommended by Affymetrix were performed, including hybridization, fluidics processing and scanning of the Affymetrix MG-430 2.0 arrays. Gene-Spring GX11 software (Agilent Technologies, Santa Clara, Calif.) was used to normalize the raw data (Affymetrix CEL files) by Robust Multichip Average algorithm (RMA). Gene Set Enrichment Analysis (GSEA)39 was employed to identify significantly enriched gene expression patterns underlying fatty acid and lipid metabolism, by querying the C2 (curated pathways) and C5 (Gene Ontologies) categories of the GSEA MolSig v.3 database.

Hepatic Triglyceride Measurements

For triglyceride measurements (Hong et al., Hepatology 40, 933-941 (2004)), hepatic tissue was homogenized at 4° C. in RIPA lysis buffer (Sigma-Aldrich) and lipids extracted using a chloroform/methanol (2:1) method, evaporated, and dissolved in 2-propanol (Hong et al., Hepatology 40, 933-941 (2004)). Triglyceride concentration was assayed using the enzymatic hydrolysis of triglycerides by lipase to glycerol and free fatty acids and quantitation by colorimetric assay (Sigma-Aldrich).

Sequencing

The pooled sample was cleaned using the Agencourt AMPure system (Beckman Coulter Genomics, Danvers Mass., USA). The A and B adapters necessary for sequencing with 454-FLX Titanium chemistry (Roche, Indianapolis Ind.) were subsequently ligated to the sample pool after PCR following standard manufacturer protocols. Library construction, emPCR, enrichment, and 454 sequencing were performed by following the vendor's standard operating procedures with some modifications. Specifically, quantitative PCR was used to accurately estimate the number of molecules needed for emPCR. Automation (BioMek FX) was utilized to "break" the emulsions after emPCR and butanol was used to enable easier sample handling during the breaking process.

454-FLX Read Processing

After the completion of sequencing, a read processing pipeline consisting of a set of modular scripts designed at the JCVI were employed for deconvolution, trimming, and quality filtering (Li et al., BMC Res Notes 3, 199, (2010)). First reads were deconvoluted or assigned to samples based on their unique 10 nt barcode allowing no more than a one nt mismatch to the barcode. After deconvolution, barcode, and 16S primer sequences were removed allowing a maximum of 6 mismatches to the 16S primer and a maximum primer to barcode distance of 3 nt. Reads with an average length of <100 nt and reads with 'Ns' were removed. A Blastn quality check was performed against an internal data set of 16S reads to remove any sample reads not consistent with 16S gene sequences in which at least 30% of the query must be covered by the alignment (60 nt minimum). Passing reads were subsequently checked for chimeras using a modified version of the RDP Chimera Check, using a reference data set maintained in-house. Remaining reads then were classified to lowest taxonomic level possible using the RDP Classifier with 80% confidence. Taxonomic results (e.g., sample by taxa matrices) then were used for further analyses.

Quantitative PCR

Quantitative PCR assays to assess for taxa of interest were performed on a Rotor Gene 3000 quantitative PCR cycler using the LightCycler FastStart DNA Master PLUS SYBR Green I kit (Roche, Indianapolis Ind.) according to the manufacturer's instructions. Quantitative assays to assess total microbial census were performed for Bacteria using 16S rRNA and Fungi using ITS sequences. Quantitative assays were also performed for butyryl CoA transferase (BCoAT) and formyltetrahydrofolate synthetase (FTHFS). All primer sequences are provided in Table 1. Values were normalized using total Bacterial 16S copies prior to analyses.

TABLE 1

Primers used for real-time quantitative PCR for taxonomic and functional analyses.

| TARGET | Primer designation | Primer sequence | Annealing temp (F.) | SEQ ID NO |
|---|---|---|---|---|
| Bacteroidetes | Bact934F | GGARCATGTGGTTTAATTCGATGAT | 60 | 3 |
| | Bact1060R | AGCTGACGACAACCATGCAG | | 4 |
| Firmicutes | Firm934F | GGAGYATGTGGTTTAATTCGAAGCA | 60 | 5 |
| | Firm1060R | AGCTGACGACAACCATGCAC | | 6 |
| Bacteria | 338F | ACTCCTACGGGAGGCAGCAG | 60 | 7 |
| | 518R | ATTACCGCGGCTGCTGG | | 8 |
| Fungal | ITS1F | CTYGGTCATTTAGAGGAAGTAA | 55 | 9 |
| | ITS2R | RCTGCGTTCTTCATCGWTG | | 10 |
| BCoAT | BCoATscrF | GCIGAICATTTCACITGGAAYW SITGGCAYATG | 53 | 11 |
| | BCoATscrR | CCTGCCTTTGCAATRTCIACR AANGC | | 12 |
| FTHFS | fhs 1 | GTWTGGGCWAARGGYGGMGAAGG | 63 | 13 |
| | FTHFS-r | GTATTGDGTYTTRGCCATACA | | 14 |
| PPAR$_\gamma$ | PPARgF | GCCATTGAGTGCCGAGTC | 60 | 15 |
| | PPARgR | CATGTCGTAGATGACAAATGGTG | | 16 |
| CD36/FAT | CD36F | GGATCTGAAATCGACCTTAAAG | 60 | 17 |
| | CD36R | TAGCTGGCTTGACCAATATGTT | | 18 |

TABLE 1-continued

Primers used for real-time quantitative PCR for taxonomic and functional analyses.

| TARGET | Primer designation | Primer sequence | Annealing temp (F.) | SEQ ID NO |
|---|---|---|---|---|
| IRS-2 | IRS-1/2f | CTGGAGTATTATGAGTCGAGAAGAAGTGG | 60 | 19 |
|  | IRS-2r | TGTAGAGGGCGATCAGGTACTTGT |  | 20 |
| SREBP-1c | SREBP1f | AACGTCACTTCCAGCTAGAC | 72 | 21 |
|  | SREBP2r | CCACTAAGGTGCCTACAGAGC |  | 22 |
| GAPDH | gapdhF | TGGTGAAGGTCGGTGTGAAC | 60 | 23 |
|  | gapdhR | CCATGTAGTTGAGGTCAATGAAGG |  | 24 |

Quantitative PCR assays were performed using the LightCycler FastStart DNA Master PLUS SYBR Green I kit on a Rotor Gene 3000 quantitative PCR cycler.
Specific degenerate (R = A or G; W = A or T; M = A or C; Y = C or T; D = A, G, or T; I = inosine; N = A, C, G, or T) primers were used to assess for taxa of interest, including Bacteria, Bacteroidetes, Firmicutes, and fungi.
Degenerate primers were used to assess for two genes involved in short-chain fatty acid synthesis, butyryl CoA transferase (BCoAT) and formyltetrahydrofolate synthetase (FTHFS).
Genes involved in hepatic lipogenesis (PPAR$_\gamma$, CD36/FAT, IRS-2, SREBP-1c) also were compared after normalization with murine GAPDH.

Statistical and Computational Sequence Analysis

Quality-filtered sequences were further preprocessed through the Qiime pipeline (Caporaso et al., Nat Methods 7, 335-336 (2010)). The operational taxonomic unit (OTU) absolute abundance table and weighted Unifrac beta-diversity matrix (Lozupone et al., ISME J, 133 (2010); Lozupone & Knight, Appl Environ Microbiol 71, 8228-8235 (2005)) were extracted from the pipeline and PCA plots were produced based on weighted Unifrac distances. The rarefactions for diversity indices and species richness were calculated in the R statistical programming environment (R: A Language and Environment for Statistical Computing. R Foundation for Statistical Computing 1 (2009); Gentleman et al., Genome Biol 5, R80, (2004)) using Community Ecology Package Vegan. The OTU absolute abundances were converted to relative abundances by normalizing to total sequence count per sample analyzed. The resulting relative abundance matrix was used to produce heat maps and major taxa bar plots. All data are presented as Mean+/−SEM, unless otherwise indicated for groups without normal data distribution (Median+/−IQR). Comparisons of distributions between groups were analyzed using Fisher's exact test. Comparisons of medians between non-normally distributed groups were performed using the Mann-Whitney U test or Kruskal test for simultaneous comparisons of more than two groups. Analysis of taxonomic distributions amongst groups was performed using double-principal components analysis (DPCoA), as described (Pavoine et al., BMC Evol Biol 7, 156, (2007); Pavoine et al., J Theor Biol 228, 523-537, (2004)). To compare the inter- and intra-group statistical differences in beta diversity, a two-sided t-test was employed. It was ensured that the distributions of pairwise distances satisfied the normality assumptions of the t-test by examining their quantile-plots. P-values <0.05 were considered to be significant.

Example 1

FIG. 1 shows the design of the present Microbial Induced Obesity (MIO) experiments, key findings, and applications.

Figure 2:
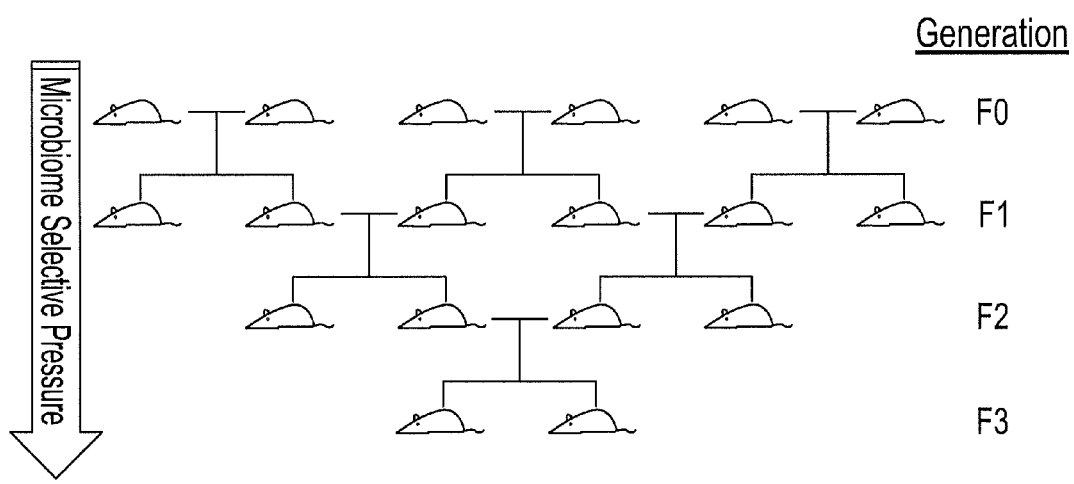
FIG. 2 is a model and breeding scheme of continuous STAT in successive generations. C57BL6 mice were obtained at 6 weeks of age from Jackson Laboratory for the F0 generation. F0 mice were mated and females were exposed to sub-therapeutic antibiotic treatment in the drinking water when pregnancy was detected. F1 generation mice were exposed to continuous STAT throughout life and at 12 weeks of age, mated to produce an F2 generation. Mice from F2 generation will be mated to produce an F3 generation. Mice, and all animals, are born sterile and acquire microbiota from maternal transmission. Successive generations kept on continuous STAT will have increased selective pressure on the intestinal microbiome, and should exhibit more profound alterations in body composition and phenotype.

C57BL6 mice were obtained at 6 weeks of age from Jackson Laboratory for the F0 generation. FIG. 2 shows a breeding scheme of continuous STAT in successive generations. F0 mice were mated and females were exposed to sub-therapeutic antibiotic treatment in the drinking water when pregnancy was detected. F1 generation mice were exposed to continuous STAT throughout life and at 12 weeks of age, mated to produce an F2 generation. Mice from F2 generation will be mated to produce an F3 generation. Mice, and all animals, are born sterile and acquire microbiota from maternal transmission. Successive generations kept on continuous STAT will have increased selective pressure on the intestinal microbiome, and should exhibit even more profound alterations in body composition and phenotype.

One group of sub-therapeutic penicillin-treated (STPT) mice received antibiotics at day 0 of life (at birth) (males n=5, females n=4) and a second group of STPT mice received antibiotics at day 28 of life upon weaning (males n=5, females n=6). Both groups received continuous antibiotic exposure through their drinking water until sacrifice at 20 weeks of age. Control mice (males n=6, females n=5) were not exposed to antibiotics. FIG. 3 panels a) and b) show growth curve; c) and d) show weight gain fit with Boltzmann curve, R2>0.9 for all groups; e) and f) show linear regression for weight gain in 4th week of life for male and female mice; g) shows growth rate (g/day) and R2 for week 3 of life and h) shows growth rate in 4th week of life, ***P<0.0005, t-test.

Figure 4:
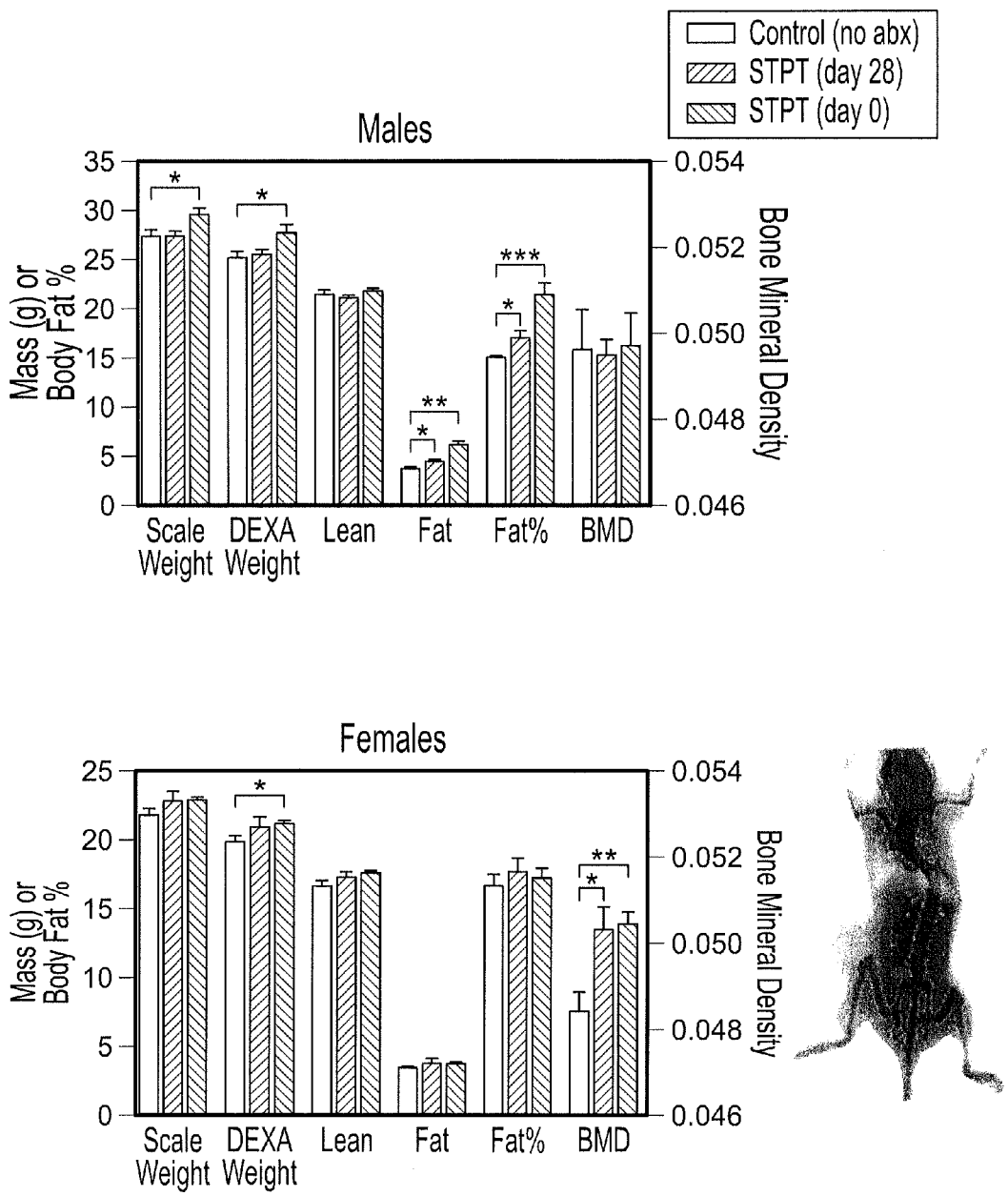
FIG. 4 shows body composition at 20 weeks of life in control and STPT mice. STPT mice were exposed to penicillin either at day 28 of life, or at day 0. Body weight was measured by electronic scale at 138±4 days of life. Total mass, lean mass, fat mass, body fat %, and bone mineral density were measured by dual energy x-ray absorptiometry (DEXA). *$P<0.05$, $P<0.005$, *$P<0.0005$, t-test.

FIG. 4 shows body composition at 20 weeks of life in control and STPT mice. STPT mice were exposed to penicillin either at day 28 of life, or at day 0. Body weight was measured by electronic scale at 138±4 days of life. Total mass, lean mass, fat mass, body fat %, and bone mineral density were measured by dual energy x-ray absorptiometry (DEXA). *P<0.05, P<0.005, *P<0.0005, t-test.

Figure 5A:
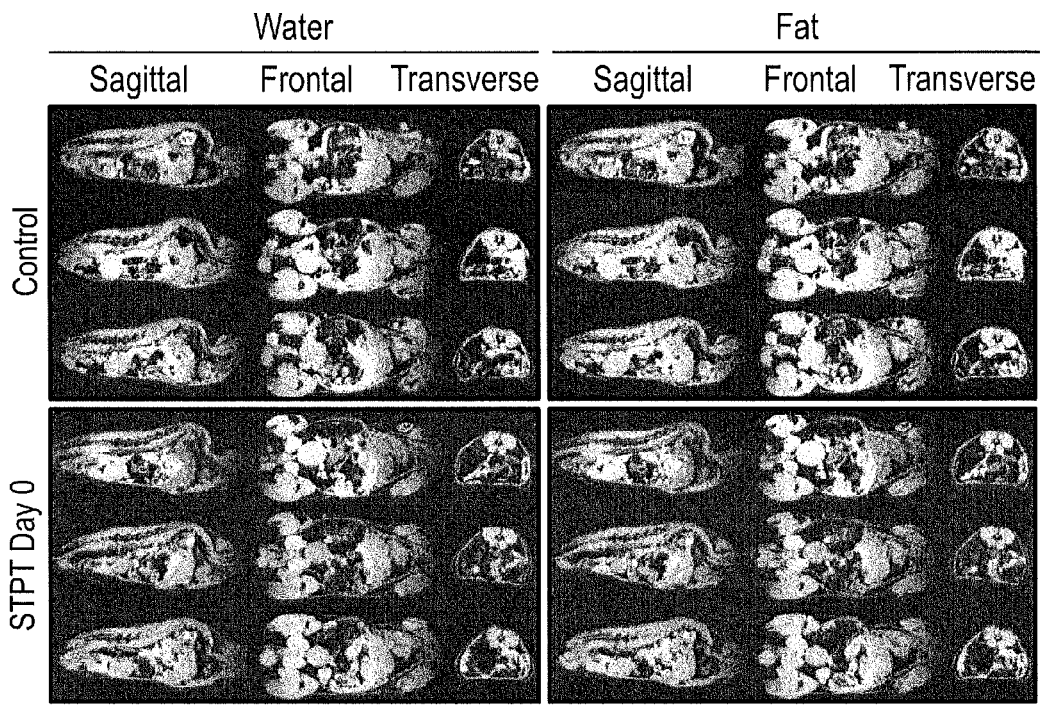
FIGS. 5A-C show water and fat magnetic resonance images (MRI) of representative control and STPT-mice exposed from day 0. Panel A) shows sagittal, frontal, and transverse magnetic resonance images of male control and STPT day 0 mice, n=3 for each. Water and fat images were separated based on chemical shift using IDEAL Dixon method. In panel B), water and fat images were merged to form a fat fraction image and total body fat % (vol/vol) was calculated. *$P<0.05$, t-test. Panel C) shows correlation of MRI and DEXA total body fat.
Figure 5B:
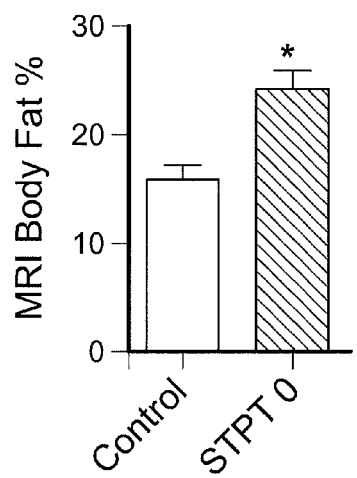
Figure 5C:
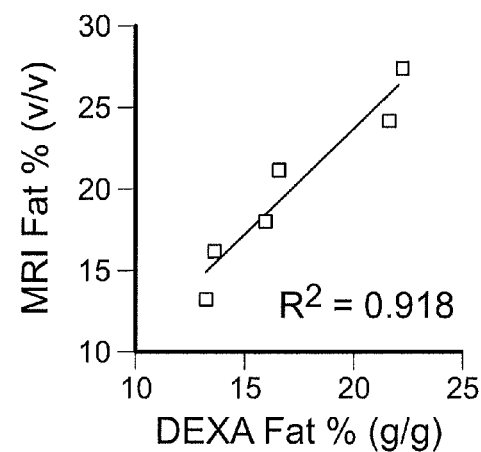
Figure 6A:
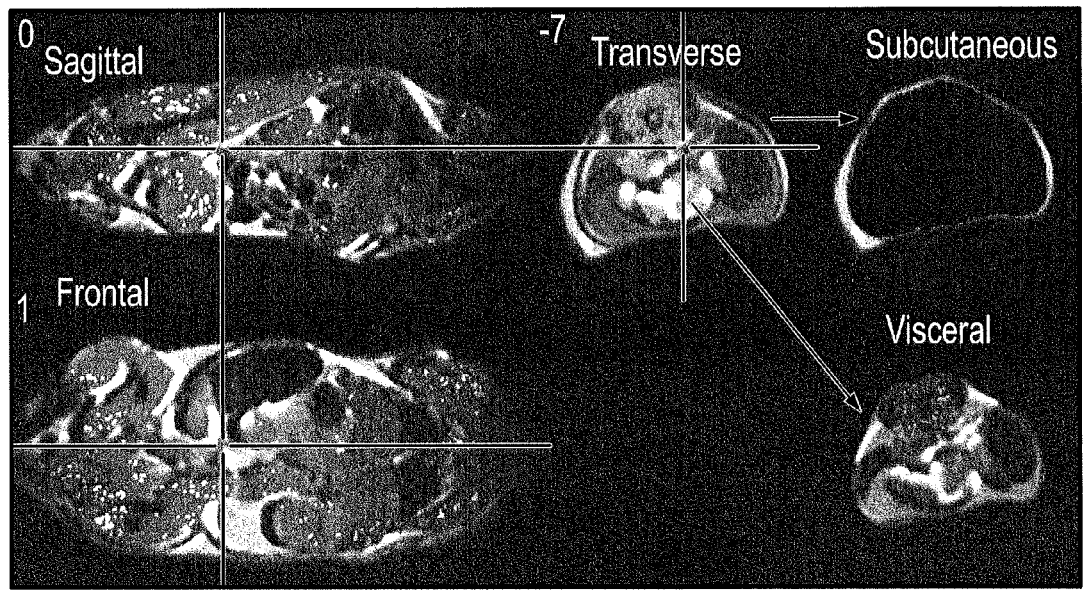
FIGS. 6A-D show abdominal fat distribution in STPT and control mice. 18-week old C57BL6/J male mice were scanned by magnetic resonance imaging (MRI) Panel A) Water image with fat image overlay. Using MRIcron software, the abdominal wall was traced in 3 consecutive transverse slices to create a visceral volume of interest (VOI) (shown as the "Transverse" image). A similar method was carried out for total abdominal and subcutaneous VOI. Fat volume was calculated from mean fat % and total volume for each VOI in the fat fraction image. Panels B-D) show visceral, subcutaneous, and total fat volume: Panel B) in individual mice; Panel C) correlation with body fat %; Panel D) mean for control and STPT day 0 mice. *$P<0.05$, t-test.
Figure 6B:
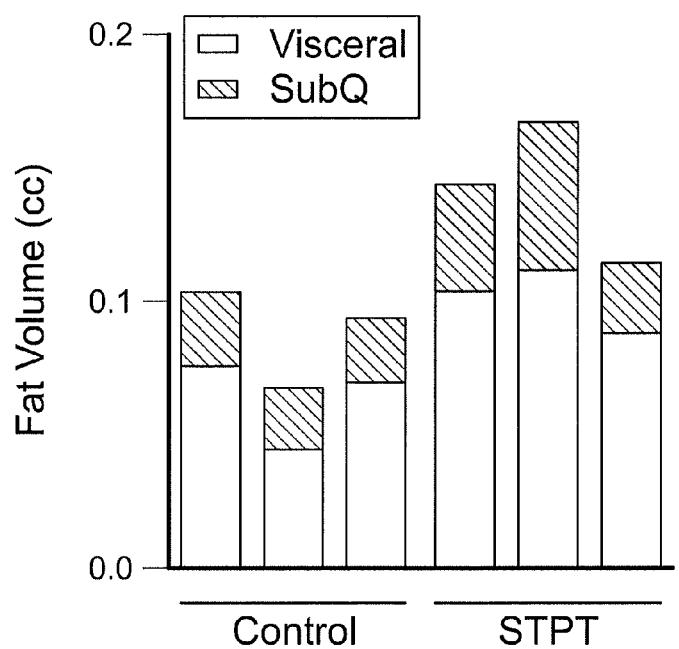
Figure 6C:
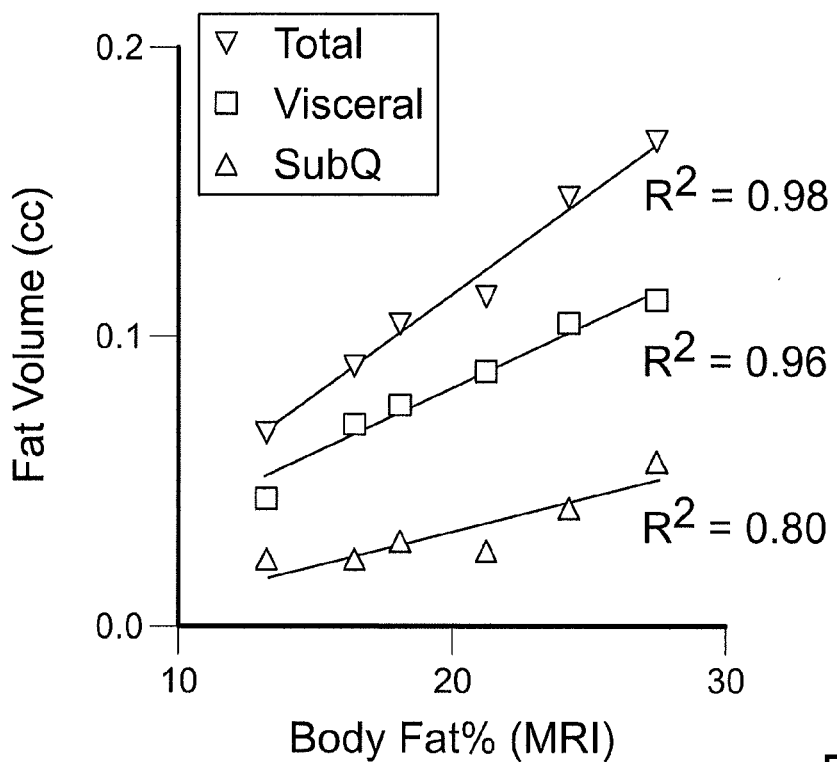
Figure 6D:
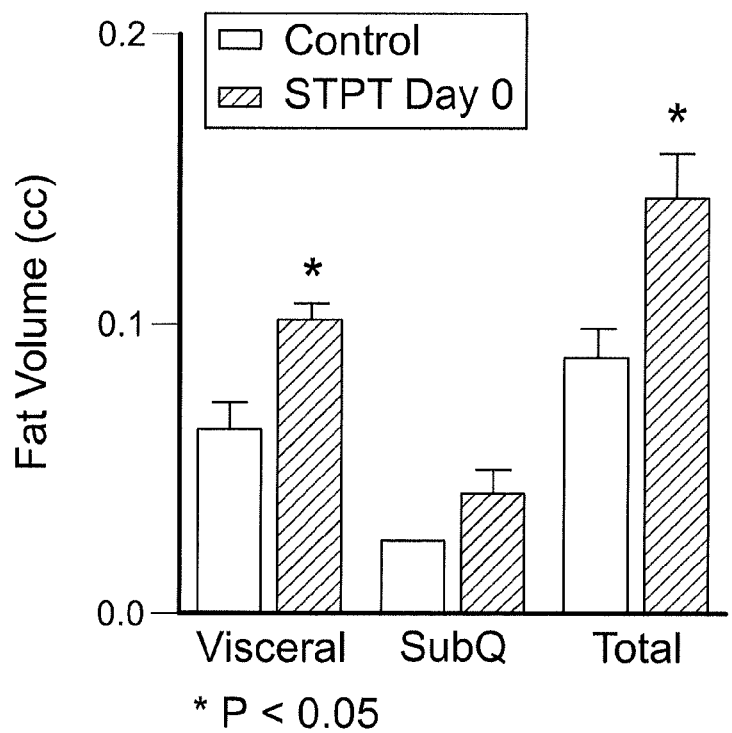

FIGS. 5A-C show water and fat magnetic resonance images (MRI) of representative control and STPT-mice exposed from day 0. Panel A) are Sagittal, frontal, and transverse magnetic resonance images of male control and STPT day 0 mice, n=3 for each. Water and fat images were separated based on chemical shift using IDEAL Dixon method. In panel B), water and fat images were merged to form a fat fraction image and total body fat % (vol/vol) was calculated. *P<0.05, t-test. Panel C) shows correlation of MRI and DEXA total body fat.

FIGS. 6A-D show abdominal fat distribution in STPT and control mice. 18-week old C57BL6/J male mice were scanned by magnetic resonance imaging (MRI). Panel A) shows water image (grey) with fat image overlay (yellow). Using MRIcron software, the abdominal wall was traced in 3 consecutive transverse slices to create a visceral volume of interest (VOI) (red). A similar method was carried out for total abdominal and subcutaneous VOL Fat volume was calculated from mean fat % and total volume for each VOI in the fat fraction image. Panels B-D) show visceral, subcutaneous, and total fat volume: Panel B) shows fat volume in individual mice. Panel C) shows correlation with body fat %, and Panel D) shows mean for control and STPT day 0 mice. *P<0.05, t-test.

Figure 7A:
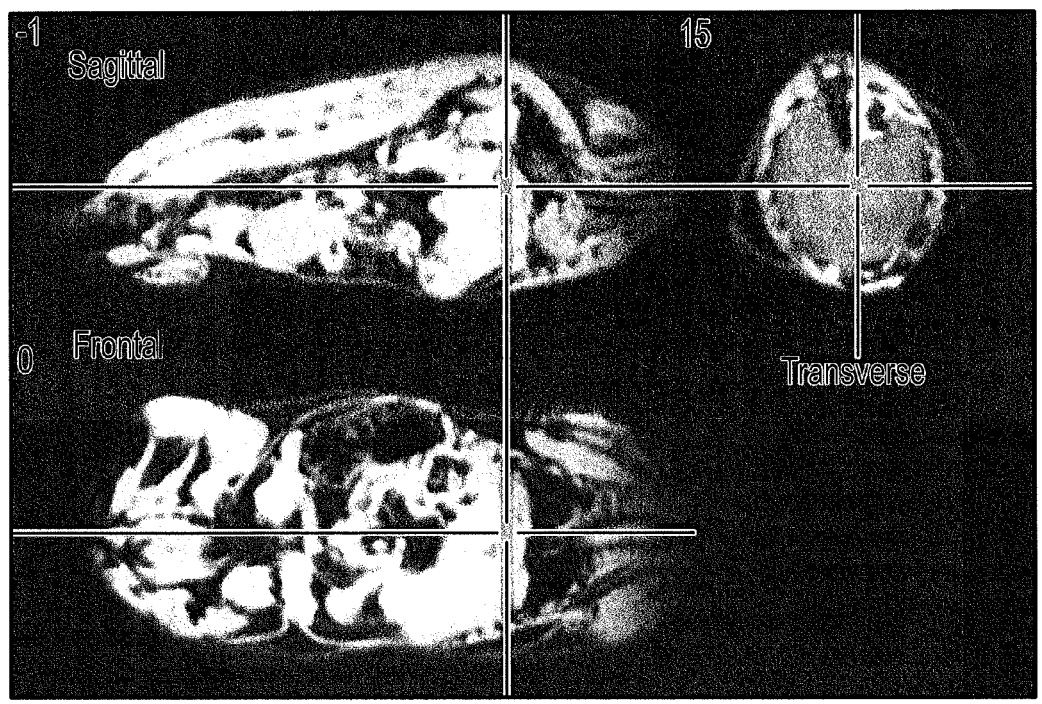
FIGS. 7A-C show liver adiposity in STPT and Control Mice. Panel A) 5 consecutive transverse sections of the liver were traced to create a liver volume of interest (VOI) using MRIcron software. Panel B) Mean liver fat % in control and STPT day 0 mice, n=3 for each. *$P=0.052$ Panel C) Correlation of liver fat % with body fat %.
Figure 7B:
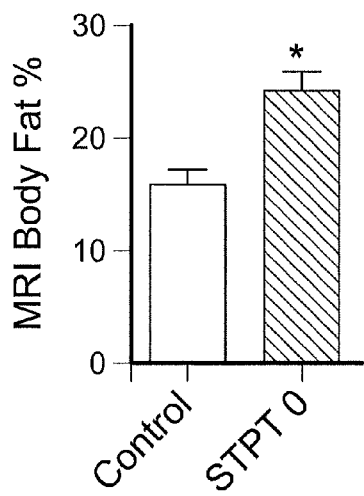
Figure 7C:
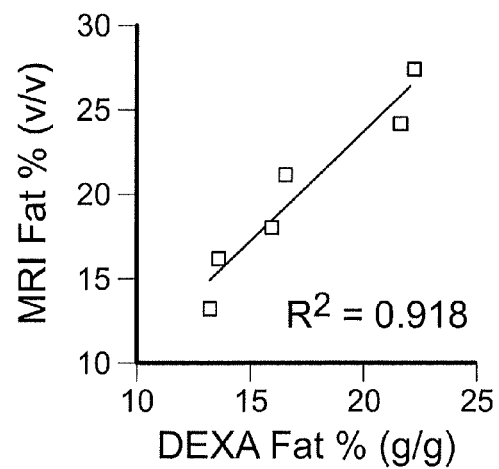

FIGS. 7A-C show liver adiposity in STPT and Control Mice. In Panel A), 5 consecutive transverse sections of the liver were traced to create a liver volume of interest (VOI) using MRIcron software. Panel B) shows mean liver fat % in control and STPT day 0 mice, n=3 for each. *P=0.052. Panel C) shows correlation of liver fat % with body fat %.

Figure 8A:
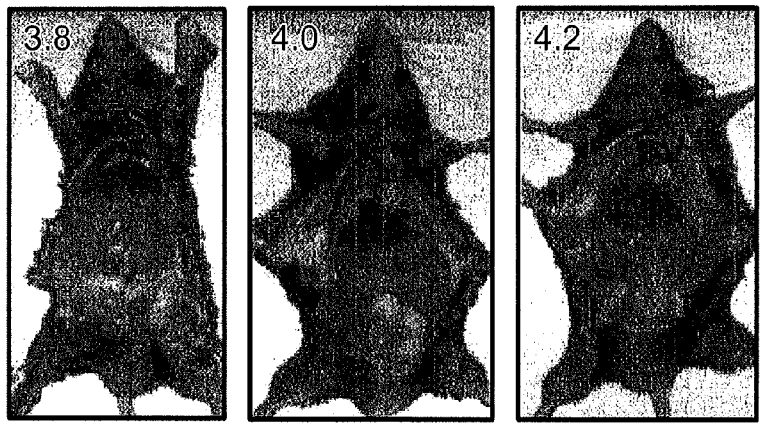
FIGS. 8A-C are representative images of control and STPT F1 male mice from post-mortem dissection during week 20 of age (140-143 days). Groups are: Panel A, Controls (no antibiotic treatment); Panel B, STPT-exposure from day 28 of life until sacrifice; Panel C, STPT-exposure from day 0 of life until sacrifice. Numbers on each image represent grams of fat determined by in vivo DEXA scanning (performed during days 136-139 of life).
Figure 8B:
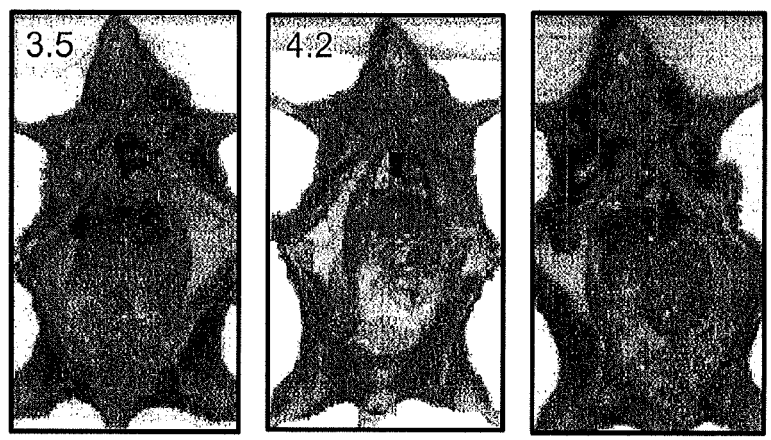
Figure 8C:
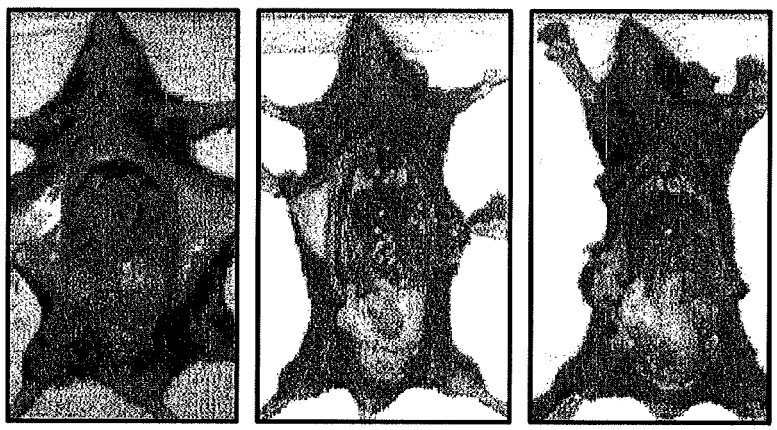
Figures 9A, 9B, 9C, 9D:
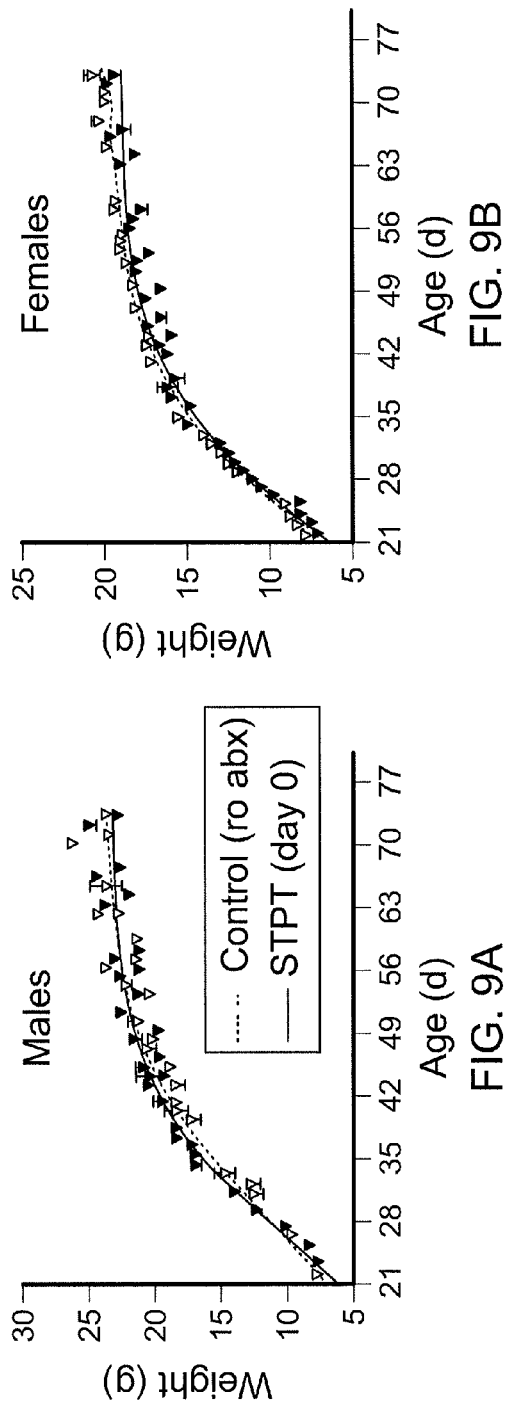

FIGS. 8A-C show representative images of control and STPT F1 male mice from post-mortem dissection during week 20 of age (140-143 days). Groups are: Panel A, Controls (no antibiotic treatment); Panel B, STPT-exposure from day 28 of life until sacrifice; Panel C, STPT-exposure from day 0 of life until sacrifice. Numbers on each image represent grams of fat determined by in vivo DEXA scanning (performed during days 136-139 of life).

FIGS. 9A-H show growth dynamics of control and STPT mice, exposed at birth, from F1 generation, litter 2. Sub-therapeutic penicillin-treated (STPT) C57BL6/J mice received antibiotics at day 0 of life (at birth) continuously through their drinking water (males n=10, females n=18). Control mice were not exposed to antibiotics (males n=5, females n=13). Growth curves (Panels a and b). Weight gain fit with Boltzmann curve, $R^2>0.9$ for all groups (Panels c and d). Linear regression for weight gain during early development (Panels e and f). Growth rate (g/day) and R2 during early development (Panel g) Growth rate measured from day 22 to 31***P<0.0005, t-test (Panel h).

Figure 10:
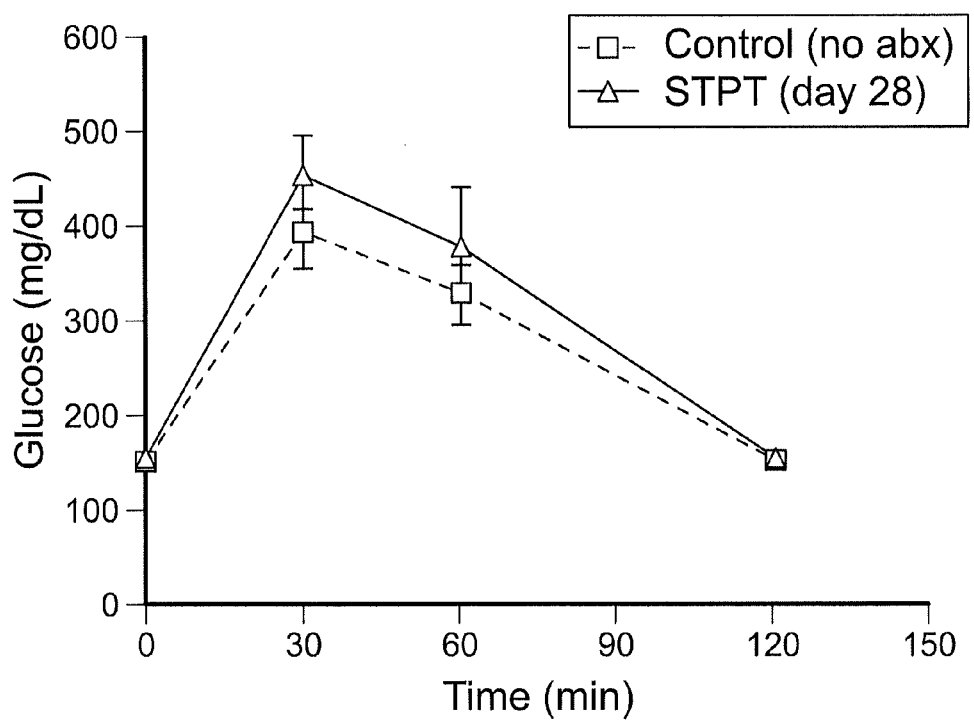
FIG. 10 is a graph showing glucose tolerance test from 8-week old female C57BL6/J mice. Glucose was injected intraperitoneally and blood glucose was measured at baseline, and at 30, 60, and 120 minutes. The solid line represents mice treated with sub-therapeutic penicillin from 3 weeks of age, and the dashed line represents control mice, given no antibiotic. Each group contained 5 mice.

FIG. 10 is a graph showing glucose tolerance test from 8-week old female C57BL6/J mice. Glucose was injected intraperitoneally and blood glucose was measured at baseline, and at 30, 60, and 120 minutes. The solid line represents mice treated with sub-therapeutic penicillin from 3 weeks of age, and the dashed line represents control mice, given no antibiotic. Each group contained 5 mice.

Figure 11A:
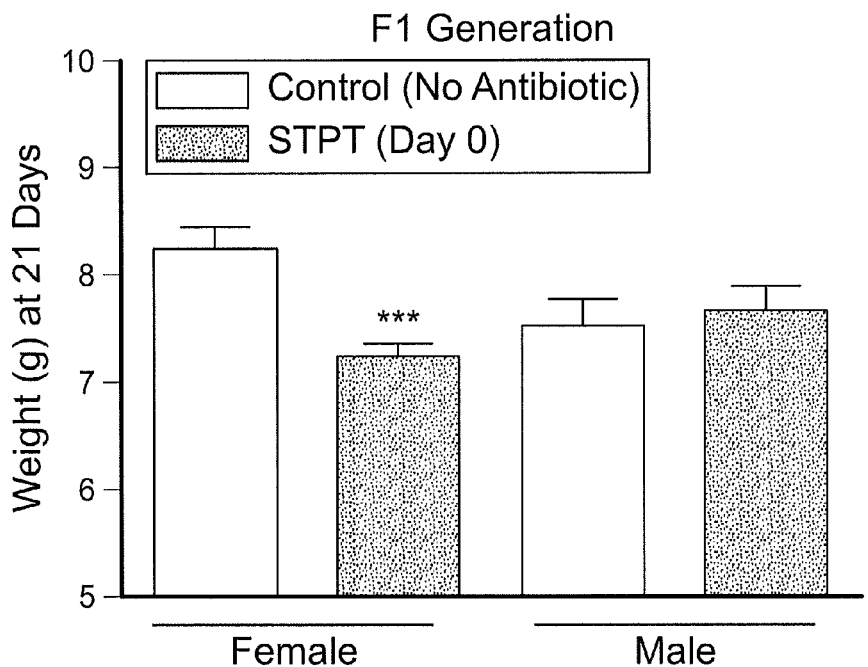
FIGS. 11A-B show weight at 21 days of the F1 and F2 generation of STPT and Control mice. a) Weight at 21 days was significantly decreased in female STPT F1 generation mice, while there was no difference between weight at 21 days in STPT and control mice. b) Weight at 21 days was significantly increased in STPT mice for both females and males.
Figure 11B:
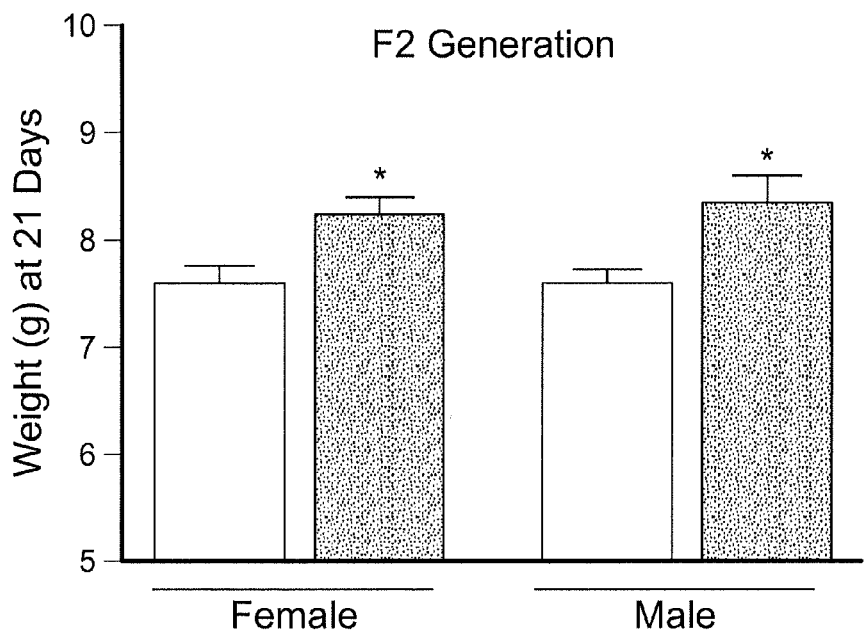

FIGS. 11A-B show weight at 21 days of the F1 and F2 generation of STPT and Control mice. a) Weight at 21 days was significantly decreased in female STPT F1 generation mice, while there was no difference between weight at 21 days in STPT and control mice. b) Weight at 21 days was significantly increased in STPT mice for both females and males.

The results of this study demonstrate that sub-therapeutic antibiotic treatment:
Alters early life growth kinetics;
Increases total weight gain when administered from birth;
Increases fat mass in males, and has a greater effect when administered from birth;
Increases bone mineral density in female mice, and
Increases visceral, subcutaneous, abdominal fat, and liver adiposity.

The present work provides a pathway to uncover the depleted microbiota, or to reduce the over-represented microbiota which then can lead into antibiotic, pre-biotic, and pro-biotic applications to therapy and prevention, and diagnostic tests to assess the state of the microbiota—by taxonomic group or by metabolic pathway, or by antigenic presentation—to allow for the proper application of preventatives and/or therapeutics.

Example 2

Figure 12A:
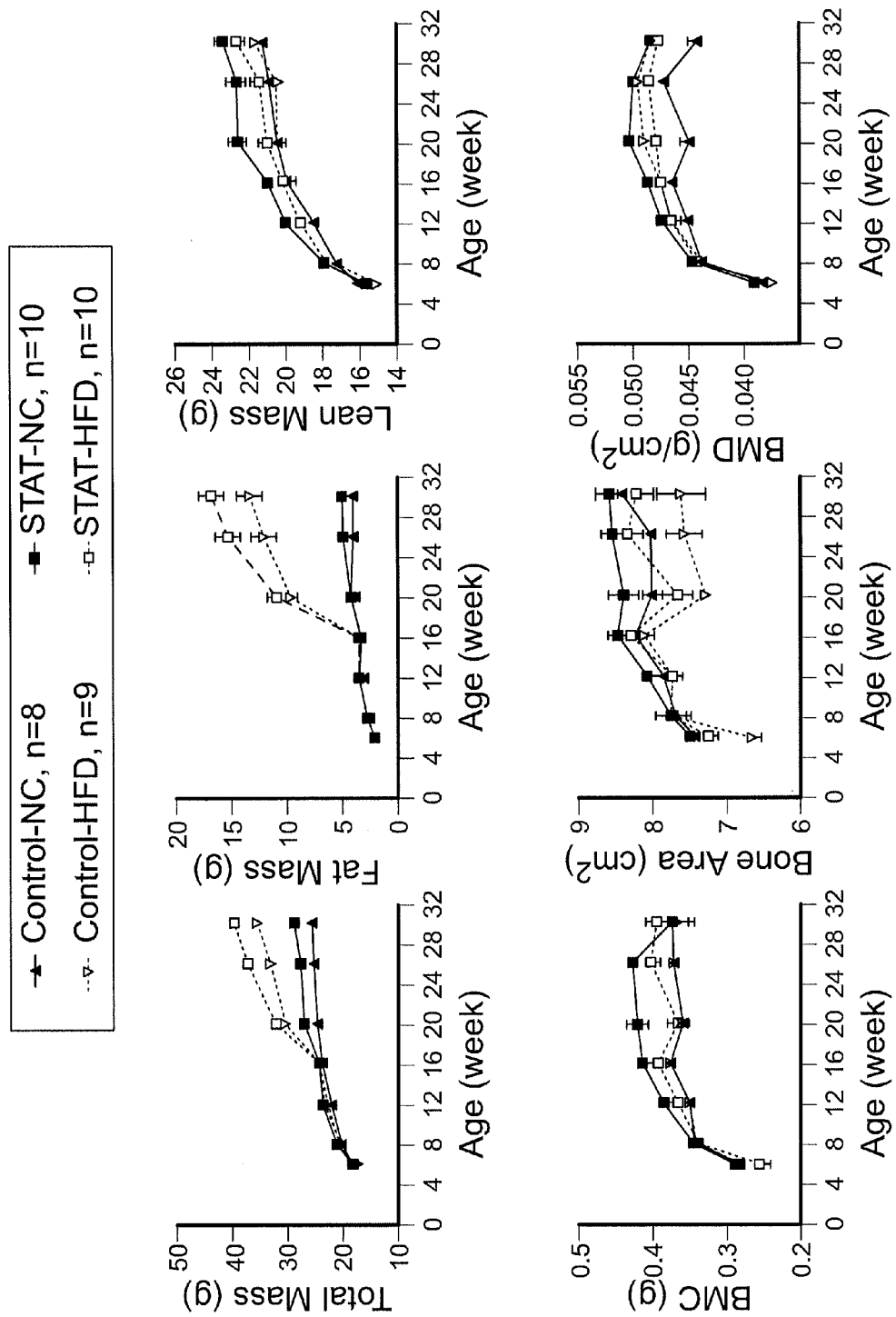
FIGS. 12A-B are graphs showing morphometric and bone development in C57/C6 mice, in relation to gender (panel A—males; panel B—females), diet, and antibiotic exposure. All mice were raised on normal chow (NC, 13.5% kcal from fat) then at 17 weeks of age, half of the mice were continued on LFD and half were switched to high fat diet (HFD, 45% kcal from fat). Panel A males, Panel B females: total mass, fat mass, lean mass, bone mineral content, bone area, and bone mineral density. Arrow indicates change in diet for mice on HFD.
Figure 12B:
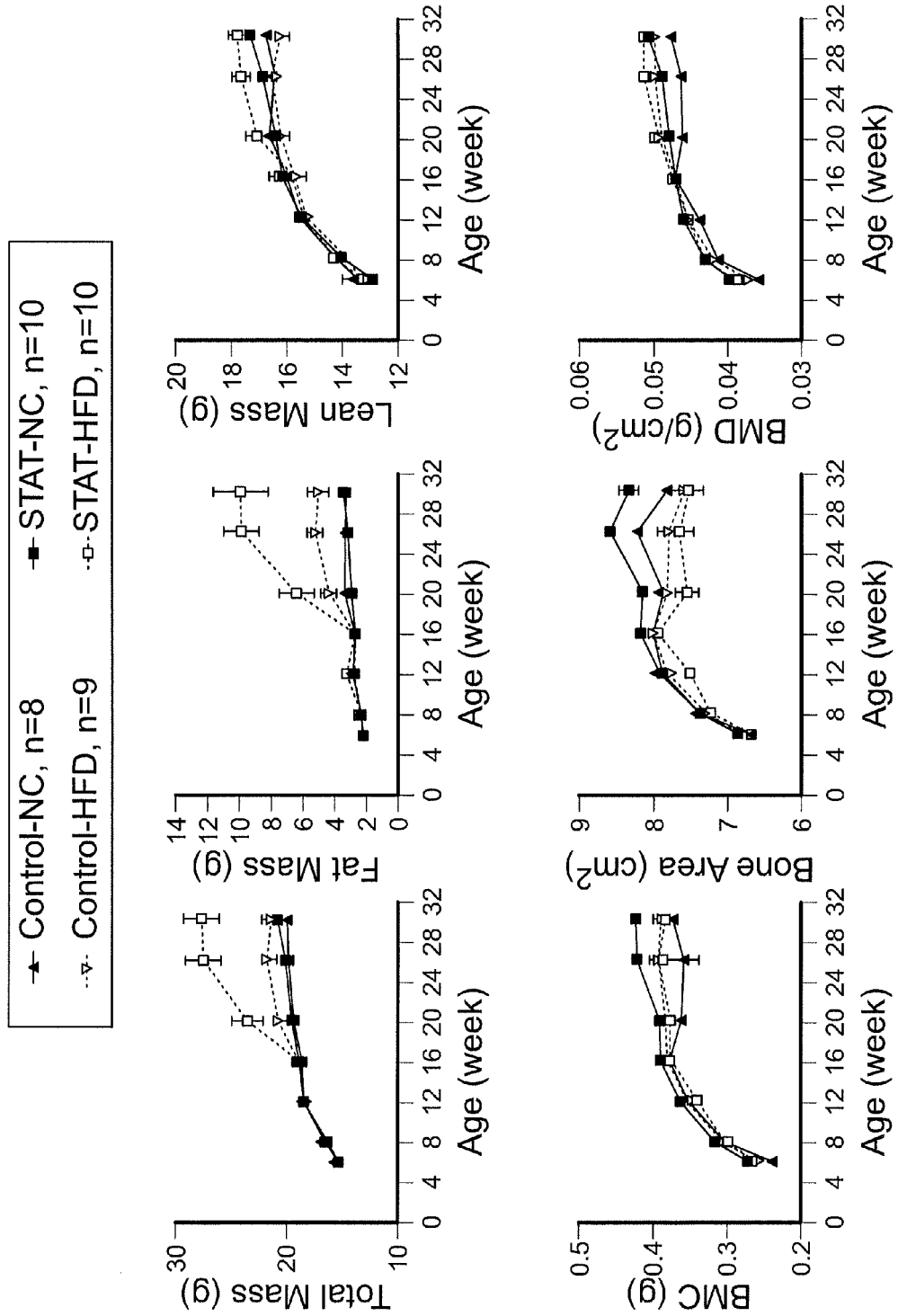

STAT Increases Insulin Levels and a High Fat Diet (HFD) Increases the STAT-Mediated Obesity FIGS. 12A-B are graphs showing morphometric and bone development in C57/C6 mice, in relation to gender (panel A—males; panel B—females), diet, and antibiotic exposure. All mice were raised on normal chow (NC, 13.5% kcal from fat) then at 17 weeks of age, half of the mice were continued on LFD and half were switched to high fat diet (HFD, 45% kcal from fat). Panel A males, Panel B females: total mass, fat mass, lean mass, bone mineral content, bone area, and bone mineral density. Arrow indicates change in diet for mice on HFD.

Figure 13A:
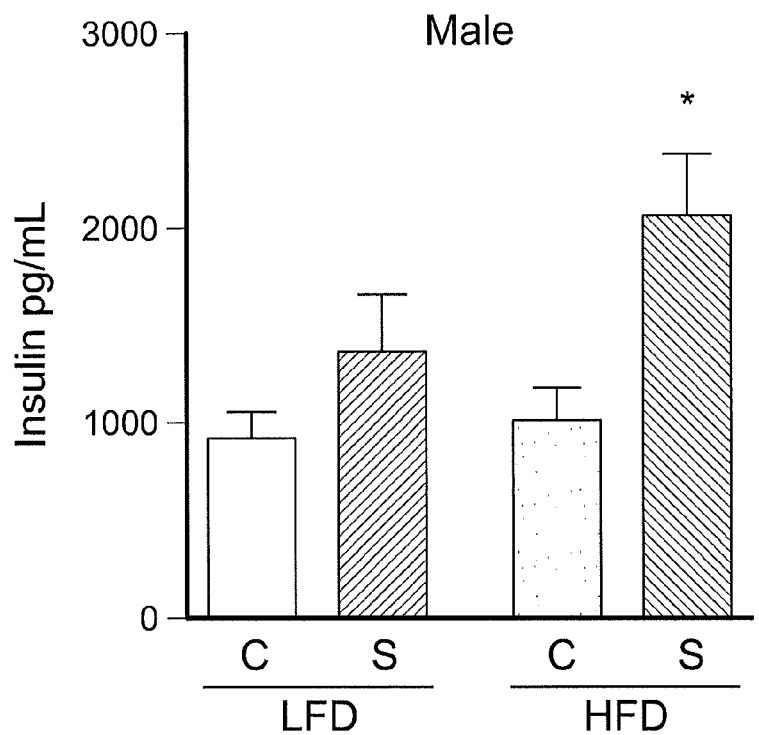
FIGS. 13A-B show fasting blood insulin levels in (A) male and (B) female 30-week old C57/B6 mice. Mice were either control (C) water or sub-therapeutic antibiotic treated (S) with penicillin from birth. All mice were raised on normal chow (LFD, 13.5% kcal from fat) then at 17 weeks of age, half of the mice were continued on LFD and half were switched to high fat diet (HFD, 45% kcal from fat). *P<0.05 Mann-Whitney U.
Figure 13B:
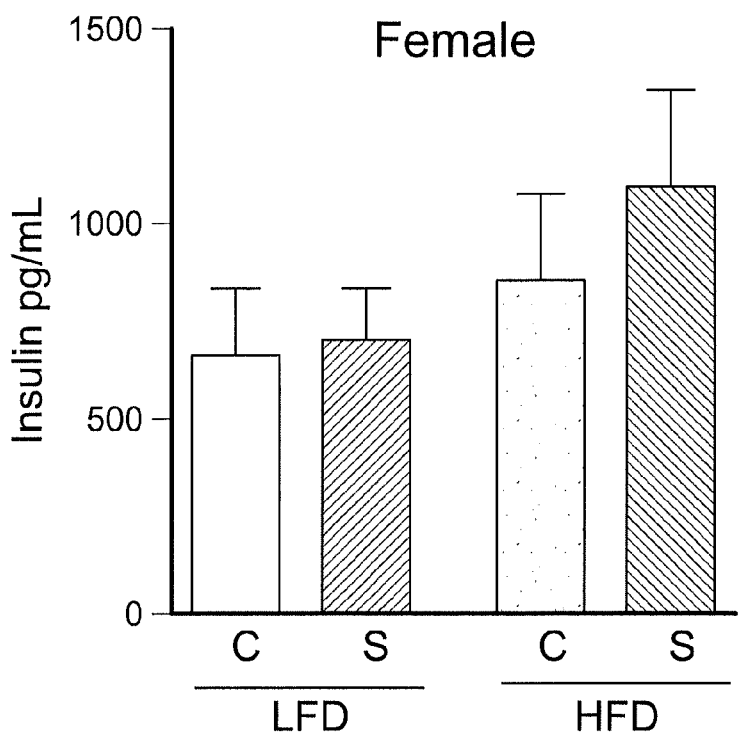

FIGS. 13A-B show fasting blood insulin levels in (A) male and (B) female 30-week old C57/B6 mice. Mice were either control (C) water or sub-therapeutic antibiotic treated (S) with penicillin from birth. All mice were raised on normal chow (LFD, 13.5% kcal from fat) then at 17 weeks of age, half of the mice were continued on LFD and half were switched to high fat diet (HFD, 45% kcal from fat). *P<0.05 Mann-Whitney U.

Example 3

STAT Alters Composition of Intestinal Microbiota

Figure 14:
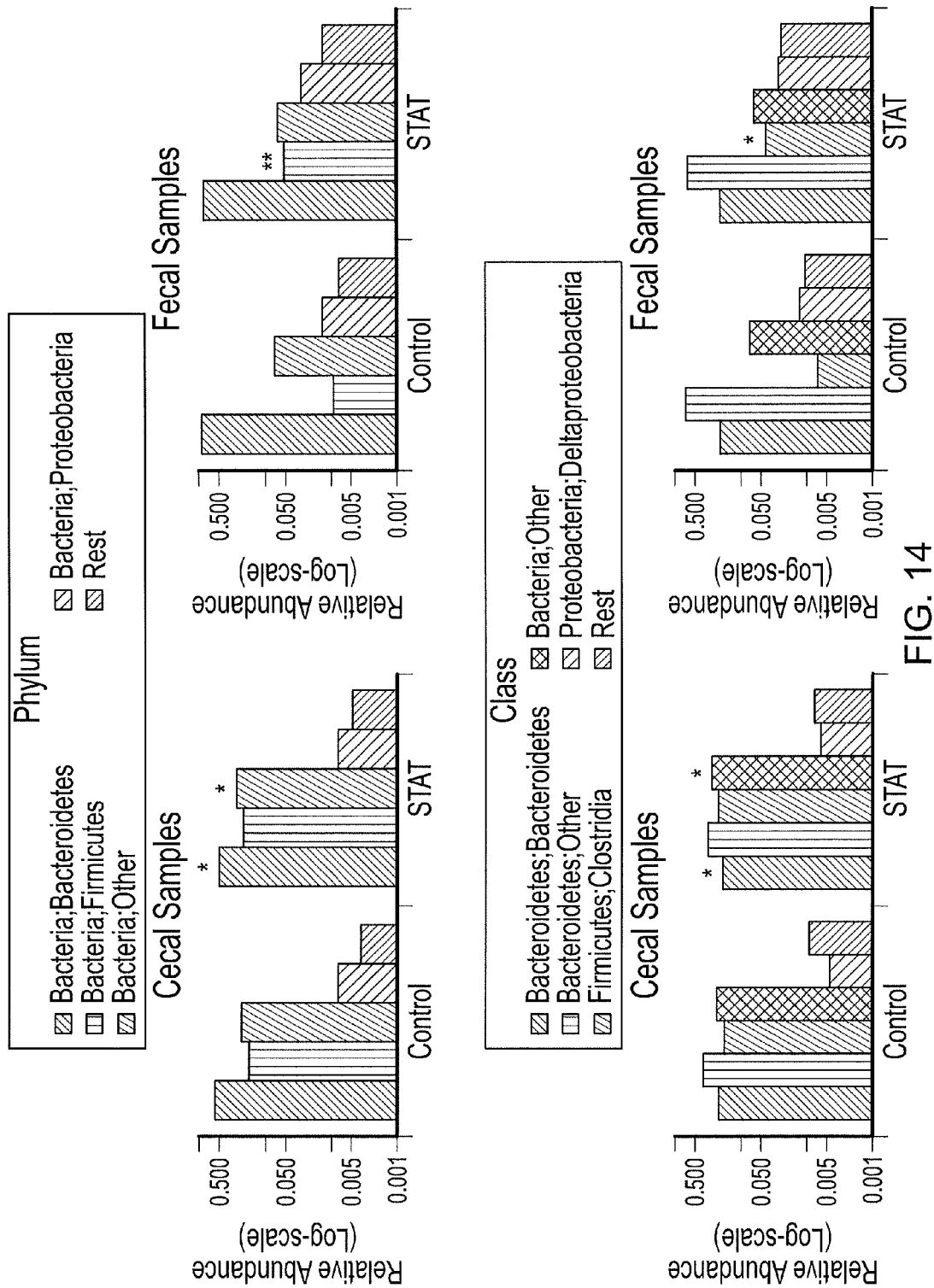
FIG. 14 shows abundance of major taxa present. Each panel (left for cecal, right for fecal samples) presents the abundance of the taxa present >1% in all samples at each designated taxonomic level. The relative abundance is shown on a log scale. Abundances that are significantly different (two-sided Kruskal test, p<0.05) between control and STAT samples are marked with *(p<0.05) or **(p<0.01).
Figure 14:
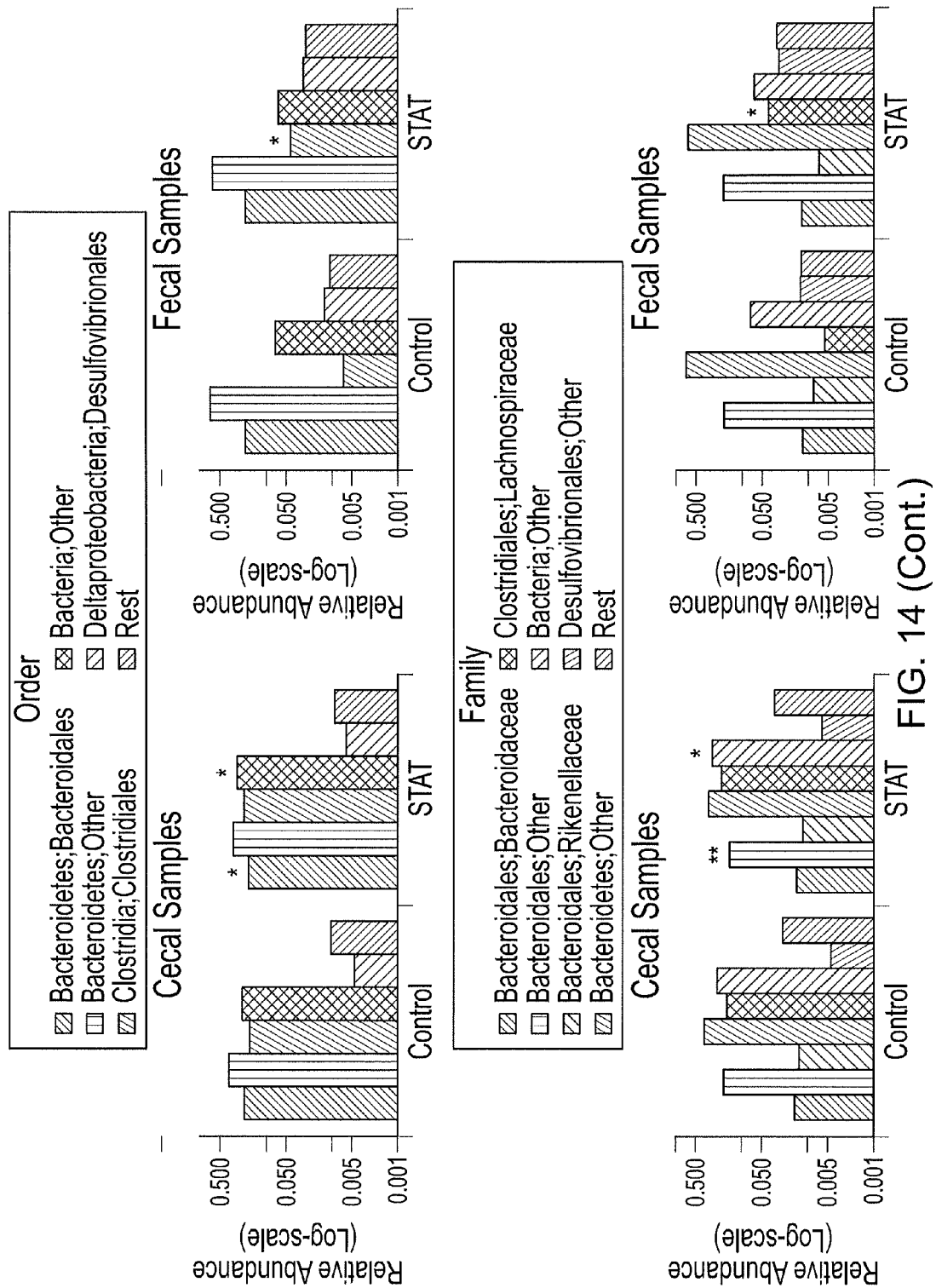
Figure 14:
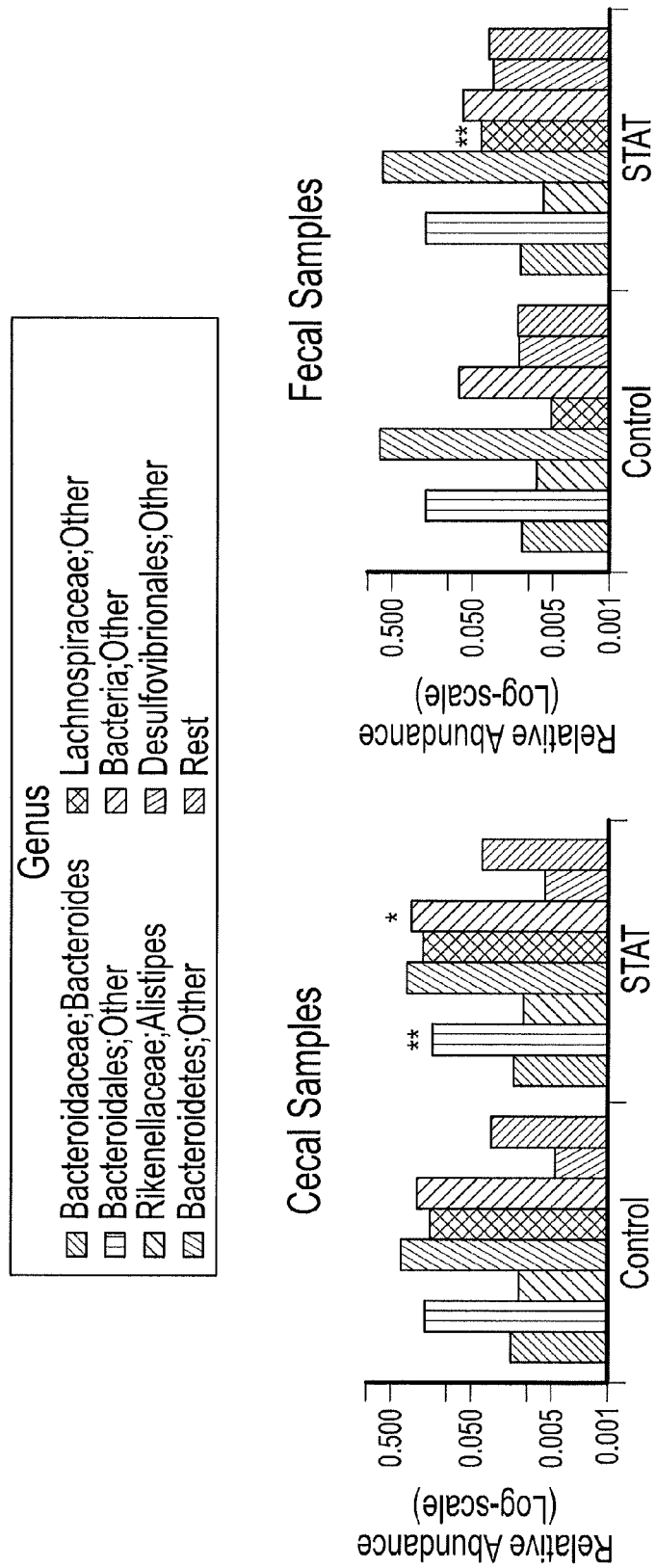

To assess microbial populations in the STAT and control microbiomes, the relative distribution of taxonomic groups based on 16S rRNA v3 region sequence data were analyzed. The extracted DNA was subjected to 454 pyrosequencing, yielding 555,000 readable v3 sequences (5784±676 sequences/sample with mean length 188±3 bp). The sequences were analyzed at multiple (Phylum→Family) taxonomic levels (FIG. 14).

In both fecal and cecal samples, the ratio of Firmicutes to Bacteria was significantly elevated in the STAT mice compared to controls. Heat map visualization of the Unifrac distances that define population structure showed a non-random distribution of STAT and control mice (p<0.05). Importantly, deep phylogenetic branching was identified, with the mean weights of mice on the two heat map major branch points significantly (p<0.05) different (21.4+3.1% (upper) vs. 23.0+2.8% (lower)). A major contributor to the observed differences is increased Lachnospiraceae representation in the STAT mice. Additional Unifrac analyses and PCA demonstrated consistent shifts within the microbial populations in the STAT-exposed group.

Example 4

STAT Exposure Alters Gut Microbiome Short-Chain Fatty Acid Metabolic Capabilities Because of the central role of short-chain fatty acid synthesis in colonic metabolism (Wong et al., J Clin Gastroenterol 40, 235-243 (2006)), the effect of STAT exposure on the prokaryotic genes butyryl coA transferase (BCoAT) and formyltetrahydrofolate synthetase (FTHFS) that play roles in butyrate and acetate synthesis was examined Degenerate quantitative PCRs for BCoAT and FTHFS (primers listed in Table 1) were performed on fecal specimens in STAT (penicillin) and control mice. At 3 weeks, BCoAT gene copies were significantly higher in the STAT (193±22 normalized copies) compared to the control mice (127±15 normalized copies), but by 7 weeks, the results normalized. There were no significant differences in FTHFS gene copies at 3 weeks, but there was a significantly higher number of FTHFS copies in the STAT mice than in the controls by 7 weeks). These findings provide evidence that STAT exposure perturbs not only GI microbiome, composition but also abundance of genes critical to host energy homeostasis.

Example 5

STAT Alters Hepatic Metabolism of Fatty Acids and Lipids

Figure 15A:
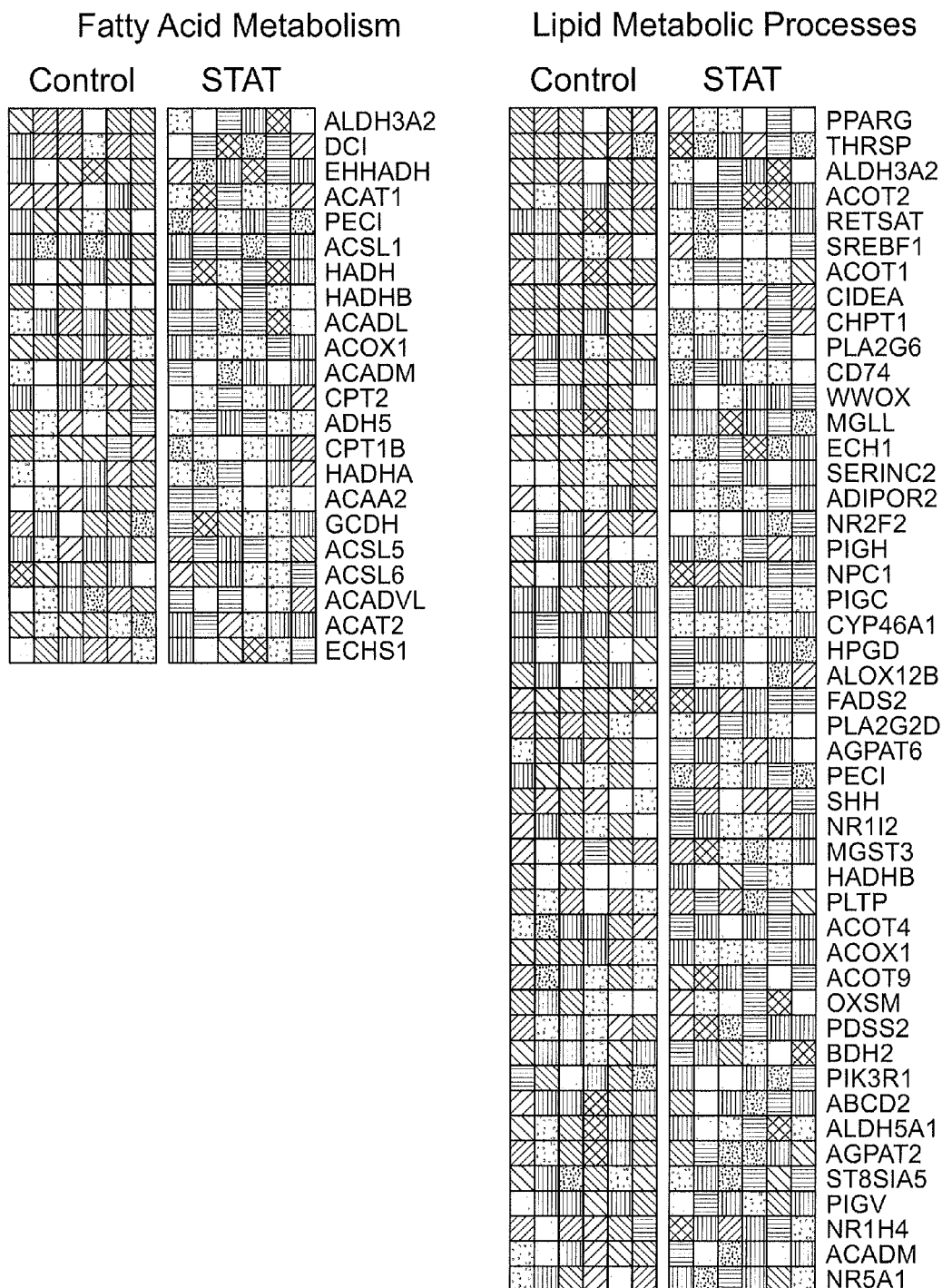
FIGS. 15A-C show differentially regulated genes related to hepatic lipogenesis, identified through microarray and quantitative PCR analyses. (A) Microarray analysis of liver specimens from control and STAT mice surveyed for differences in >45,000 genes; 397 genes were significantly up- or down-regulated when independently analyzed by t-test and PTM, with subsequent analysis using the GSEA39 and DAVID40 algorithms. Heat maps generated by GSEA identify differences between the STAT and control mice, particularly in pathways related to fatty acid metabolism and lipid metabolic processes. (B) After lipid extraction from liver homogenates using a chloroform/methanol method, triglyceride levels between control (n=7) and STAT (n=9) mice did not differ significantly, indicating transport to peripheral tissues. (C) Specific genes of interest that differed between STAT and control mice in the microarray analyses (left column) were selected for quantitative PCR. Differences consistent with those identified in the microarray analyses of PPARγ, fatty acid transporter (FAT/CD36), SREBP1c, and insulin receptor substrate 2 (IRS-2) were observed. *p<0.05
Figure 15B:
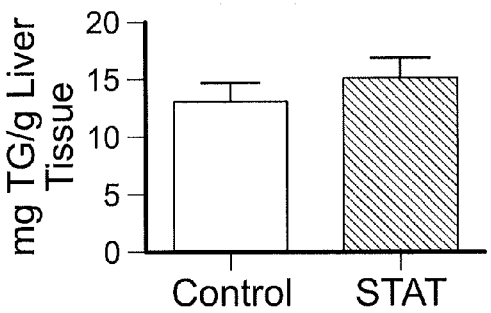
Figure 15C:
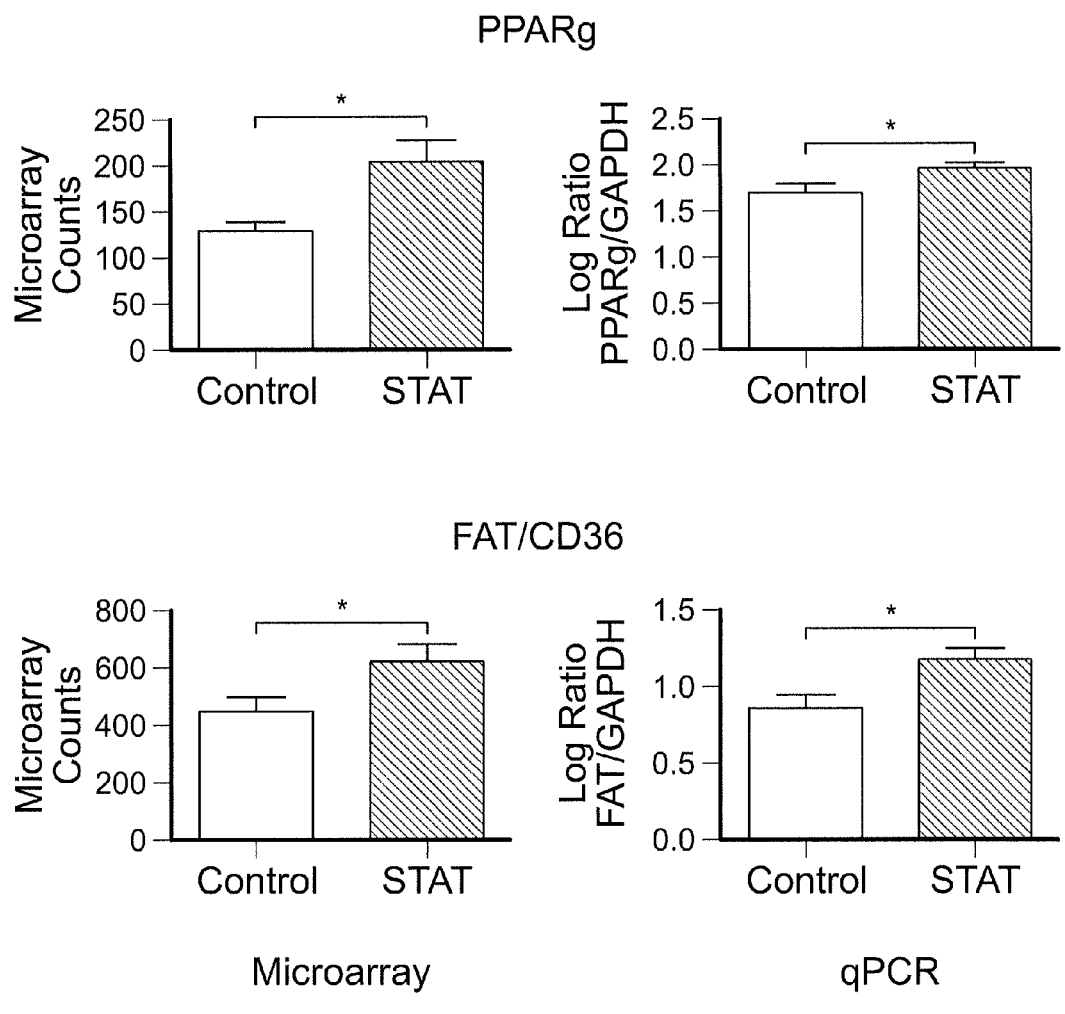

In confirmatory experiments using the identical STAT penicillin protocol, liver tissue was collected from both control and STAT mice. Microarray analyses surveyed for differences in >45,000 genes and identified 466 that by t-test or PTM were significantly up- or down-regulated (397 significantly differed from controls by both tests) in the STAT compared to control mice. Focusing on pathways related to fatty acid metabolism and lipid metabolic processes, 22 and 47 genes, respectively, were differentially expressed between STAT and control mice (FIG. 15A). Four genes of interest, PPARγ, fatty acid translocase (FAT, also known as CD36), SREBP1c, and insulin receptor substrate 2 (IRS-2) were evaluated by qPCR to confirm the changes identified by microarray analysis (FIG. 15B, left column) Both PPARγ and FAT had significantly higher normalized gene counts in the STAT than in control mice, confirming the microarray analysis observations. Although not statistically significant, (FIG. 15B, right column), SREBP1c and IRS-2 qPCR results showed relationships in the same direction as in the microarrays.

By developing a model to assess adiposity, Examples 3-5 demonstrate that each of the several STAT approaches tested affects the adiposity of post-weaning C57B6 mice. Similarly, there was a consistent early change in bone development. Among several hormones related to metabolism, glucose-dependent insulinotropic peptide (GIP), an incretin family peptide synthesized by small intestinal K cells (Buffa et al., Histochemistry 43, 249-255 (1975)) with receptors on adipocytes and stimulating lipoprotein lipase activity (Miyawaki et al., Nat Med 8, 738-742 (2002)), was significantly elevated in the STAT mice. GIP elevation in STAT mice provides a mechanism for the observed adiposity increase, but also could be secondary to the metabolic changes.

Although STAT did not change the overall bacterial density, even the minimal antibiotic doses used caused shifts in taxonomic composition, such as the Lachnospiraceae bloom. In contrast to adults, young animals develop phenotypically at rapid rates and small microbiome disturbances could have substantial long-term host effects due to altered metabolic capabilities during time-sensitive early development. On the farm, growth promotion is enhanced the earlier in life STAT exposure is initiated (Wong et al., J Clin Gastroenterol 40, 235-243 (2006); Bergman, Physiol Rev 70, 567-590 (1990)). Both BCoAT and FTHFS are critical in metabolism of carbohydrates into short-chain fatty acids (SCFA) (Louis & Flint, Applied and Environmental Microbiology 73, 2009-2012 (2007); Lovell & Leaphart, Methods in Enzymology 397, 454-469 (2005)); the observed increases in their gene copy numbers in STAT mice relative to controls provides evidence that the STAT colonic microbiome had enhanced potential for SCFA production. SCFAs directly provide energy to colonocytes and their absorption into the portal circulation stimulates adipogenesis (Wong et al., J Clin Gastroenterol 40, 235-243 (2006); Bergman, Physiol Rev 70, 567-590 (1990)). Furthermore, the present microarray and qPCR findings demonstrate substantial changes in the regulation of hepatic lipid and fatty acid metabolism. Because the portal circulation and liver are downstream of intraluminal intestinal changes, the present findings suggest possible STAT-induced mechanisms that affect host metabolism and phenotype. Ultimately, the interaction between the microbiome's metabolic capabilities and numerous host reactive cells could account for the observed changes, including the increase in GIP.

Example 6

The Effect of *H. Pylori* Eradication on Meal-Associated Changes in Plasma Ghrelin and Leptin Background The healthful regulation of energy homeostasis in humans, depends on centrally-acting hormones such as ghrelin and leptin [1, 2]. Serum ghrelin concentrations increase during fasting, and decrease after eating [3]; ghrelin decreases energy expenditure and promotes weight gain [4]. In contrast, leptin produced primarily by adipocytes, reduces appetite and increases energy utilization [5]. The gastric epithelium expresses both ghrelin and leptin (and their receptors) [6, 7]; inflammation can modify their production [8, 9].

*Helicobacter pylori* colonizes the human stomach and interacts with host tissues [10]. The present inventors have hypothesized that gastric *H. pylori* colonization affects the physiologic regulation of gut hormones involved in food intake, energy expenditure, and body weight maintenance. The hormones that affect overall metabolic function include ghrelin, leptin, amylin, insulin, active glucagon-like peptide-1, gastric inhibitory polypeptide, peptide YY, and pancreatic polypeptide. As disclosed herein, clinically indicated *H. pylori* eradication was used to evaluate the effect of *H. pylori* on meal-associated changes in ghrelin, leptin, and the other specified insulinotropic and digestive hormones, and to assess post-eradication changes in body mass index.

Methods

Study Population.

Adults ≥18 years of age undergoing routine upper endoscopy for any indication at the ambulatory endoscopy unit at the New York campus of the VA New York Harbor Healthcare System were prospectively recruited, as described [9, 14]. The Institutional Review Board approved the study protocol, and written informed consent was obtained from all participants. Participants were excluded if they had a history of esophageal or gastric varices, prior gastric surgery, known coagulopathy, had treatment with corticosteroids or other immunomodulating drugs in the month prior to enrollment, or if they had been treated to eradicate *H. pylori*.

Clinical Evaluation and Specimen Collection.

Each patient had a history and physical examination, and fasted for 12-hours overnight prior to the endoscopy. Demographic and clinical information, including assessment of dyspeptic symptoms, was collected via a standardized questionnaire administered by trained interviewers at the time of study entry. Ethnic designation was self-reported by participants as White Non-Hispanic, Black Non-Hispanic, Hispanic, or Asian. Participants wore light clothing without shoes; height and weight were measured using the same column scale with a telescopic height rod, and BMI calculated. Between 8 am and 10 am, 15 ml of blood was collected in EDTA-coated tubes from the fasting patients prior to endoscopy. All samples were centrifuged, and stored as serum at −20 C, until examined.

Endoscopy.

Complete endoscopic evaluation of the upper gastrointestinal tract was performed in standard fashion to the $2^{nd}$ portion of the duodenum, after intravenous administration of meperidine and midazolam, as described [14]. Gastric inflammation was graded using the Sydney-Houston system [15]. Using standard forceps, two biopsies each were obtained from the gastric antrum, body, and fundus in accordance with the updated Sydney classification; two additional antral biopsies were used for rapid urease testing.

Histological Analysis.

One biopsy specimen from each of the three sites was fixed in 10% formalin, embedded in paraffin, and 5 μm consecutive sections obtained for histologic staining. A single experienced GI pathologist (Z. P.) blinded to the data, graded the extent of gastritis and intestinal metaplasia on a scale of 0 to 3+ according to the Sydney classification [16]. Active gastritis refers to the presence of neutrophils in the histopathology, and chronic active reflects both neutrophils and mononuclear cells. For active gastritis, total score <2 was defined as "low" while ≥2 was defined as "high". *H. pylori* was detected using the cresyl violet stain for the identification of spiral or curved-shaped organisms near the mucous layer [17].

*H. pylori* Status Determination.

Along with histologic evaluation and the rapid urease assays, *H. pylori* was assessed using one other tissue-based method (bacteriologic culture, as described) [18], and by two serologic methods. For culture, gastric biopsies were placed immediately in normal saline at 4° C. and coarsely homogenized in 250 μl of normal saline. From this suspension, 50-μl aliquots were inoculated onto trypticase soy agar plates with 5% sheep blood, 50 μl of Skirrows medium and incubated for 96 h under microaerobic conditions, as described. *H. pylori* cells were identified as pleiomorphic, curved, gram-negative bacilli that were oxidase, urease, and catalase positive. Serum samples were examined by ELISA for IgG antibodies to *H. pylori* whole cell and CagA antigens, with results expressed as OD ratios relative to laboratory standards, as described [19, 20]. Subjects were considered *H. pylori*-positive if positive by histologic examination or culture, or if positive by rapid urease assay, and by IgG antibodies to *H. pylori* group or CagA antigens. Subjects were considered indeterminate for *H. pylori* if only the rapid urease test or one serological test was positive [9].

Test Meal.

Following recovery from endoscopy-related sedation, all patients ate a high-protein non-commercial meal averaging 806 calories. The contents of the meal were selected with the guidance of a trained nutritionist to provide 72 g carbohydrate, 71 g protein, and 26 g fat. Each food tray contained 1 hard boiled egg, 35 g of cereal with raisins, 237 ml Ensure (Abbott laboratories, Abbott Park, Ill.), 236 ml cranberry juice, 236 ml 2% milk, 30 ml sugar-free protein supplement, 116 ml coffee. Given that the trough that occurs in serum ghrelin levels occurs one hour postprandially [3], 15 ml of blood was collected one hour after completing the meal, and processed as above.

*H. pylori* Eradication Therapy.

Patients who tested positive for *H. pylori* were offered a 14-day twice-daily regimen [amoxicillin 1000 mg, clarithromycin 500 mg, and a proton pump inhibitor (PPI; omeprazole 20 mg, rabeprazole or esomeprazole 40 mg)][21]. Seven patients who had two positive serologic tests were treated to eradicate *H. pylori* after further confirmation with the $^{13}$C Urea Breath Test while off antisecretory medications. One penicillin-allergic patient received metronidazole [500 mg twice a day] instead of amoxicillin. In accordance with current guidelines [22], *H. pylori* eradication was ascertained using the $^{13}$C Urea Breath Test, according to the manufacturer's instructions (Meretek Diagnostics, Rockville, Md.) ≥8 weeks after treatment ended. At that time blood (15 ml) was again collected after fasting and 1 hour after a standardized meal. Patients who failed eradication were treated for 14 days with bismuth subsalicylate (525 mg four times a day), combined with a twice daily regimen [tetracycline (500 mg), metronidazole (500 mg), and PPI][21]. The $^{13}$C Urea Breath Test was repeated in all patients who completed rescue therapy. If not clinically indicated, antisecretory medications were not continued beyond the treatment period necessary for eradication.

Metabolic Tests.

A multi-hormone EIA panel (Catalogue HGT-68K; Millipore Corp., Billerica Mass.) was used to quantify eight gut hormones that are important regulators of food intake [1, 3, 23], energy expenditure [24], and body weight [25] via the gut-brain axis: acylated (active) ghrelin, leptin, active amylin, insulin, active glucagon-like peptide-1 (GLP-1), total gastric inhibitory polypeptide (GIP), total peptide YY (PYY), and pancreatic polypeptide (PP). There is a significant correlation between this assay and a standard enzyme linked immunoassay (EIA) for leptin (r=0.57, p=0.004). Similarly, the correlation with a standard ghrelin EIA was found to be significant [r=0.37; p=0.018]. The intra- and inter-assay variabilities ranged between 11% and 19%, respectively, according to the manufacturer, and for the ghrelin assay no cross reactivity exists with desacyl ghrelin. All tests were performed in duplicate on coded samples. An enzyme-linked immunosorbent assay (R&D Systems, Minneapolis Minn.) also was used to measure serum leptin levels, as described. The precision of the leptin assay is 94.6-96.5% and the minimum detectable level is 7.8 pg/ml [9, 14]. The leptin concentrations obtained using the multi-hormone panel and the specific EIA were correlated, with r=0.84 (p<0.001).

Statistical Analysis.

Continuous variables were compared using the t-test, or ANOVA method, and pair-wise analyses (e.g., pre-meal vs. post-meal, baseline vs. eradicated) were performed using non-parametric tests (Wilcoxon's signed rank test, Mann-Whitney U test), as appropriate. Data are expressed as mean±SD, or median and interquartile range ($25^{th}$-$75^{th}$ percentile). Categorical variables were compared using the Chi-squared test with Yates' correction or using Fisher's exact test. Spearman correlation coefficients were calculated for the relationship of leptin and ghrelin to BMI. Corrections were made in instances of multiple comparisons using techniques such as Tukey's range test. Based on previous findings showing 75% increase in fasting ghrelin after *H. pylori* eradication [13], our study was powered to allow for the detection of at least a 30% difference in ghrelin levels following successful eradication of 15 patients. Statistical analysis was performed using SPSS software version 16.0 for Macintosh (SPSS Inc., Chicago, Ill.); a two-tailed p-value of <0.05 was considered significant.

Symptom Evaluation.

Clinical gastroesophageal reflux disease (GERD) was defined as the presence of heartburn, regurgitation, or dysphagia [47], occurring at least weekly in the 4 weeks prior to enrollment. A standardized questionnaire was used to grade each symptom on a scale of 0 to 3. Dyspepsia was defined as the presence of chronic or recurrent abdominal pain in the center of the upper abdomen. The validated Severity of Dyspepsia Assessment (S.O.D.A.) questionnaire [31] was used to grade pain intensity, non-pain symptoms, and general satisfaction before and after treatment to eradicate H. pylori.

Results

Patient Demographic and Clinical Characteristics.

Figure 16:
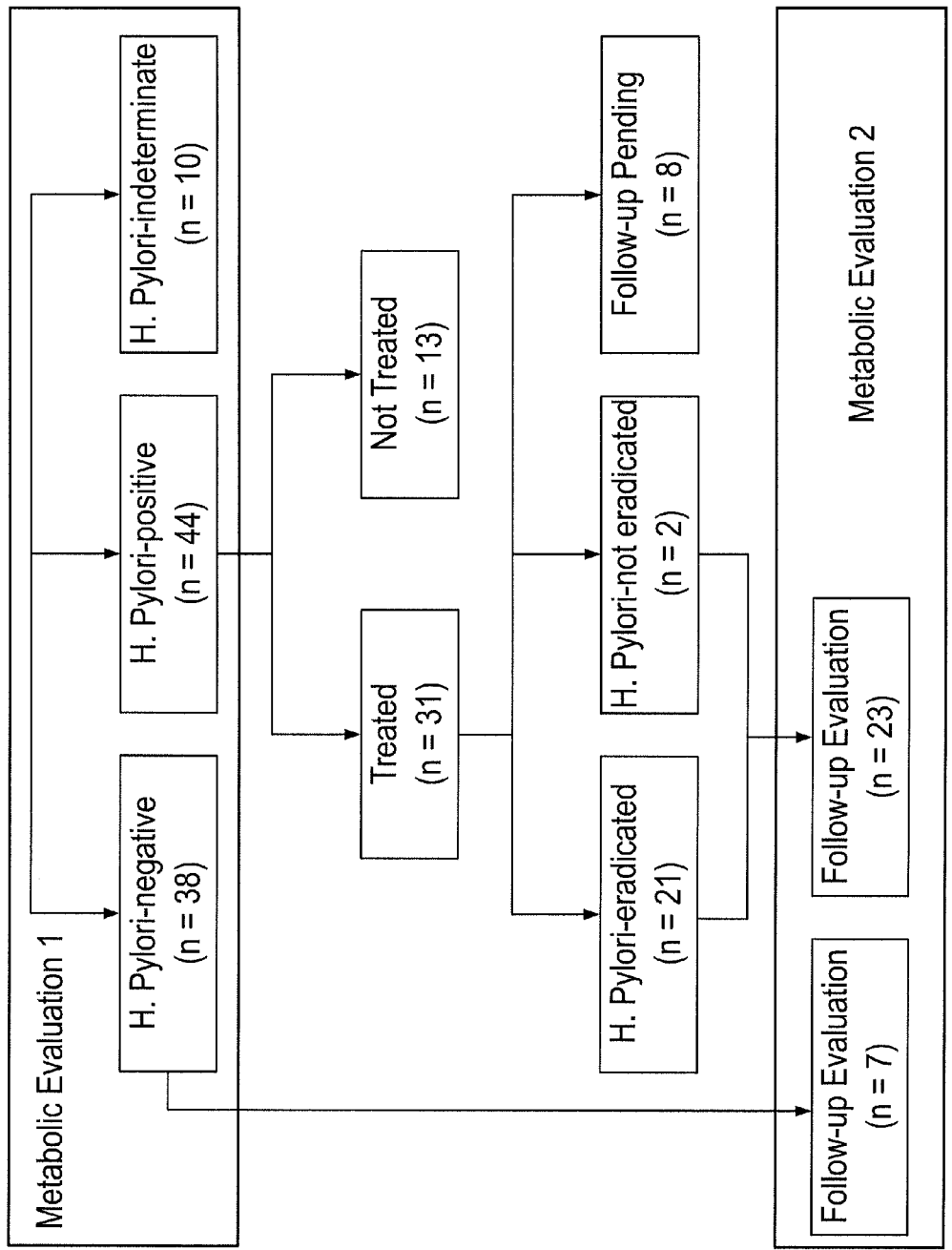
FIG. 16 is a schematic representation of enrollment and classification of 92 study participants. All study participants had an initial metabolic evaluation, and a second evaluation was provided to those who completed eradication therapy. The second evaluation also was offered to those who were initially negative, to serve as a control group.

92 patients were enrolled who completed the test meal protocol, as shown in FIG. 16. Based on histologic, culture, and serologic results, 38 patients were categorized as H. pylori-negative, 44 as H. pylori-positive, and 10 were indeterminate (Table 2).

and persistent heartburn in the H. pylori-indeterminate group; PPI use occurred in 46% of the entire study group. Endoscopic findings did not differ significantly between the groups. There were no significant changes in the maintenance use of antisecretory medications between baseline and follow-up examinations. The H. pylori-indeterminate group was excluded from subsequent analyses.

The H. pylori-negative and -positive groups did not differ significantly in age, ethnicity, PPI use, gender, or prevalence of upper abdominal symptoms (Table 2), but they differed in extent of acute gastritis (Table 3).

TABLE 2

Demographic and clinical characteristics of the 92 study patients, according to H. pylori status.

| Characteristic | H. pylori-negative (N = 38) | H. pylori-indeterminate (N = 10) | H. pylori-positive (N = 44) | Comparison of H. pylori-negative and H. pylori-positive subjects (p-value) |
|---|---|---|---|---|
| Mean age (years) ± SD | 65 ± 13 | 70 ± 6 | 64 ± 14 | 0.84[b] |
| Male, n (%) | 36 (95) | 10 (100) | 43 (98) | 0.47[c] |
| Race/ethnicity, n (%) | | | | 0.22[c] |
| White, non-Hispanic | 19 (50) | 4 (40) | 13 (30) | |
| Black, non-Hispanic | 13 (34) | 3 (30) | 18 (41) | |
| Hispanic | 5 (13) | 3 (30) | 12 (27) | |
| Asian | 1 (3) | 0 (0) | 1 (2) | |
| Mean BMI (kg/m²) ± SD | 26.4 ± 4 | 26.0 ± 3 | 29.4 ± 5 | 0.008[b] |
| PPI use, n (%)[a] | 15 (40) | 9 (90) | 18 (41) | 0.54[c] |
| Diabetes, n (%) | 7 (18) | 3 (30) | 14 (32) | 0.17[c] |

[a]PPI = proton pump inhibitor
[b]Student's t-test;
[c]Chi-Squared test

Compared to H. pylori-negative patients baseline BMI was significantly higher among H. pylori-positive patients. The prevalence of diabetes was also higher among H. pylori-positive compared to H. pylori-negative patients, however this difference did not reach statistical significance. The most common indication for endoscopy in both the H. pylori-negative and H. pylori-positive patients was heme-positive stool,

TABLE 3

Histologic score at three gastric sites among 38 H. pylori negative and 44 H. pylori positive subjects[a]

| | | Histologic score (Mean ± SD) | | |
|---|---|---|---|---|
| Site | | H. pylori-negative (n = 38) | H. pylori-positive (n = 44) | P value[b] |
| Antrum | Active gastritis | 0 ± 0 | 0.68 ± 0.25 | 0.12 |
| | Chronic active gastritis | 0.29 ± 0.17 | 0.82 ± 0.97 | <0.001 |
| | Intestinal metaplasia | 0.29 ± 0.17 | 0.19 ± 0.49 | 0.84 |
| | Atrophy | 0.09 ± 0.3 | 0.35 ± 0.60 | 0.37 |
| Body | Active gastritis | 0 ± 0 | 0.12 ± 0.50 | 0.17 |
| | Chronic active gastritis | 0.03 ± 0.17 | 0.48 ± 0.67 | <0.001 |
| | Intestinal metaplasia | 0 ± 0 | 0.07 ± 0.34 | 0.22 |
| | Atrophy | 0 ± 0 | 0.35 ± 0.70 | 0.33 |
| Fundus | Active gastritis | 0 ± 0 | 0.10 ± 0.49 | 0.24 |
| | Chronic active gastritis | 0 ± 0 | 0.58 ± 0.71 | <0.001 |
| | Intestinal metaplasia | 0 ± 0 | 0.02 ± 0.16 | 0.36 |
| All sites | Active gastritis (total) | 0.6 ± 0.34 | 2.1 ± 1.0 | <0.001 |

[a]Scoring based on the updated Sydney system [16].
[b]Mann-Whitney U test.

At baseline, the H. pylori-negative subjects had lower BMI measurements than did the H. pylori-positive group (26.4±4 vs. 29.4±5; p=0.008). Stratifying the 44 H. pylori-positive hosts according to cagA status of their strain did not reveal any significant differences in baseline demographic and clinical parameters.

Energy Homeostasis Hormones.

The study subjects varied substantially in baseline pre-meal (fasting) serum values for the eight studied hormones (Table 4).

TABLE 4

Levels of eight hormones related to energy homeostasis at the baseline evaluation of 82 subjects according to H. pylori status, and in relation to the test meal.

| | Median (IQR) hormone concentration (pg/ml), by baseline H. pylori status | | | | | | Comparison of H. pylori negative and H. pylori-positive subjects (p-value) | |
|---|---|---|---|---|---|---|---|---|
| | H. pylori-negative (n = 38) | | | H. pylori-positive (n = 44) | | | | |
| Hormone | Pre-meal | Post-meal | p[a] | Pre-meal | Post-meal | p[a] | Pre-meal | Post-meal |
| Amylin | 40 (14-66) | 58 (15-117) | 0.028 | 16 (14-76) | 40 (15-104) | 0.004 | 0.78 | 0.78 |
| Insulin | 285 (161-459) | 957 (390-1,993) | <0.001 | 295 (139-460) | 952 (475-1,735) | <0.001 | 0.84 | 0.84 |
| Ghrelin | 1,321 (23-3,306) | 783 (24-2,243) | 0.001 | 1,623 (8-3,504) | 248 (12-1,329) | <0.001 | 0.91 | 0.85 |

TABLE 4-continued

Levels of eight hormones related to energy homeostasis at the baseline evaluation of 82 subjects according to *H. pylori* status, and in relation to the test meal.

| | Median (IQR) hormone concentration (pg/ml), by baseline *H. pylori* status | | | | | | Comparison of *H. pylori* negative and *H. pylori*-positive subjects (p-value) | |
|---|---|---|---|---|---|---|---|---|
| | *H. pylori*-negative (n = 38) | | | *H. pylori*-positive (n = 44) | | | | |
| Hormone | Pre-meal | Post-meal | p<sup>a</sup> | Pre-meal | Post-meal | p<sup>a</sup> | Pre-meal | Post-meal |
| GIP | 17 (6-31) | 121 (31-234) | <0.001 | 15 (8-30) | 130 (72-237) | <0.001 | 0.69 | 0.69 |
| GLP-1 | 23 (9-70) | 29 (9-72) | 0.87 | 27 (9-82) | 18 (9-66) | 0.46 | 0.65 | 0.65 |
| Leptin | 2,190 (961-7,085) | 2,840 (1,210-6,135) | 0.003 | 4,260 (1,850-7,540) | 5,680 (1,875-9.537) | 0.001 | 0.14 | 0.17 |
| PP | 72 (39-117) | 135 (77-177) | <0.001 | 64 (30-136) | 136 (69-209) | <0.001 | 0.81 | 0.81 |
| PYY | 49 (33-78) | 74 (52-110) | 0.001 | 48 (27-72) | 68 (47-95) | <0.001 | 0.64 | 0.64 |

Figure 17:
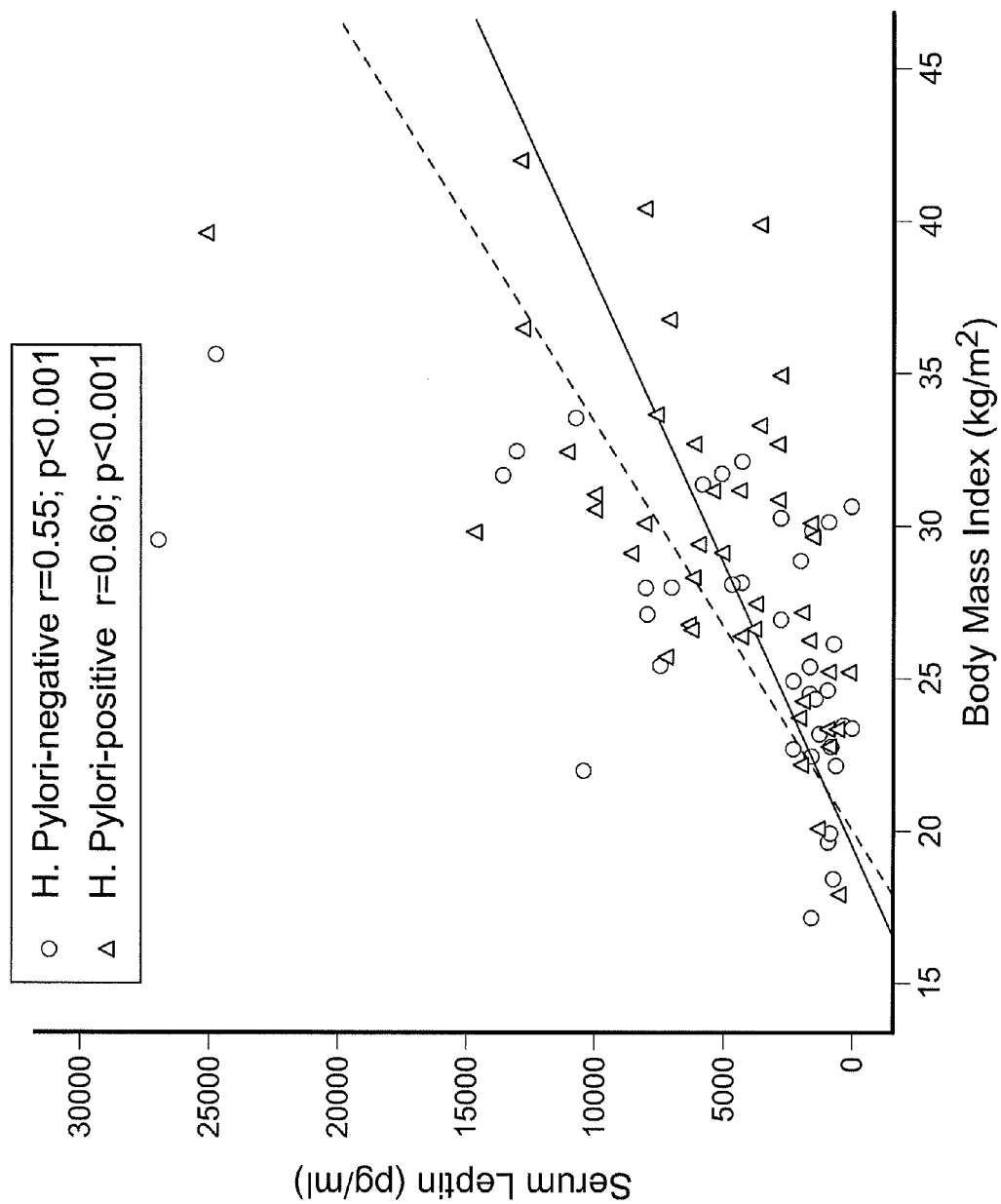
FIG. 17 shows relationship of baseline BMI and baseline pre-meal leptin in 38 $H.$ $pylori$-negative (○) and 44 $H.$ $pylori$-positive (Δ) subjects. Correlation is by linear regression analysis ($H.$ $pylori$-negative r=0.55, p<0.001; $H.$ $pylori$-positive r=0.60, p<0.001).

<sup>a</sup>Wilcoxon's signed rank test comparing pre-meal and post-meal values within *H. pylori* groups
<sup>b</sup>Mann-Whitney U test, comparing values for *H. pylori*-negative and *H. pylori*-positive subjects Serum leptin values correlated with BMI, for both the *H. pylori*-negative and *H. pylori*-positive subjects (FIG. 17). There were no significant differences according to *H. pylori* status in pre-meal leptin, amylin, insulin, ghrelin, GIP, GLP-1, PP, and PYY levels (Table 4). There were hormonal responses to the test meal; post-meal amylin levels rose physiologically [26] in both the *H. pylori*-negative and *H. pylori*-positive subjects (Table 4). Similarly, there were significant post-meal increases in the levels of insulin, GIP, PP, and PYY, in both the *H. pylori*-negative and *H. pylori*-positive groups. Ghrelin values diminished following the meal, while leptin values rose significantly in both groups. The disclosed observations are consistent with the expected meal-associated hormonal changes, with no significant differences between the *H. pylori*-positive and -negative subjects, as well as when data were normalized.

Effects of *H. pylori* Eradication.

Treatment for *H. pylori* was accepted by 31 (70.5%) of the 44 subjects in whom it was clinically indicated; 23 completed all of our assessments and eradication was successful in 21 (91%) (FIG. 16). The 21 subjects were representative of the entire group of 44 who were initially *H. pylori*-positive, with similar meal-associated hormone changes at baseline (compare Table 4 and Table 5).

TABLE 5

Levels of eight hormones related to energy homeostasis, and BMI in 21 subjects, according to *H. pylori* eradication status.

| | Median (IQR) hormone concentration (pg/ml), before and after *H. pylori* eradication | | | | | | Comparison of values at baseline and after eradication (p-value) | |
|---|---|---|---|---|---|---|---|---|
| | Baseline | | | Eradicated | | | | |
| Hormone | Pre-meal | Post-meal | p<sup>b</sup> | Pre-meal | Post-meal | p<sup>b</sup> | Pre-meal | Post-meal |
| Amylin | 15 (14-43) | 19 (15-54) | 0.046 | 16 (15-50) | 36 (15-106) | 0.008 | 0.25 | 0.16 |
| Insulin | 243 (129-414) | 584 (462-1,475) | <0.001 | 265 (139-558) | 763 (430-2,100) | <0.001 | 0.39 | 0.28 |
| Ghrelin | 1,024 (7-3,461) | 231 (7-1,329) | 0.004 | 1,710 (27-4,573) | 1,586 (13-3,360) | 0.12 | 0.51 | 0.005 |
| GIP | 15 (5-29) | 107 (29-214) | 0.001 | 27 (9-54) | 82 (41-282) | 0.001 | 0.82 | 0.85 |
| GLP-1 | 28 (10-56) | 16 (9-59) | 0.51 | 36 (12-89) | 45 (14-91) | 0.95 | 0.11 | 0.04 |
| Leptin | 4,260 (1,890-6,649) | 5,690 (1,765-11,350) | 0.02 | 6,605 (3,517-14,600) | 7,400 (4,120-17,925) | 0.02 | 0.001 | <0.001 |
| PP | 63 (18-113) | 107 (44-204) | 0.005 | 79 (26-153) | 112 (45-172) | 0.001 | 0.31 | 0.23 |
| PYY | 39 (27-82) | 70 (48-98) | 0.002 | 61 (34-90) | 70 (47-137) | 0.001 | 0.02 | 0.34 |

<sup>a</sup>p-values < 0.05 are indicated in bold
<sup>b</sup>Wilcoxon's signed rank test comparing pre-meal and post-meal values.
<sup>c</sup>Paired t-test comparing BMI at baseline to after *H. pylori* eradication.

Figure 18A:
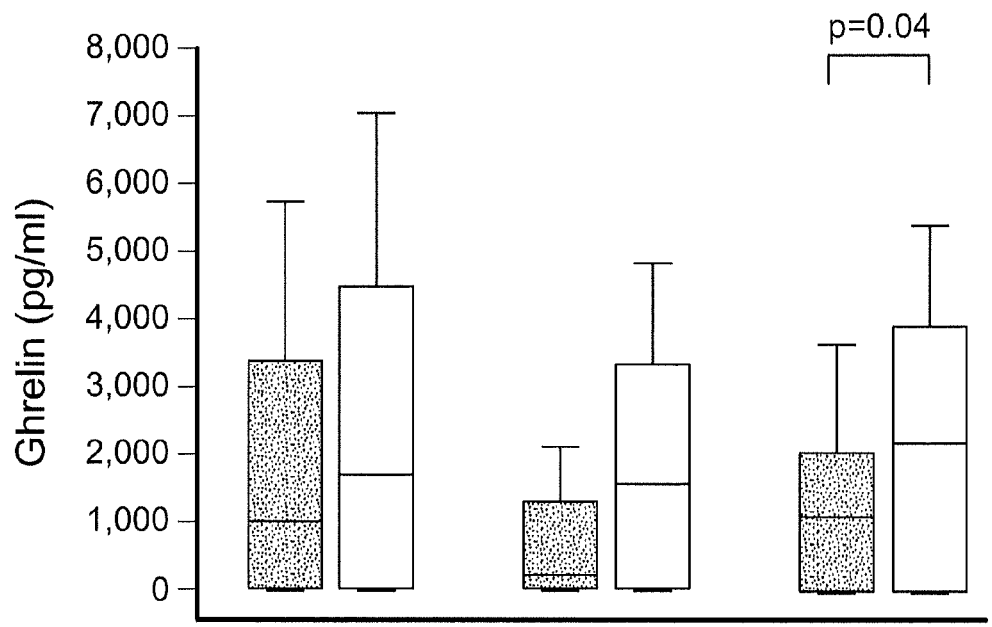
FIGS. 18A-B show comparison of $H.$ $pylori$+ persons at baseline, and then after eradication of $H.$ $pylori$. A standardized meal was administered to 21 subjects, and pre-meal, post-meal, and integrated values (mean of pre-meal and post-meal) were calculated for acyl-ghrelin (Panel A) and leptin (Panel B). ($H.$ $pylori$+ ▒, Eradicated □). Boxes indicate median and interquartile range, and bars indicate minimum and maximum values. P-values represent significant (<0.05) differences between the $H.$ $pylori$+ and post-eradication samples.
Figure 18B:
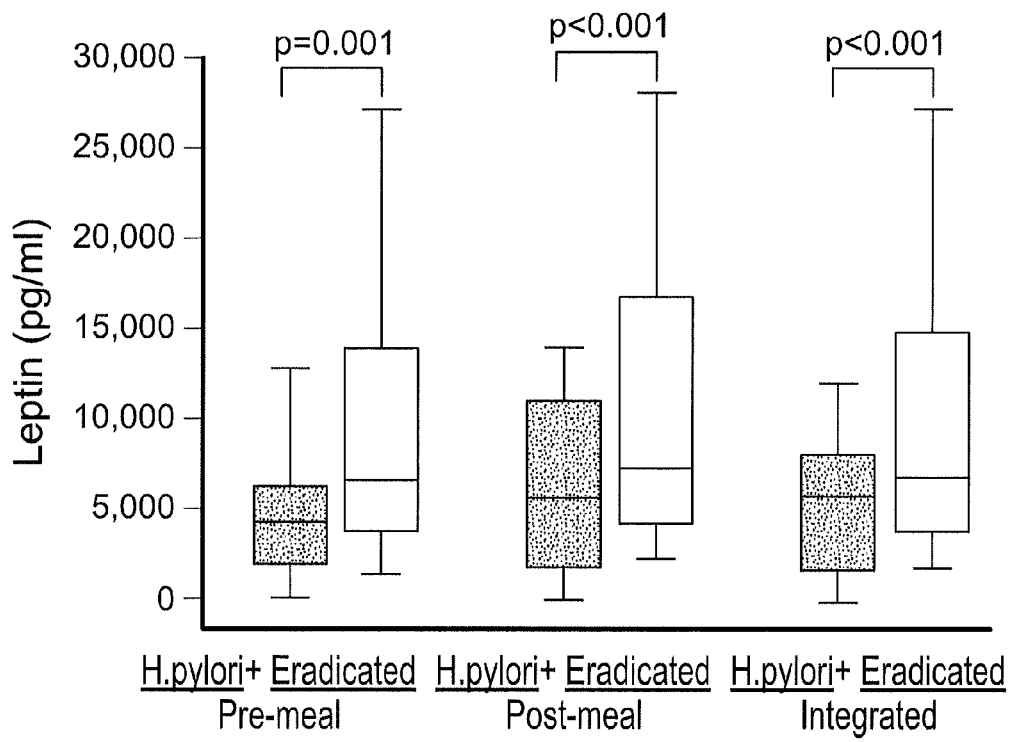

Following *H. pylori* eradication, the meal-associated increases in amylin, insulin, GIP, PP, and PYY remained significant (Table 5). Compared to baseline, post-meal levels of the incretin GLP-1 were significantly increased following *H. pylori* eradication. Pre-meal ghrelin levels did not significantly differ between baseline and post-eradication (Table 5); however, following *H. pylori* eradication, post-meal ghrelin levels did not substantially decrease (FIG. 18A). After *H. pylori* eradication, pre-meal, post-meal, and integrated leptin levels rose significantly (FIG. 18B), and remained significantly correlated with BMI (r=0.69, p<0.01). PPI use did not account for the changes in ghrelin and leptin levels from baseline to follow-up [27, 28].

Figure 19A:
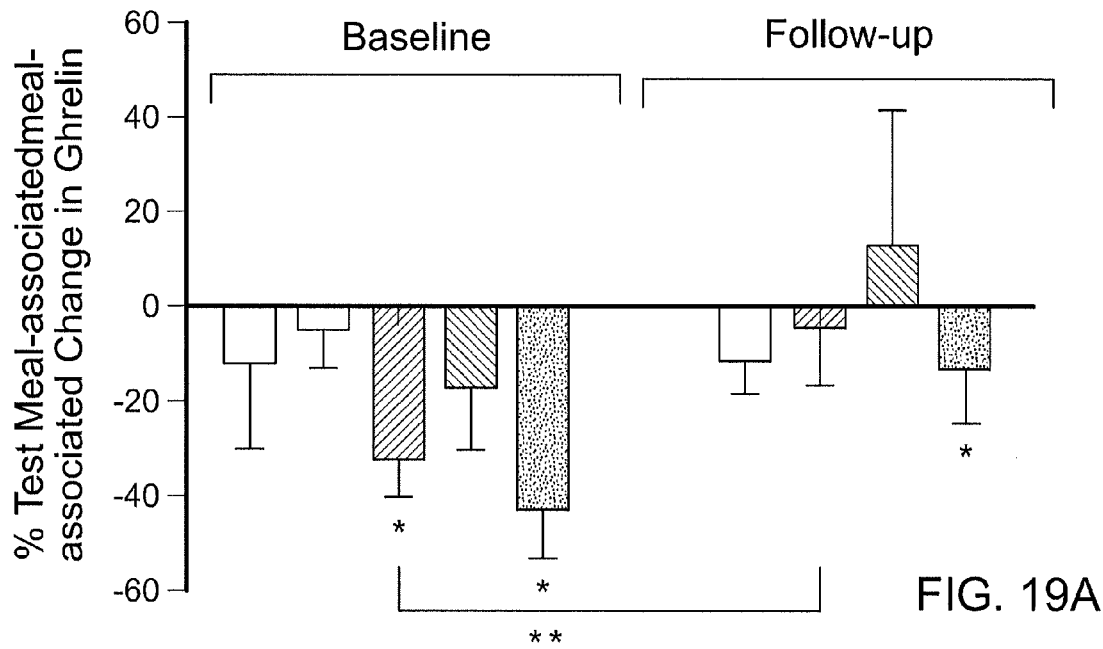
FIGS. 19A-B show comparison of test-meal induced changes in plasma acyl-ghrelin and leptin levels according to $H.$ $pylori$ at baseline and after eradication. Data are for seven $H.$ $pylori$-negative, 21 $H.$ $pylori$-positive subjects including eight $H.$ $pylori$+cagA− and 13 $H.$ $pylori$+cagA+) subjects. (*P<0.05, comparing either pre-meal to post-meal values, or **comparing the first and second evaluations). Data also are shown for all of the 38 $H.$ $pylori$-negative subjects at baseline, for comparison with the subset who also had follow-up studies. Panel A: Ghrelin levels. Panel B: Leptin Levels.
Figure 19B:
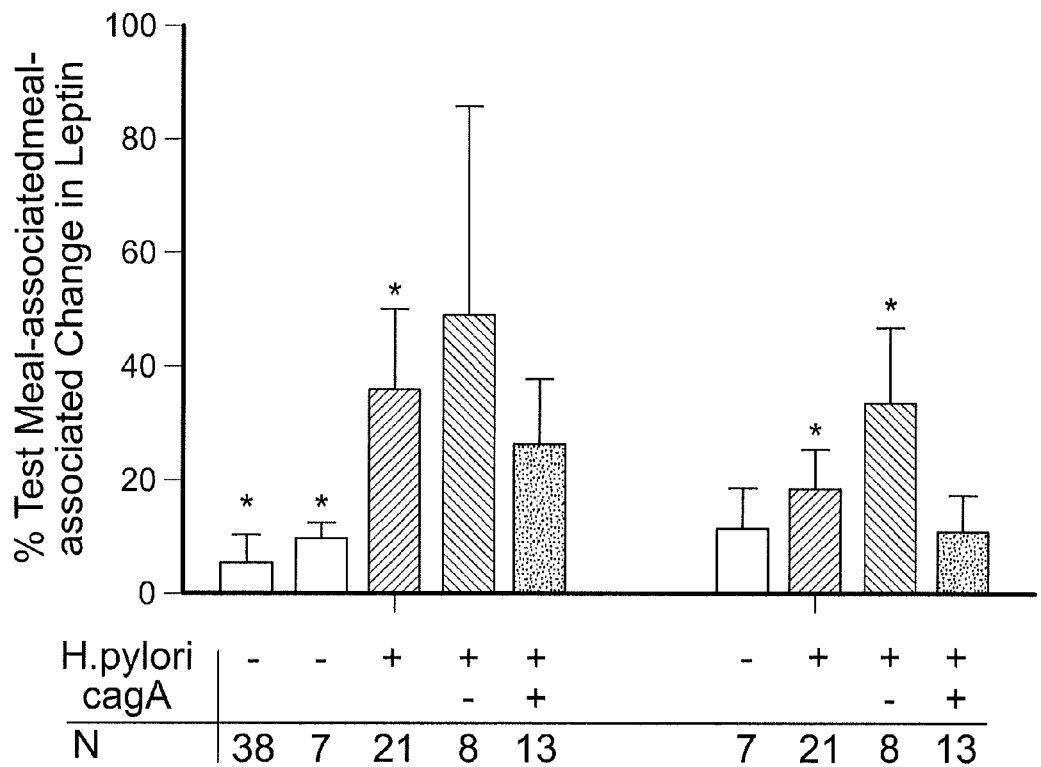

Since the initial measurements were performed on the day of endoscopy while the second measurements were not, it was considered that gastric distension might have influenced measurements between the two time-points. This potential bias was addressed by also evaluating seven subjects who were *H. pylori* negative at a second time-point. The same test meal, and metabolic evaluations were repeated in the seven *H. pylori*-negative subjects at baseline and after follow-up (median 14 months). This control group had no significant changes in the eight measured adipokines between the two time-points, and no changes in meal-associated physiology (FIG. 19). In the *H. pylori*-positive subjects at baseline, ingestion of the test meal led to a 32±9% decrease (p=0.004) in ghrelin with somewhat larger declines in persons with cagA-positive strains than in those with cagA- negative strains. Data from the 38 *H. pylori*-negative subjects and the subset of seven who had long-term follow-up also showed similar trends (FIG. 19A). However, after *H. pylori* eradication, post-meal ghrelin levels only fell minimally (4±12%; p=NS); the difference in meal-associated responses comparing baseline and post-eradication (32% vs. 4%) was significant (p=0.05). At baseline, leptin levels in both the *H. pylori*-positive and *H. pylori*-negative subjects significantly increased after the test meal (FIG. 19B). The meal-associated rise in leptin after eradication (19±7%), remained significant (p=0.02). Following *H. pylori*-eradication in subjects previously colonized with cagA- positive strains, the meal-associated increase in PP was significantly lower than expected (27% vs. -13%; p=0.01).

Meal-Associated Ghrelin Physiology in Relation to Baseline Gastric Histology.

In the group from whom *H. pylori* was eradicated, the severity of histologic inflammation in the fundus at baseline was negatively correlated with pre-meal ghrelin (r=-0.57, p=0.01) [29, 30]. Subjects with more active gastritis had higher pre-meal ghrelin levels at baseline, and greater meal-associated changes post-eradication (Table 6). Eradication-related changes in ghrelin physiology also correlated with the anatomic location of gastritis; subjects with antral gastritis only showed the largest increases in values obtained pre-meal, post-meal, and across the meal (Table 7). These data provide evidence that both location and extent of gastric inflammation affects ghrelin secretion, but similar associations were not found with reference to leptin physiology.

TABLE 6

Comparison of baseline and post-eradication meal-associated ghrelin profile in 21 originally *H. pylori*-positive subjects, according to severity of baseline histologic gastritis.

| | Median [IQR] ghrelin concentration (pg/ml) | | |
|---|---|---|---|
| | Low active gastritis[b] (n = 7) | High active gastritis[b] (n = 14) | P value[c] |
| Meal status at baseline | | | |
| Pre-meal | 516 [7-1580] | 3173 [989-3899] | 0.04 |
| Post-meal | 80 [7-538] | 925 [183-1378] | 0.12 |
| Normalized % change[a] | -8 [-47-0] | -67 [-74-3] | 0.47 |
| Meal status post-eradication | | | |
| Pre-meal | 1342[d] [11-5447] | 1877 [447-3726] | 0.62 |
| Post-meal | 1594[d] [11-3236] | 1961 [435-3910] | 0.39 |
| Normalized % change[a] | 0 [-35-0] | -19 [-28--1] | 0.02 |

[a]Normalized % change = ([Post-meal] − [Pre-meal])/[Pre-meal]*100.
[b]Summation of inflammation scores for all sites allowed for the categorization of low (<2) vs high (>2) active gastritis.
[c]Wilcoxon's signed rank test.
[d]$p < 0.05$; compared to baseline value

TABLE 7

Meal-associated changes in ghrelin profile in 28 subjects[a] who had follow-up evaluation, according to anatomical distribution of histologic gastritis at baseline

| Change from baseline | Median [IQR] percent change in ghrelin concentration from baseline to follow-up | | | |
|---|---|---|---|---|
| to eradicated [normalized] | No gastritis (n = 10) | Antral gastritis (n = 6) | Pan-gastritis (n = 12) | P value[d] |
| Pre-meal[b] | -98 [-99--16] | 109 [59-244] | 7 [-62-46] | 0.01 |
| Post-meal[b] | -98 [-99--1] | 494 [240-1300] | 135 [-22-380] | 0.04 |
| Meal effect[c] | -100 [-309--100] | 33 [24-143] | -145 [-167--62] | 0.02 |

[a]Includes 21 *H.pylori*-positive and 7 *H. pylori*-negative subjects
[b]Normalized % change = ((Eradicated − Baseline)/Baseline)*100
[c]Change in meal effect = Normalized eradicated meal-associated change − Normalized baseline meal-associated change
[d]Kruskal-Wallis test.

Body Mass Index in Relation to *H. pylori* Status.

Figure 20:
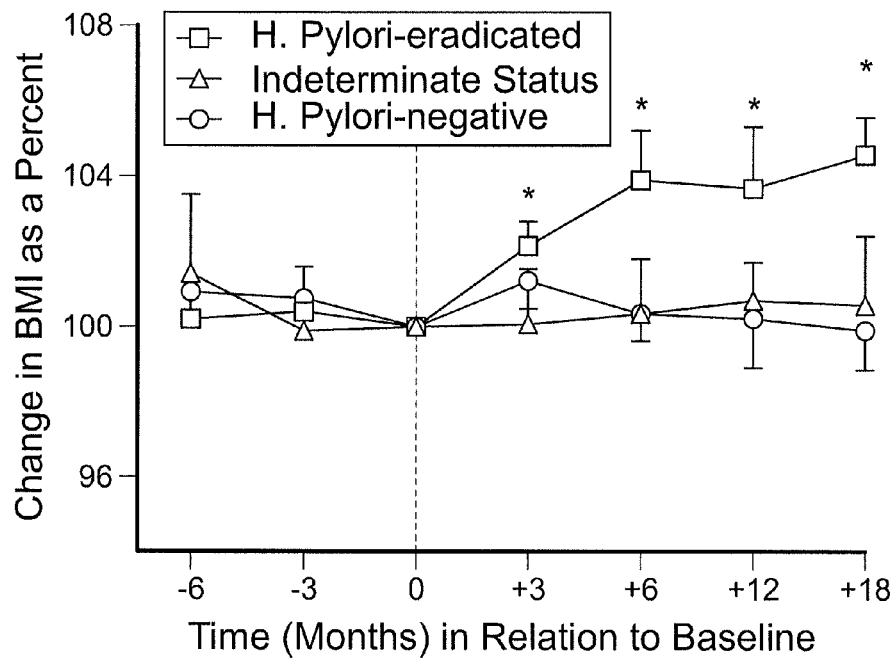
FIG. 20 shows change in BMI in 69 study subjects over a 2-year period. BMI is calculated relative to the baseline (at time 0), and is shown from 6 months prior to baseline and during 18 months of follow-up in 38 $H.$ $pylori$-negative, 21 $H.$ $pylori$-eradicated, and 10 subjects who were $H.$ $pylori$-indeterminate at baseline (*p<0.05, comparing time 0 to other follow-up months).

Since baseline BMI was higher for the *H. pylori*-eradicated group, this potential bias was addressed by comparing individuals to themselves in longitudinal pair-wise analyses. During the six months prior to study initiation, BMI did not change substantially in any of the study subjects (FIG. 20). During 18 months (IQR 12, 24) of follow-up, BMI did not change significantly in subjects who at baseline were either *H. pylori*-negative or *H. pylori*-indeterminate. In contrast, in the *H. pylori*-eradicated group, BMI progressively and significantly increased, reaching 105±2% by 18 months of follow-up (p=0.008); baseline *H. pylori* cagA status did not predict results (p=0.58). The change in BMI relative to baseline also was significantly greater at 3, 6, and 12 months following eradication compared to the *H. pylori*-negative group. The change in pre-meal ghrelin from baseline following *H. pylori* eradication, was positively correlated with the change in BMI at 3 months (r=0.78; p=0.005), 6 months (r=0.86; p=0.001), and 12 months [r=0.82; p=0.001 (FIG. 21)], and 18 months (r=0.87; p=0.001).

Dyspepsia Symptoms at Baseline and Follow-Up.

Since weight gain could reflect decreased dyspeptic symptoms following *H. pylori* eradication, dyspeptic symptoms at baseline and post-eradication were assessed. A validated multidimensional assessment tool [31] was used to evaluate three scales: pain intensity, non-pain symptoms, and satisfaction with dyspepsia-related health. At baseline, the 38 *H. pylori*-negative and 44 *H. pylori*-positive subjects did not differ significantly in median pain, non-pain, and satisfaction scores. Among the 21 patients from whom *H. pylori* was eradicated, there were no significant differences between baseline and follow-up pain scores [Median (IQR) 9 (2-23) vs. 6 (2-15); p=0.86], non-pain scores [13 (12-16) vs. 10 (10-18); p=0.28], or satisfaction scores [13 (10-23) vs. 19 (12-20); p=0.29]. Thus, the observed increase in BMI following eradication (FIG. 20) was not correlated with diminished dyspepsia that could increase appetite.

Discussion

Appetite-reducing hormones, such as amylin, insulin, GIP, GLP-1, PP, and PYY, produced in the small intestine and pancreas are important in mammalian energy homeostasis, [32-35], as is leptin which is produced mostly by adipocytes, but also by gastric chief cells [6]. Importantly, gastric oxyntic endocrine cells [36] account for 65-80% of the body's total ghrelin production. *H. pylori* colonization status has been correlated with circulating and gastric mucosal leptin levels, and with gastric mRNA expression and plasma levels of ghrelin [9, 37]. As demonstrated herein, *H. pylori* eradication has substantial effects on meal-associated changes in gastric hormones and energy balance.

Figure 21:
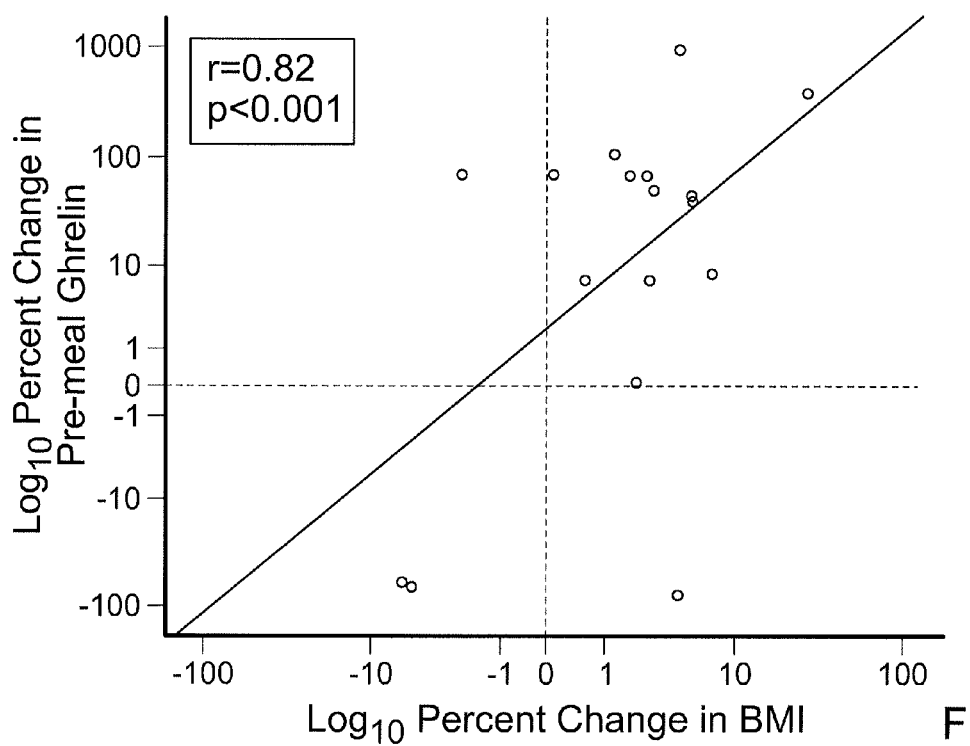
FIG. 21 shows correlation of changes in ghrelin and BMI post-$H.$ $pylori$ eradication. The ordinate shows the log 10 percent change in pre-meal ghrelin associated with eradication, and the abscissa shows changes in BMI at 12 months, relative to baseline in 17 $H.$ $pylori$-eradicated subjects (r=0.82, p<0.001).

The present study shows that following *H. pylori* eradication, there is blunting of the meal-associated physiologic reduction in circulating acyl-ghrelin, and there is long-term weight gain; in addition, changes in baseline acyl-ghrelin values and changes in BMI were linked (FIG. 21). Reflecting the observed weight gain, leptin levels pre-meal and post-meal ghrelin levels were significantly elevated after eradication and differed significantly from baseline values. It was also observed that *H. pylori* eradication was associated with preservation of meal-associated increases in amylin, insulin, GIP, PP, and PYY. Post-meal levels of the incretin GLP-1 were significantly increased following eradication compared to baseline. Based on the present study, there is no evidence that the weight gain associated with *H. pylori* eradication reflected improvement of dyspeptic symptoms as suggested previously [44].

In conclusion, the present study indicates that leptin and ghrelin physiology change and that BMI increases following *H. pylori* eradication. This study provides further evidence that gastric *H. pylori* is involved in the physiologic regulation of these hormones.

REFERENCES

1. Shintani M, Ogawa Y, Ebihara K, Aizawa-Abe M, Miyanaga F, Takaya K, Hayashi T, Inoue G, Hosoda K, Kojima M et al: Ghrelin, an endogenous growth hormone secretagogue, is a novel orexigenic peptide that antagonizes leptin action through the activation of hypothalamic neuropeptide Y/Y1 receptor pathway. *Diabetes* 2001, 50(2):227-232.
2. Schwartz M W, Seeley R J, Campfield L A, Burn P, Baskin D G: Identification of targets of leptin action in rat hypothalamus. *J Clin Invest* 1996, 98(5):1101-1106.
3. Cummings D E, Purnell J Q, Frayo R S, Schmidova K, Wisse B E, Weigle D S: A preprandial rise in plasma ghrelin levels suggests a role in meal initiation in humans. *Diabetes* 2001, 50(8):1714-1719.
4. Tschop M, Smiley D L, Heiman M L: Ghrelin induces adiposity in rodents. *Nature* 2000, 407(6806):908-913.
5. Halaas J L, Gajiwala K S, Maffei M, Cohen S L, Chait B T, Rabinowitz D, Lallone R L, Burley S K, Friedman J M: Weight-reducing effects of the plasma protein encoded by the obese gene. *Science* 1995, 269(5223):543-546.
6. Mix H, Widjaja A, Jandl O, Cornberg M, Kaul A, Goke M, Beil W, Kuske M, Brabant G, Manns M P et al: Expression of leptin and leptin receptor isoforms in the human stomach. *Gut* 2000, 47(4):481-486.
7. Gnanapavan S, Kola B, Bustin S A, Morris D G, McGee P, Fairclough P, Bhattacharya S, Carpenter R, Grossman A B, Korbonits M: The tissue distribution of the mRNA of ghrelin and subtypes of its receptor, GHS-R, in humans. *J Clin Endocrinol Metab* 2002, 87(6):2988.
8. Liew P L, Lee W J, Lee Y C, Chen W Y: Gastric ghrelin expression associated with *Helicobacter pylori* infection and chronic gastritis in obese patients. *Obes Surg* 2006, 16(5): 612-619.
9. Roper J, Francois F, Shue P L, Mourad M S, Pei Z, Olivares de Perez A Z, Perez-Perez G I, Tseng C H, Blaser M J: Leptin and ghrelin in relation to *Helicobacter pylori* status in adult males. *J Clin Endocrinol Metab* 2008, 93(6):2350-2357.
10. Atherton J C, Blaser M J: Coadaptation of *Helicobacter pylori* and humans: ancient history, modern implications. *J Clin Invest* 2009, 119(9):2475-2487.
11. Pacifico L, Anania C, Osborn J F, Ferrara E, Schiavo E, Bonamico M, Chiesa C: Long-term effects of *Helicobacter pylori* eradication on circulating ghrelin and leptin concentrations and body composition in prepubertal children. *Eur J Endocrinol* 2008, 158(3):323-332.
12. Azuma T, Suto H, Ito Y, Muramatsu A, Ohtani M, Dojo M, Yamazaki Y, Kuriyama M, Kato T: Eradication of *Helicobacter pylori* infection induces an increase in body mass index. *Aliment Pharmacol Ther* 2002, 16 Suppl 2:240-244.
13. Nwokolo C U, Freshwater D A, O'Hare P, Randeva H S: Plasma ghrelin following cure of *Helicobacter pylori*. *Gut* 2003, 52(5):637-640.
14. Francois F, Roper J, Goodman A J, Pei Z, Ghumman M, Mourad M, de Perez A Z, Perez-Perez G I, Tseng C H, Blaser M J: The association of gastric leptin with oesophageal inflammation and metaplasia. *Gut* 2008, 57(1):16-24.
15. Tytgat G N: The Sydney System: endoscopic division. Endoscopic appearances in gastritis/duodenitis. *J Gastroenterol Hepatol* 1991, 6(3):223-234.
16. Dixon M F, Genta R M, Yardley J H, Correa P: Classification and grading of gastritis. The updated Sydney System. International Workshop on the Histopathology of Gastritis, Houston 1994. *Am J Surg Pathol* 1996, 20(10): 1161-1181.
17. Goggin N, Rowland M, Imrie C, Walsh D, Clyne M, Drumm B: Effect of *Helicobacter pylori* eradication on the natural history of duodenal ulcer disease. *Arch Dis Child* 1998, 79(6):502-505.
18. Tummuru M K, Cover T L, Blaser M J: Cloning and expression of a high-molecular-mass major antigen of *Helicobacter pylori*: evidence of linkage to cytotoxin production. *Infect Immun* 1993, 61(5):1799-1809.

19. Perez-Perez G I, Dworkin B M, Chodos J E, Blaser M J: *Campylobacter pylori* antibodies in humans. *Ann Intern Med* 1988, 109(1):11-17.
20. Blaser M J, Perez-Perez G I, Kleanthous H, Cover T L, Peek R M, Chyou P H, Stemmermann G N, Nomura A: Infection with *Helicobacter pylori* strains possessing cagA is associated with an increased risk of developing adenocarcinoma of the stomach. *Cancer Res* 1995, 55(10):2111-2115.
21. Egan B J, Marzio L, O'Connor H, O'Morain C: Treatment of *Helicobacter pylori* infection. *Helicobacter* 2008, 13 Suppl 1:35-40.
22. Malfertheiner P, Megraud F, O'Morain C, Bazzoli F, El-Omar E, Graham D, Hunt R, Rokkas T, Vakil N, Kuipers E J: Current concepts in the management of *Helicobacter pylori* infection: the Maastricht III Consensus Report. *Gut* 2007, 56(6):772-781.
23. Zhang F, Chen Y, Heiman M, Dimarchi R: Leptin: structure, function and biology. *Vitam Horm* 2005, 71:345-372.
24. Zhou H, Yamada Y, Tsukiyama K, Miyawaki K, Hosokawa M, Nagashima K, Toyoda K, Naitoh R, Mizunoya W, Fushiki T et al: Gastric inhibitory polypeptide modulates adiposity and fat oxidation under diminished insulin action. *Biochem Biophys Res Commun* 2005, 335(3):937-942.
25. Aaboe K, Krarup T, Madsbad S, Holst J J: GLP-1: physiological effects and potential therapeutic applications. *Diabetes Obes Metab* 2008, 10(11):994-1003.
26. Lutz T A: Amylinergic control of food intake. *Physiol Behav* 2006, 89(4):465-471.
27. Kim B W, Lee B I, Kim H K, Cho Y S, Chae H S, Lee H K, Kim H J, Han S W: [Influence of long-term gastric acid suppression therapy on the expression of serum gastrin, chromogranin A, and ghrelin]. *Korean J Gastroenterol* 2009, 53(2):84-89.
28. Yamamoto T, Sanaka M, Anjiki H, Hattori K, Ishii T, Kuyama Y: No relationship between plasma desacyl-ghrelin levels and rabeprazole-related delay in gastric emptying: controlled study in healthy volunteers. *Drugs R D* 2008, 9(5):345-348.
29. Osawa H, Kita H, Ohnishi H, Nakazato M, Date Y, Bowlus C L, Ishino Y, Watanabe E, Shiiya T, Ueno H et al: Changes in plasma ghrelin levels, gastric ghrelin production, and body weight after *Helicobacter pylori* cure. *J Gastroenterol* 2006, 41(10):954-961.
30. Kawashima J, Ohno S, Sakurada T, Takabayashi H, Kudo M, Ro S, Kato S, Yakabi K: Circulating acylated ghrelin level decreases in accordance with the extent of atrophic gastritis. *J Gastroenterol* 2009, 44(10):1046-1054.
31. Rabeneck L, Cook K F, Wristers K, Souchek J, Menke T, Wray N P: SODA (severity of dyspepsia assessment): a new effective outcome measure for dyspepsia-related health. *J Clin Epidemiol* 2001, 54(8):755-765.
32. Batterham R L, Cowley M A, Small C J, Herzog H, Cohen M A, Dakin C L, Wren A M, Brynes A E, Low M J, Ghatei M A et al: Gut hormone PYY(3-36) physiologically inhibits food intake. *Nature* 2002, 418(6898):650-654.
33. Lassmann V, Vague P, Vialettes B, Simon M C: Low plasma levels of pancreatic polypeptide in obesity. *Diabetes* 1980, 29(6):428-430.
34. Wren A M, Seal U, Cohen M A, Brynes A E, Frost G S, Murphy K G, Dhillo W S, Ghatei M A, Bloom S R: Ghrelin enhances appetite and increases food intake in humans. *J Clin Endocrinol Metab* 2001, 86(12):5992.
35. Baggio L L, Drucker D J: Biology of incretins: GLP-1 and GIP. *Gastroenterology* 2007, 132(6):2131-2157.
36. Kojima M, Hosoda H, Date Y, Nakazato M, Matsuo H, Kangawa K: Ghrelin is a growth-hormone-releasing acylated peptide from stomach. *Nature* 1999, 402(6762):656-660.
37. Isomoto H, Ueno H, Nishi Y, Wen C Y, Nakazato M, Kohno S: Impact of *Helicobacter pylori* infection on ghrelin and various neuroendocrine hormones in plasma. *World J Gastroenterol* 2005, 11(11): 1644-1648.
38. Gunji T, Matsuhashi N, Sato H, Fujibayashi K, Okumura M, Sasabe N, Urabe A: *Helicobacter pylori* infection is significantly associated with metabolic syndrome in the Japanese population. *Am J Gastroenterol* 2008, 103(12): 3005-3010.
39. Tschop M, Wawarta R, Riepl R L, Friedrich S, Bidlingmaier M, Landgraf R, Folwaczny C: Post-prandial decrease of circulating human ghrelin levels. *J Endocrinol Invest* 2001, 24(6):RC19-21.
40. Blaser M J, Kirschner D: The equilibria that allow bacterial persistence in human hosts. *Nature* 2007, 449(7164): 843-849.
41. Adrian T E, Ferri G L, Bacarese-Hamilton A J, Fuessl H S, Polak J M, Bloom S R: Human distribution and release of a putative new gut hormone, peptide YY. *Gastroenterology* 1985, 89(5):1070-1077.
42. Feillet C A: Food for thoughts: feeding time and hormonal secretion. *J Neuroendocrinol* 2010, 22(6):620-628.
43. Stock S, Leichner P, Wong A C, Ghatei M A, Kieffer T J, Bloom S R, Chanoine J P: Ghrelin, peptide YY, glucose-dependent insulinotropic polypeptide, and hunger responses to a mixed meal in anorexic, obese, and control female adolescents. *J Clin Endocrinol Metab* 2005, 90(4): 2161-2168.
44. Moayyedi P, Soo S, Deeks J, Delaney B, Harris A, Innes M, Oakes R, Wilson S, Roalfe A, Bennett C et al: Eradication of *Helicobacter pylori* for non-ulcer dyspepsia. *Cochrane Database Syst Rev* 2005(1):CD002096.
45. Chandarana K, Drew M E, Emmanuel J, Karra E, Gelegen C, Chan P, Cron N J, Batterham R L: Subject standardization, acclimatization, and sample processing affect gut hormone levels and appetite in humans. *Gastroenterology* 2009, 136(7):2115-2126.
46. Cutler A F, Haystad S, Ma C K, Blaser M J, Perez-Perez G I, Schubert T T: Accuracy of invasive and noninvasive tests to diagnose *Helicobacter pylori* infection. *Gastroenterology* 1995, 109(1):136-141.
47. DeVault K R, Castell D O: Updated guidelines for the diagnosis and treatment of gastroesophageal reflux disease. *Am J Gastroenterol* 2005, 100(1):190-200.

Example 7

Administering *H. pylori* Strains to Treat Obesity, Metabolic Syndrome, and/or Diabetes For prevention or treatment of obesity, metabolic syndrome, and/or diabetes, *H. pylori* strains will be restored to the patient's stomach. An inventory of *H. pylori* strains will be available to physicians in a form that can be orally administered. Following administration of the selected *H. pylori* strain or strains, a culture of *Lactobacillus* species may be administered to suppress the *H. pylori* populations until more adult-like conditions develop in the stomach. The inventory of *H. pylori* strains will include those that are cag-positive (possessing a full functioning type IV secretion system that can inject the CagA protein and other *H. pylori* constituents into epithelial cells), and cag-negative, as well as strains varying in VacA activity (of genotypes $s_1$ or $s_2$, $m_1$ or $m_2$, $i_1$ or i₂), and in expression of the type I or type II Lewis antigen pathways. The strain or strain combination (involving a total of 2 to 5 *H. pylori* strains) will depend on the genotype and phenotype of the patient in relation to such issues as cytokine gene polymorphisms (e.g. IL-1 Beta receptor, TNF-α gene), as well as polymorphisms involved in regulation of ghrelin, leptin, and insulin, as well as Lewis blood group and secretor status, and HLA type.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all values are approximate, and are provided for description.

Patents, patent applications, publications, product descriptions, and protocols are cited throughout this application, the disclosures of which are incorporated herein by reference in their entireties for all purposes.

What is claimed:

1. A method of treating a disease in a mammal in need thereof, wherein the disease is selected from the group consisting of osteoporosis and other disorders of bone formation and mineralization, said method comprising administering to the mammal a therapeutically effective amount of a probiotic composition comprising one or more conditionally lethal bacterial strains, wherein the composition (i) stimulates the growth or activity of one or more bacterial taxa which are under-represented in microbiota of the mammal as compared to a healthy control or (ii) inhibits the growth or activity of one or more bacterial taxa which are over-represented in microbiota of the mammal as compared to a healthy control.

2. The method of claim 1, wherein the bacterial strain contained in the probiotic composition is a *Helicobacter pylori* strain.

3. The method of claim 1, wherein the probiotic composition further comprises a buffering agent selected from the group consisting of sodium bicarbonate, milk, yogurt, and infant formula.

4. The method of claim 1, wherein the microbiota are gastrointestinal microbiota.

5. The method of claim 1, wherein the probiotic composition is administered orally.

6. The method of claim 1, wherein the healthy control is a healthy subject of the same age and gender as the mammal being treated or an average of several healthy subjects of the same gender and average age as the mammal being treated.

7. The method of claim 1, wherein the mammal is human.

8. The method of claim 1, further comprising administering a prebiotic, wherein the prebiotic (i) stimulates growth or activity of one or more bacterial taxa which are under-represented in microbiota of the mammal as compared to the healthy control or (ii) inhibits growth or activity of one or more bacterial taxa which are over-represented in microbiota of the mammal as compared to the healthy control.

9. The method of claim 1, wherein the probiotic composition further comprises a prebiotic which stimulates growth or activity of the one or more bacterial strains in said composition.

10. The method of claim 1, said method further comprising identifying under-represented and/or over-represented bacterial taxa in the microbiota from the mammal as compared to a healthy control.

11. The method of claim 10, wherein identifying under-represented or over-represented bacterial taxa involves screening bacterial 16S rRNA genes using PCR.

12. The method of claim 10, wherein identifying under-represented or over-represented bacterial taxa involves high-throughput sequencing or PCR methods.

13. The method of claim 10, wherein identifying under-represented or over-represented bacterial taxa involves transciptomic or proteomic studies.

14. The method of claim 10, wherein the bacterial strain contained in the probiotic composition is a live bacterial strain.

15. The method of claim 10, wherein the bacterial strain contained in the probiotic composition is a conditionally lethal bacterial strain.

16. The method of claim 10, wherein the bacterial strain contained in the probiotic composition is a *Helicobacter pylori* strain.

17. The method of claim 10, wherein the probiotic composition further comprises a buffering agent selected from the group consisting of sodium bicarbonate, milk, yogurt, and infant formula.

18. The method of claim 10, wherein the microbiota are gastrointestinal microbiota.

19. The method of claim 10, wherein the probiotic composition is administered orally.

20. The method of claim 10, wherein the healthy control is a healthy subject of the same age and gender as the mammal being treated or an average of several healthy subjects of the same gender and average age as the mammal being treated.

21. The method of claim 10, wherein the mammal is human.

22. The method of claim 10, further comprising administering a prebiotic, wherein the prebiotic (i) stimulates growth or activity of one or more bacterial taxa which are under-represented in microbiota of the mammal as compared to the healthy control or (ii) inhibits growth or activity of one or more bacterial taxa which are over-represented in microbiota of the mammal as compared to the healthy control.

23. The method of claim 10, wherein the probiotic composition further comprises a prebiotic which stimulates growth or activity of the one or more bacterial strains in said composition.

24. A method of treating a disease in a mammal in need thereof, wherein the disease is selected from the group consisting of osteoporosis and other disorders of bone formation and mineralization, said method comprising administering to the mammal a therapeutically effective amount of a probiotic composition comprising a *Helicobacter pylori* strain, wherein the composition (i) stimulates the growth or activity of one or more bacterial taxa which are under-represented in microbiota of the mammal as compared to a healthy control or (ii) inhibits the growth or activity of one or more bacterial taxa which are over-represented in microbiota of the mammal as compared to a healthy control.

25. The method of claim 24, wherein the *Helicobacter pylori* strain contained in the probiotic composition is a live strain.

26. The method of claim 24, wherein the *Helicobacter pylori* strain contained in the probiotic composition is a conditionally lethal strain.

27. The method of claim 24, wherein the probiotic composition further comprises a buffering agent selected from the group consisting of sodium bicarbonate, milk, yogurt, and infant formula.

28. The method of claim 24, wherein the microbiota are gastrointestinal microbiota.

29. The method of claim 24, wherein the probiotic composition is administered orally.

30. The method of claim 24, wherein the healthy control is a healthy subject of the same age and gender as the mammal being treated or an average of several healthy subjects of the same gender and average age as the mammal being treated.

31. The method of claim 24, wherein the mammal is human.

32. The method of claim 24, further comprising administering a prebiotic, wherein the prebiotic (i) stimulates growth or activity of one or more bacterial taxa which are under-represented in microbiota of the mammal as compared to the healthy control or (ii) inhibits growth or activity of one or more bacterial taxa which are over-represented in microbiota of the mammal as compared to the healthy control.

33. The method of claim 24, wherein the probiotic composition further comprises a prebiotic which stimulates growth or activity of the *Helicobacter pylori* strain in said composition.

34. A method of treating a disease in a mammal in need thereof, wherein the disease is selected from the group consisting of osteoporosis and other disorders of bone formation and mineralization, said method comprising administering to the mammal a therapeutically effective amount of a probiotic composition comprising one or more bacterial strains, wherein the probiotic composition further comprises sodium bicarbonate, and (i) stimulates the growth or activity of one or more bacterial taxa which are under-represented in microbiota of the mammal as compared to a healthy control or (ii) inhibits the growth or activity of one or more bacterial taxa which are over-represented in microbiota of the mammal as compared to a healthy control.

35. The method of claim 34, wherein the bacterial strain contained in the probiotic composition is a live bacterial strain.

36. The method of claim 34, wherein the healthy control is a healthy subject of the same age and gender as the mammal being treated or an average of several healthy subjects of the same gender and average age as the mammal being treated.

37. The method of claim 34, wherein the mammal is human.

38. The method of claim 37, wherein the healthy control is a healthy human of the same age, gender and ethnicity as the human being treated or an average of several healthy humans of the same gender, ethnicity and average age as the human being treated.

39. The method of claim 34, wherein the microbiota are gastrointestinal microbiota.

40. The method of claim 34, wherein the probiotic composition is administered orally.

41. The method of claim 34, further comprising administering a prebiotic, wherein the prebiotic (i) stimulates growth or activity of one or more bacterial taxa which are under-represented in microbiota of the mammal as compared to the healthy control or (ii) inhibits growth or activity of one or more bacterial taxa which are over-represented in microbiota of the mammal as compared to the healthy control.

42. The method of claim 34, wherein the probiotic composition further comprises a prebiotic which stimulates growth or activity of the one or more bacterial strains in said composition.

43. The method of claim 34, wherein the bacterial strain contained in the probiotic composition is a conditionally lethal bacterial strain.

44. The method of claim 34, wherein the bacterial strain contained in the probiotic composition is a *Helicobacter pylori* strain.

45. A method of treating a disease in a mammal in need thereof, wherein the disease is selected from the group consisting of osteoporosis and other disorders of bone formation and mineralization, said method comprising administering to the mammal a therapeutically effective amount of a probiotic composition comprising one or more bacterial strains, wherein the probiotic composition stimulates the growth or activity of one or more species of Lachnospiraceae.

46. The method of claim 45, wherein the bacterial strain contained in the probiotic composition is a live bacterial strain.

47. The method of claim 45, wherein the bacterial strain contained in the probiotic composition is a conditionally lethal bacterial strain.

48. The method of claim 45, wherein the bacterial strain contained in the probiotic composition is a *Helicobacter pylori* strain.

49. The method of claim 45, wherein the probiotic composition further comprises a buffering agent selected from the group consisting of sodium bicarbonate, milk, yogurt, and infant formula.

50. The method of claim 45, wherein the microbiota are gastrointestinal microbiota.

51. The method of claim 45, wherein the probiotic composition is administered orally.

52. The method of claim 45, wherein the mammal is human.

53. The method of claim 45, further comprising administering a prebiotic, wherein the prebiotic stimulates growth or activity of one or more species of Lachnospiraceae.

54. The method of claim 45, wherein the probiotic composition further comprises a prebiotic which stimulates growth or activity of the one or more bacterial strains in said composition.

\* \* \* \* \*

UNITED STATES PATENT AND TRADEMARK OFFICE
CERTIFICATE OF CORRECTION

Page 1 of 1

PATENT NO. : 8,951,512 B2
APPLICATION NO. : 13/100977
DATED : February 10, 2015
INVENTOR(S) : Martin J. Blaser et al.

It is certified that error appears in the above-identified patent and that said Letters Patent is hereby corrected as shown below:

In the Specification

At Column 1, beginning in Line 16 and ending in Line 21 please replace:
"Research and development leading to certain aspects of the present invention were supported, in part, by grants 1UL1RR029893, R01DK090989, K23CA107123, R01GM63270 from the National Center for Research Resources, National Institutes of Health. Accordingly, the U.S. government may have certain rights in the invention."

With:
--This invention was made with government support under grants RR029893, DK090989, CA107123, GM063270 awarded by National Institutes of Health. The government has certain rights in the invention.--

Signed and Sealed this
Thirteenth Day of August, 2019

Andrei Iancu
*Director of the United States Patent and Trademark Office*